(12) United States Patent
Rosen et al.

(10) Patent No.: US 11,096,964 B2
(45) Date of Patent: Aug. 24, 2021

(54) COMPOSITIONS AND METHODS FOR IMMUNE CELL MODULATION IN ADOPTIVE IMMUNOTHERAPIES

(71) Applicant: Fate Therapeutics, Inc., San Diego, CA (US)

(72) Inventors: Jonathan Rosen, San Diego, CA (US); Betsy Rezner, San Diego, CA (US); Bahram Valamehr, San Diego, CA (US); Ryan Bjordahl, San Diego, CA (US); Eigen Peralta, San Diego, CA (US)

(73) Assignee: FATE THERAPEUTICS, INC., San Diego, CA (US)

(*) Notice: Subject to any disclaimer, the term of this patent is extended or adjusted under 35 U.S.C. 154(b) by 358 days.

(21) Appl. No.: 16/071,457

(22) PCT Filed: Jan. 20, 2017

(86) PCT No.: PCT/US2017/014408
§ 371 (c)(1),
(2) Date: Jul. 19, 2018

(87) PCT Pub. No.: WO2017/127729
PCT Pub. Date: Jul. 27, 2017

(65) Prior Publication Data
US 2019/0125795 A1 May 2, 2019

Related U.S. Application Data

(60) Provisional application No. 62/336,339, filed on May 13, 2016, provisional application No. 62/281,064, filed on Jan. 20, 2016.

(51) Int. Cl.
| | | |
|---|---|---|
| *A61K 36/17* | (2006.01) |
| *A61K 31/436* | (2006.01) |
| *A61P 31/00* | (2006.01) |
| *A61P 37/06* | (2006.01) |
| *A61P 35/00* | (2006.01) |
| *C12N 5/0783* | (2010.01) |
| *G01N 33/50* | (2006.01) |
| *A61K 35/17* | (2015.01) |
| *A61K 31/713* | (2006.01) |
| *A61K 31/7084* | (2006.01) |
| *A61K 31/7105* | (2006.01) |
| *A61K 45/06* | (2006.01) |
| *A61K 31/506* | (2006.01) |
| *A61K 38/20* | (2006.01) |

(52) U.S. Cl.
CPC .......... *A61K 35/17* (2013.01); *A61K 31/436* (2013.01); *A61K 31/506* (2013.01); *A61K 31/7084* (2013.01); *A61K 31/713* (2013.01); *A61K 31/7105* (2013.01); *A61K 45/06* (2013.01); *A61P 31/00* (2018.01); *A61P 35/00* (2018.01); *A61P 37/06* (2018.01); *C12N 5/0636* (2013.01); *C12N 5/0646* (2013.01); *G01N 33/505* (2013.01); *A61K 38/2086* (2013.01); *C12N 2501/06* (2013.01); *C12N 2501/2312* (2013.01); *C12N 2501/2318* (2013.01); *C12N 2501/25* (2013.01); *C12N 2501/727* (2013.01); *C12N 2501/999* (2013.01); *C12N 2503/02* (2013.01); *Y02A 50/30* (2018.01)

(58) Field of Classification Search
None
See application file for complete search history.

(56) References Cited

U.S. PATENT DOCUMENTS

| 2005/0075276 A1 | 4/2005 | Rudd |
| 2006/0247214 A1 | 11/2006 | DeLong et al. |

FOREIGN PATENT DOCUMENTS

| GB | 2 444 853 A | 6/2008 |
|---|---|---|
| GB | 2 444 853 B | 6/2008 |
| JP | 2019-502725 A | 1/2019 |
| WO | WO-99/01426 A1 | 1/1999 |
| WO | WO-01/12596 A1 | 2/2001 |
| WO | WO-02/06213 A2 | 1/2002 |
| WO | WO-02/06213 A3 | 1/2002 |
| WO | WO-03/077914 A1 | 9/2003 |
| WO | WO-2005/051301 A2 | 6/2005 |
| WO | WO-2005/051301 A3 | 6/2005 |
| WO | WO-2005/051301 A2 | 4/2007 |
| WO | WO-2005/051301 A3 | 4/2007 |
| WO | WO-2007/103901 A2 | 9/2007 |
| WO | WO-2007/103901 A3 | 9/2007 |
| WO | WO-2010/083298 A1 | 7/2010 |

(Continued)

OTHER PUBLICATIONS

Cao, et al. (Aug. 2014) "Metabolic Reprogramming Towards Aerobic Glycolysis Correlates with Greater Proliferative Ability and Resistance to Metabolic Inhibition in CD8 versus CD4 T cells", PLOS one, 9(8): e104104, 15 pages. (Year: 2014).*
Goldman AS, Prabhakar BS. Immunology Overview. In: Baron S, editor. Medical Microbiology. 4th edition. Galveston (TX): University of Texas Medical Branch at Galveston; 1996. Chapter 1. Available from: https://www.ncbi.nlm.nih.gov/books/NBK7795/, 48 pages as printed. (Year: 1996).*
Robson, et al. (2014) "Optimal effector functions in human natural killer cells rely upon autocrine bone morphogenetic protein signaling", Cancer Research, 74(18): 5019-31. (Year: 2014).*

(Continued)

*Primary Examiner* — Robert M Kelly
(74) *Attorney, Agent, or Firm* — Mintz, Levin, Cohn, Ferris, Glovsky and Popeo, P.C.

(57) ABSTRACT

Compounds that either produced a higher proportion or greater absolute number of phenotypically identified nave, stem cell memory, central memory T cells, adaptive NK cells, and type I NKT cells are identified. Compositions and methods for modulating immune cells including T, NK, and NKT cells for adoptive cell therapies with improved efficacy are provided.

31 Claims, 25 Drawing Sheets

(56) References Cited

FOREIGN PATENT DOCUMENTS

| WO | WO-2015/155738 A2 | 10/2015 |
| WO | WO-2015/155738 A3 | 10/2015 |
| WO | WO-2015/188119 A1 | 12/2015 |
| WO | WO-2016/123117 A1 | 8/2016 |
| WO | WO-2016/179283 A1 | 11/2016 |
| WO | WO-2017/127755 A1 | 7/2017 |

OTHER PUBLICATIONS

Mack, et al. (2011) "Generation of Induced Pluripotent Stem Cells from CD34+ Cells across Blood Drawn from Multiple Donors with Non-integrating Episomal Vectors", PLoS One, 6(11): e27956, 14 pages long. (Year: 2011).*

Aoukaty, A. et al. (Apr. 15, 2005). "Role for glycogen synthase kinase-3 in NK cell cytotoxicity and X-linked lymphoproliferative disease," *The Journal of Immunology* 174(8):4551-4558.

Araki, K. et al. (May 2010). "The role of mTOR in memory CD8 T-cell differentiation," *Immunol Rev* 235(1):234-243.

Asanuma, S. et al. (Jun. 2011, e-published Nov. 24, 2010). "Expansion of CD4(30 )CD25 (+) regulatory T cells from cord blood CD4(+) cells using the common γ-chain cytokines (IL-2 and IL-15) and rapamycin," *Ann Hematol* 90(6):617-624.

Battaglia, M. et al. (Jun. 15, 2005, e-published Mar. 3, 2005). "Rapamycin selectively expands CD4+CD25+FoxP3+ regulatory T cells," *Blood* 105(12):4743-4748.

Berger, C. et al (Jan. 2008). "Adoptive transfer of effector CD8+ T cells derived from central memory cells establishes persistent T cell memory in primates," *J Clin Invest* 118(1):294-305.

Esteban, M.A. et al. (Jan. 8, 2010, e-published Dec. 31, 2009). "Vitamin C enhances the generation of mouse and human induced pluripotent stem cells," *Cell Stem Cell* 6(1):71-79.

Extended European Search Report dated Oct. 2, 2019, for EP Patent Application No. 17742046.0, 12 pages.

Feng, B. et al. (Apr. 3, 2009). "Molecules that promote or enhance reprogramming of somatic cells to induced pluripotent stem cells," *Cell Stem Cell* 4(4):301-312.

Huangfu, D et al. (Jul. 2008, e-published Jun. 22, 2008). "Induction of pluripotent stem cells by defined factors is greatly improved by small-molecule compounds," *Nat Biotechnol* 26(7):795-797.

Huangfu, D et al. (Nov. 2008, e-published Oct. 12, 2008). "Induction of pluripotent stem cells from primary human fibroblasts with only Oct4 and Sox2," *Nat Biotechnol* 26(11):1269-1275.

Ichida, J.K. et al. (Nov. 6, 2009, e-published Oct. 8, 2009). "A small-molecule inhibitor of tgf-Beta signaling replaces sox2 in reprogramming by inducing nanog," *Cell Stem Cell* 5(5):491-503.

Inman, G.J. et al. (Jul. 2002). "SB-431542 is a potent and specific inhibitor of transforming growth factor-beta superfamily type I activin receptor-like kinase (ALK) receptors ALK4, ALK5, and ALK7," *J Mol. Pharmacol.* 62(1):65-74.

International Search Report dated Apr. 18, 2017 for PCT/US2017/014408, filed Jan. 20, 2017, 5 pages.

Kim, D. et al. (Jun. 5, 2009, e-published May 28, 2009). "Generation of human induced pluripotent stem cells by direct delivery of reprogramming proteins," *Cell Stem Cell* 4(6):472-476.

Kim, G.G. et al. (Aug. 31, 2007, e-published Jun. 28, 2007). "A novel multiparametric flow cytometry-based cytotoxicity assay simultaneously immunophenotypes effector cells: comparisons to a 4 h 51Cr-release assay," *J Immunol Methods* 325(1-2):51-66.

King, C.C. et al. (Jun. 16, 2000). "Sphingosine is a novel activator of 3-phosphoinositide-dependent kinase 1," *Journal of Biological Chemistry* 275(24):18108-18113.

Liu, Y. et al. (Jan. 2015, e-published Jul. 14, 2014). "mTOR signaling in T cell immunity and autoimmunity," *Int Rev Immunol* 34(1):50-66.

Lyssiotis, C.A. et al. (Jun. 2, 2009, e-published May 15, 2009). "Reprogramming of murine fibroblasts to induced pluripotent stem cells with chemical complementation of Klf4," *PNAS USA* 106(22):8912-8917.

Maherali, N. et al. (Nov. 3, 2009, e-published Sep. 17, 2009). "Tgfβ signal inhibition cooperates in the induction of iPSCs and replaces Sox2 and cMyc," *Curr Biol* 19(20):1718-1723.

Partial Supplementary European Search Report dated Jun. 24, 2019, for EP Patent Application No. 17742046.0, 13 pages.

Perkins, M.R. et al. (Dec. 3, 2015). "Manufacturing an Enhanced CAR T Cell Product by Inhibition of the PI3K/Akt Pathway During T Cell Expansion Results in Improved In Vivo Efficacy of Anti-BCMA CAR T Cells," *Blood* 126(23): 3 pages.

Rosen, J. et al. (Dec. 2, 2016). "Identification of small molecule modulators to enhance the therapeutic properties of chimeric antigen receptor T cells," *Blood* 128:4712.

Saha, K. et al. (Dec. 4, 2009). "Technical challenges in using human induced pluripotent stem cells to model disease," *Cell Stem Cell* 5(6):584-595.

Shi, Y. et al. (Jun. 5, 2008). "A combined chemical and genetic approach for the generation of induced pluripotent stem cells," *Cell Stem Cell* 2(6):525-528.

Shi, Y. et al. (Nov. 6, 2008). "Induction of pluripotent stem cells from mouse embryonic fibroblasts by Oct4 and Klf4 with small-molecule compounds," *Cell Stem Cell* 3(5):568-574.

Silva, J. et al. (Oct. 21, 2008). "Promotion of reprogramming to ground state pluripotency by signal inhibition," *PloS Biol* 6(10):e253.

Sommermeyer, D. et al. (Feb. 2016, e-published Sep. 15, 2015). "Chimeric antigen receptor-modified T cells derived from defined CD8+ and CD4+ subsets confer superior antitumor reactivity in vivo," *Leukemia* 30(2):492-500.

Takahashi, K. et al. (Aug. 25, 2006, e-published Aug. 10, 2006). "Induction of pluripotent stem cells from mouse embryonic and adult fibroblast cultures by defined factors," *Cell* 126(4):663-676.

Takahashi, K. et al. (Nov. 30, 2007). "Induction of pluripotent stem cells from adult human fibroblasts by defined factors," *Cell* 131(5):861-872.

Written Opinion dated Apr. 18, 2017 for PCT/US2017/014408, filed Jan. 20, 2017, 5 pages.

Yamanaka, S. et al. (Jul. 2, 2009). "Elite and stochastic models for induced pluripotent stem cell generation," *Nature* 460(7251):49-52.

Yu, J. et al. (Dec. 21, 2007, e-published Nov. 20, 2007). "Induced pluripotent stem cell lines derived from human somatic cells," *Science* 318(5858):1917-1920.

Zhou, H. et al. (May 8, 2009, e-published Apr. 23, 2009). "Generation of induced pluripotent stem cells using recombinant proteins," *Cell Stem Cell* 4(5):381-384.

Cheng, M. et al. (May 2013, e-published Apr. 22, 2013). "NK cell-based immunotherapy for malignant diseases," *Cell Mol Immunol* 10(3):230-252.

Fujisaki, H. et al. (May 1, 2009, e-published Apr. 21, 2009). "Expansion of highly cytotoxic human natural killer cells for cancer cell therapy," *Cancer Res* 69(9):4010-4017.

Wai, L-E. et al. (Jan. 15, 2008). "Rapamycin, but not cyclosporine or FK506, alters natural killer cell function," *Transplantation* 85(1):145-149.

\* cited by examiner

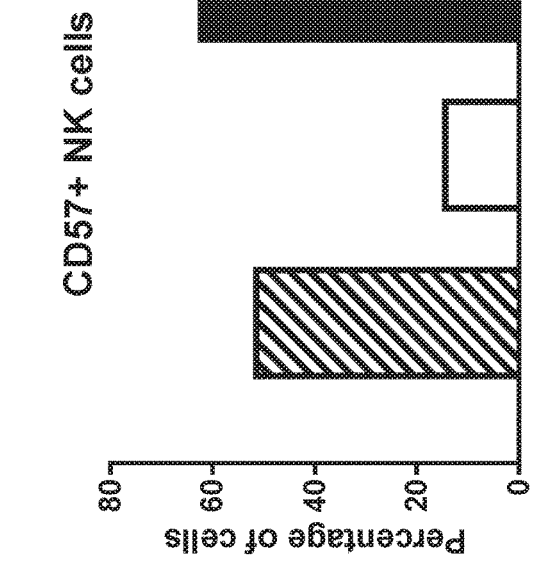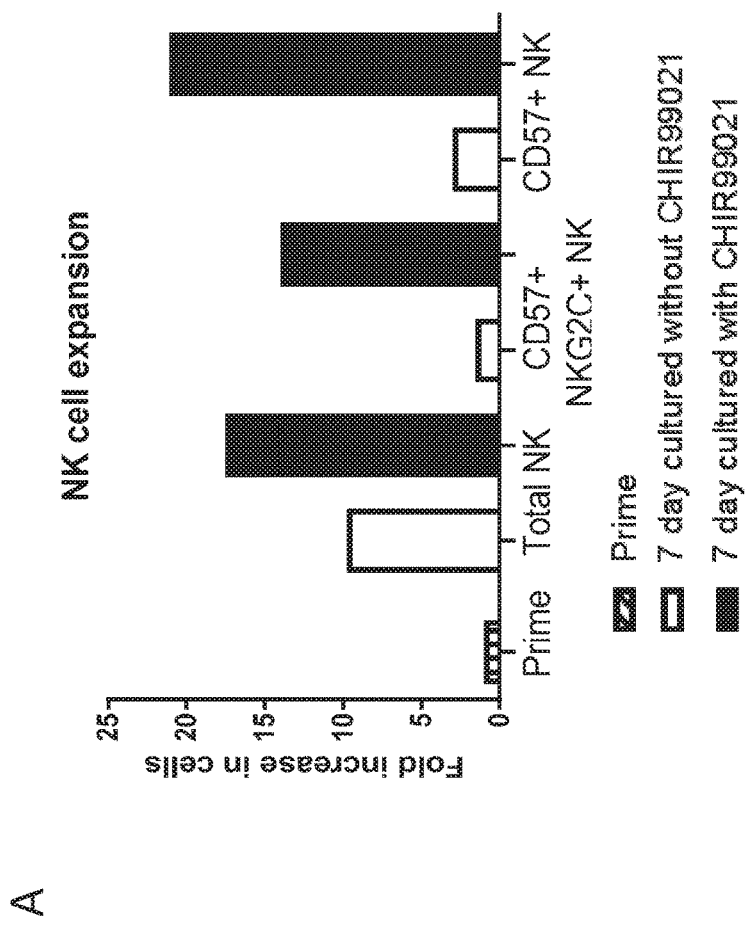
Figure 4

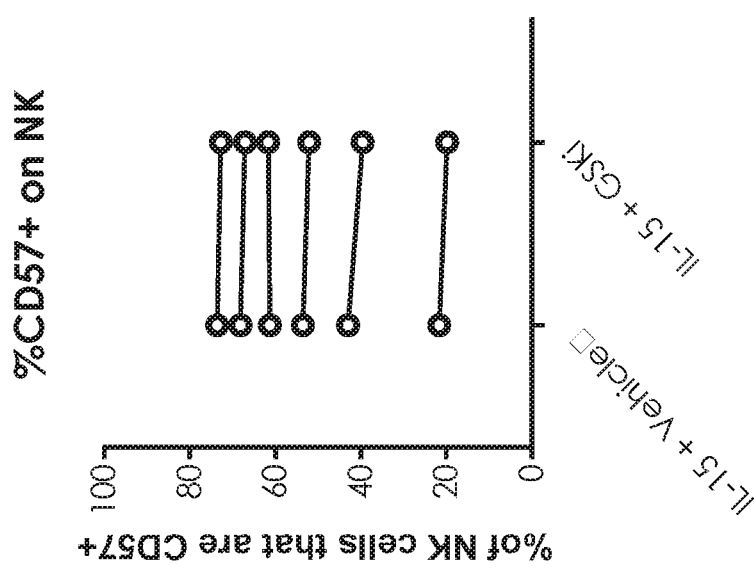
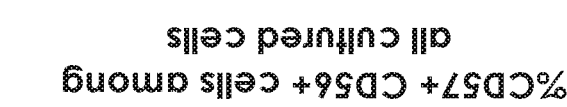
Figure 11

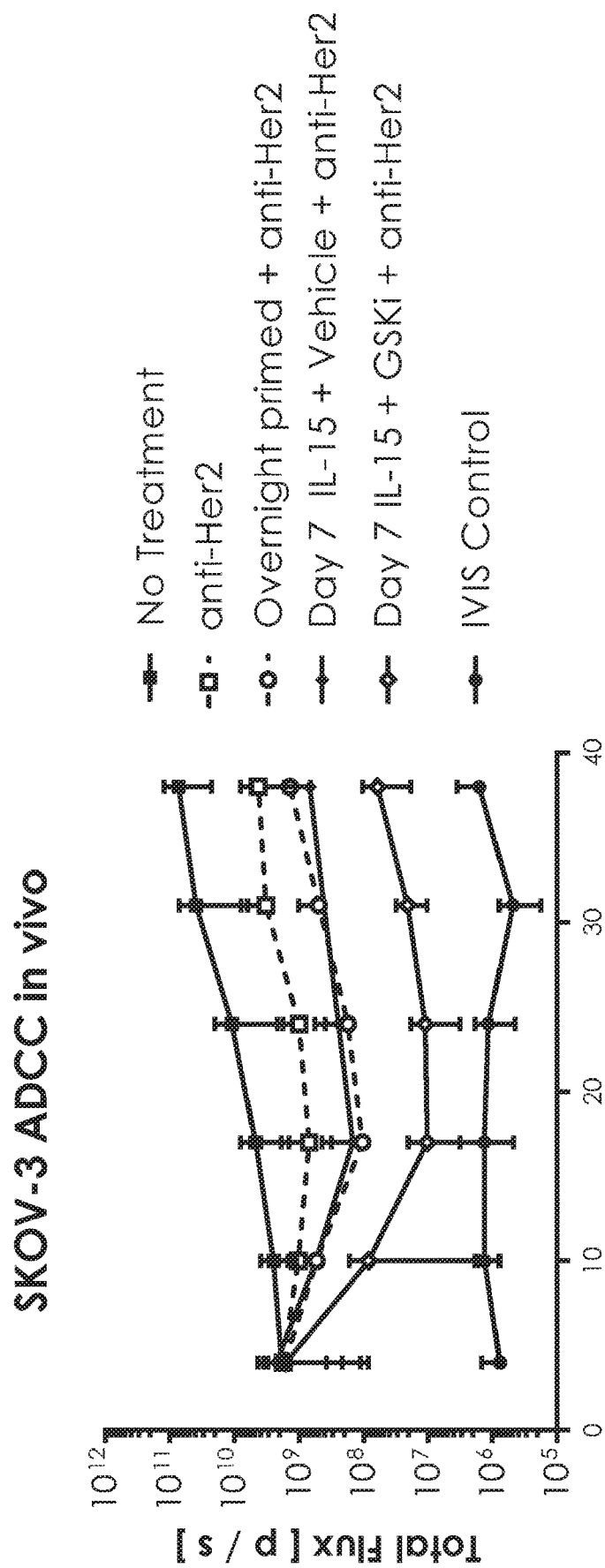

COMPOSITIONS AND METHODS FOR IMMUNE CELL MODULATION IN ADOPTIVE IMMUNOTHERAPIES

RELATED APPLICATION

This application claims priority to U.S. Provisional Application Ser. No. 62/281,064, filed Jan. 20, 2016 and U.S. Provisional Patent Application No. 62/336,339, filed May 13, 2016, the disclosures of which are hereby incorporated by reference in their entirety.

FIELD OF THE INVENTION

The present disclosure is broadly concerned with the field of adoptive immune cell therapies. More particularly, the present disclosure is concerned with the use of small molecules for modulating immune-cells suitable for adoptive cell therapies.

BACKGROUND OF THE INVENTION

Adoptive immunotherapy involves administration of immune cells to patients having cancer, tumor, or infections, whereby the administered immune cells provide a therapeutic benefit to the patients. Generally speaking, immune cells suitable for immunotherapy include, but are not limited to, B cells, dendritic cells (DC), T cells, Natural Killer (NK) cells, NKT (Natural Killer T) cells, and hematopoietic stem or progenitor cells. Mediating complete and durable disease responses in patients is the central goal of these cell-based immunotherapies.

Advances in our understanding of the biological mechanisms behind the effectiveness of adoptive T cell therapies, including, but not limited to, CAR-T cells, TCR-T cells, virus-specific T cells (VSTs) and tumor-infiltrating T cell (TILs), have underscored the importance of the certain attributes associated with transferred T cells and revealed the complexity of the inhibitory barriers posed by the host and tumor cells that need to be overcome for the success of the treatment of cancer. Among T cell factors, the avidity of the T cell receptor (TCR) or chimeric antigen receptor (CAR), the proliferative and survival capacities, migration to the tumor site(s), and the ability to sustain effector functions within the tumor have, in correlative studies, been shown to be crucial determinants for triggering the eradication of malignant cells. However, adding to another layer of complexity, even though some of these desirable attributes were recognized, the pathways or players driving these attributes are still unclear, which limits one's ability to intervene and obtain cells having desired quantity and quality for their therapeutic uses.

Using CAR-T cell therapy as an example, the therapy has to overcome multiple challenges including CAR-T potency and persistence, migration to the tumor, the immunosuppressive tumor microenvironment, tumor heterogeneity and patient safety. Multiple approaches are being applied to overcome these challenges. For example, specific T-cell subsets are selected for therapeutic use and further engineering of the CAR may be used to improve tumor targeting, CAR potency and on-target/off-tumor safety issues. However, improving the CAR-T therapeutic efficacy, including CAR-T persistence and migration remains to be resolved. It has been shown that the in vivo efficacy of the T cell therapy can be strongly influenced by the manufacturing process which is dependent upon both the starting population of T cells going into the process or feedstock, and the ex vivo expansion and activation methods utilized. It has been demonstrated that the differentiation state of the administered T cells can significantly affect in vivo persistence and anti-tumor activity. T helper (CD4+ T cells) and cytotoxic T cells (CD8+), specifically, naïve (Tn), stem cell memory (Tscm) and central memory (Tcm) T cells, characterized by the expression of the CCR7 and CD62L markers, mediate superior anti-tumor activity in both mouse models (Sommermeyer et al. 2015) and in nonhuman primate models (Berger et al. 2008).

During the manufacturing process, therapeutic cells (or cell populations) are typically activated and expanded. This process generally drives differentiation of the cells and leads to an increase in the proportion of the cells in a more differentiated state—in the case of T-cells, the more differentiated cells are phenotypically characterized as effector memory or effector T cells. Once infused into patients, these more differentiated cells have a lower capacity to proliferate and a lower potential to persist as a long-lived or persistent population, as compared to cells in less differentiated states. Thus, there is an urgent need in the art not only for compositions and methods useful for maintaining and expanding desired immune cell subsets, but also for reducing cell differentiation during expansion, and for dedifferentiating cells to less differentiated cells, thereby obtaining desired immune cell subsets that have greater capacity to proliferate and persist in order to improve the efficacy of various adoptive immunotherapies.

Similar efficacy issues exist in NK-cell based therapies as well. Natural killer cells have traditionally been categorized as innate immune cells that are characterized as being relatively short-lived and exhibit minimal change in response to secondary exposure to a stimulus i.e., display limited target memory responses. However, recent research has uncovered information on both activating and inhibitory NK cell receptors which play important roles including self-tolerance and sustaining NK cell activity. Data have demonstrated the ability of NK cells to readily adjust to the immediate environment and formulate antigen-specific immunological memory, which is fundamental for responding to secondary exposure to the same antigen. A subpopulation of NK cells, now called adaptive NK cells or memory NK cells, have been identified by several groups. These cells have many functional characteristics similar to CD8+ T cells, including being longer-lived and having enhanced response to stimuli after an initial exposure. These properties may result in a more efficacious cell therapy strategy, as compared to canonical NK cells. Expanding and maintaining adaptive/memory NK cells that mediate durable antigen-specific recognition in vivo would be a key to improving NK-cell based adoptive immunotherapy.

Further, it is believed that, like T and NK cells, improvements can be made to isolate more efficacious NKT cells, a type of CD1d-restricted T cell playing a role in both the innate and adaptive immune systems, which can be targeted for modulation to yield an improved cell therapy.

Since the final state of the cells, or specifically, the cell subtypes, going into the patient can be defined in large part by the manufacturing process, the importance of that process cannot be overstated. Preferentially maintaining or expanding cell subpopulations having a desired differentiation state, and/or adaptive immune cell characteristics during cell culture and expansion could be extremely beneficial for enhancing the efficacy of cell-based therapies. Thus, a manufacturing approach that can enhance the desired T, NK or NKT cell subsets both in quantity and quality could provide a significant enhancement of their therapeutic efficacy.

There is a substantial need in the art for immune cell subsets with improved therapeutic efficacy. However, while certain desirable attributes of therapeutic immune cells are known, the pathways and/or players involved in achieving these attributes are largely unknown. The methods and compositions of the present invention addresses this need and provide other related advantages in the field of immune cell therapy.

SUMMARY OF THE INVENTION

The present invention provides compositions and methods for modulating one or more populations or subpopulations of immune cells to improve their therapeutic potential for adoptive immunotherapies. It is an object of the present invention to provide one or more compounds, either alone or in combination to improve proliferation, persistence, cytotoxicity, and/or cell recall/memory of therapeutic immune cells by, for example, increasing the number or ratio of a subpopulation of cells that displays improvement in at least one of the following qualities that are expected to result in better immunotherapeutic results: migration, homing, cytotoxicity, maintenance, expansion, persistence, longevity, desired states of differentiation.

One aspect of the invention provides a composition for improving therapeutic potential of immune cells suitable for adoptive cell-based therapies, and the composition comprises one or more agents selected from the group consisting of compounds listed in Table 1: Dorsomorphin; Heptelidic acid; 1-Pyrrolidinecarbodithioic acid, ammonium salt; 2-dexoyglucose (2-DG); GSK3 Inhibitor; Rho kinase inhibitors; MEK inhibitors; PDK1 agonist; TGFβ inhibitors; 6-Mercaptopurine; AC-93253 iodide; Tiratricol; PI-103; Fulvestrant; Thapsigargin; SU 4312; Telmisartan; Cyclosporin A; 1,3,5-tris(4-hydroxyphenyl)-4-propyl-1H-pyrazole; BAY 61-3606; Protoporphyrin IX disodium; Rapamycin; HS173; LY294002; Pictilisib; 5-Azacytidine; Fludarabine; Roscovitine, (S)-Isomer; PAC-1; 8-Quinolinol, 5,7-dichloro-; Nitrofurantoin; 8-Quinolinol, 5-chloro-7-iodo-; 2-Naphthacenecarboxamide, 7-chloro-4-(dimethylamino)-1,4,4a,5,5a,6,11,12a-octahy; Nifuroxazide; Tosufloxacin hydrochloride; Sertraline; Diethylenetriaminepentaacetic acid, penta sodium; Edrophonium chloride; BIX01294; Terfenadine; and dmPGE2. The one or more agents selected from the group consisting of compounds listed in Table 1 improve therapeutic potential of immune cells or one or more subpopulation thereof via modulating the immune cells using said one or more agent. In some embodiments, the modulation of the immune cells is ex vivo.

In some embodiments, the one or more of compounds listed in Table 1 modulates cell expansion, maintenance and/or differentiation, and thereby improve proliferation, cytotoxicity, cytokine response and secretion, cell recall, and/or persistence of the immune cells, or one or more subpopulation thereof.

In one embodiment, the one or more of the compounds listed in Table 1 improves cell survival rate of the immune cell, or one or more subpopulation thereof both ex vivo and in vivo.

In one embodiment, the one or more of the compounds listed in Table 1 increases the ratio of one or more desired cell subpopulation of the immune cells.

In some embodiments, the present invention provides one or more selected agents herein to improve therapeutic efficacy of a population or subpopulation of immune cells, including but not limited to T, NK and NKT cells. In some embodiments, the immune cells immune cells suitable for adoptive cell-based therapies comprise T cells, NKT cells, or NK cells. In some embodiments, the immune cells subject to the treatments comprise T cells, as such the one or more desired cell subpopulations has an increased ratio comprises naïve T cells, stem cell memory T cells, and/or central memory T cells. In some embodiments, the immune cells subject to the treatments using the agents comprise NKT cells, as such the one or more desired cell subpopulations has an increased ratio comprise type I NKT cells. In some other embodiments, the immune cells subject to the treatments using the agents comprise NK cells, and wherein the one or more desired cell subpopulations has an increased ratio comprise adaptive NK cells.

In some embodiments, the composition comprising one or more agents selected from the group consisting of the compounds, or derivatives, analogues or pharmaceutically acceptable salts thereof, listed in Table 1. The compounds, or derivatives, analogues or pharmaceutically acceptable salts thereof further comprise ester, ether, solvate, hydrate, stereoisomer, and prodrug of the compounds of Table 1.

In some embodiments, the composition for improving therapeutic potential of immune cells comprises at least one agent selected from Group I, and one or more agents selected from Group II, Group III, Group IV, and/or Group V.

Group I comprises: dorsomorphin, heptelidic acid, 1-Pyrrolidinecarbodithioic acid, and 2-DG. Without being limited to the theory, Group I agents, among other potential roles, impact cell metabolism and nutrient sensing.

Group II comprises: GSK3 Inhibitor, ROCK inhibitor, TGFβ receptor inhibitor, MEK inhibitor, PDK1 agonist, 6-Mercaptopurine, AC-93253 iodide, tiratricol, PI-103, fulvestrant, thapsigargin, SU 4312, U0126, telmisartan, cyclosporin A, 1,3,5-tris(4-hydroxyphenyl)-4-propyl-1H-pyrazole, BAY 61-3606, protoporphyrin IX disodium, rapamycin, TWS119, HS173, LY294002, and Pictilisib. Without being limited to the theory, Group II agents, among other potential roles, impact signal transduction in various functional pathways.

Group III comprises: 5-Azacytidine, fludarabine, roscovitine, and PAC-1. Without being limited to the theory, Group III agents, among other potential roles, impact cell proliferation and apoptosis.

Group IV comprises: 5,7-dichloro-8-Quinolinol, 2-Naphthacenecarboxamide, 7-chloro-4-(dimethylamino)-1,4,4a,5, 5a,6,11,12a-octahy, Nifuroxazide, and Tosufloxacin hydrochloride. Without being limited to the theory, Group IV agents, among other potential roles, may impact cell properties relating to infective processes.

Group V comprises: sertraline, diethylenetriaminepentaacetic acid, edrophonium chloride, BIX01294, terfenadine, and dmPGE2. Without being limited to the theory, Group V agents, among other potential roles, generally impact other cell properties relating to expansion, maintenance, differentiation, dedifferentiation, survival rate, proliferation, cytotoxicity, cell recall, and/or persistence.

In some other embodiments, the composition for improving therapeutic potential of immune cells comprises at least one agent selected from Group II, and one or more agents selected from Group I, Group III, Group IV, and/or Group V.

In still other embodiments, the composition for improving therapeutic potential of immune cells comprises at least one agent selected from Group III, and one or more agents selected from Group I, Group II, Group IV, and/or Group V.

In yet other embodiments, the composition for improving therapeutic potential of immune cells comprises at least one agent selected from Group IV, and one or more agents selected from Group I, Group II, Group III, and/or Group V.

In still some other embodiments, the composition for improving therapeutic potential of immune cells comprises at least one agent selected from Group V, and one or more agents selected from Group I, Group II, Group III, and/or Group IV.

In some embodiments, the composition for improving therapeutic potential of immune cells comprises a combination comprising at least one agent selected from the group consisting of TWS119, HS173, LY294002, Pictilisib, and 2-DG; and one or more additional agent selected from the group consisting of compounds listed in Table 1. In some particular embodiments, the composition comprises a synergistic combination of two or more agents selected from the group consisting of TWS119, HS173, LY294002, Pictilisib, and 2-DG.

In some embodiments, the composition comprising one or more agents selected from the group consisting the compounds listed in Table 1 further comprises at least one organic solvent selected from the group consisting of dimethyl sulfoxide (DMSO), N,N-dimethylformamide (DMF), dimethoxyethane (DME), dimethylacetamide, ethanol and combinations thereof.

Another aspect of the invention provides a composition comprising a population or subpopulation of immune cells, and one or more agents selected from the group consisting of the compounds listed in Table 1, and derivatives and analogues thereof. In some embodiments, the immune cells are contacted with the one or more agents to improve therapeutic potential of the immune cells for adoptive cell therapy in comparison to immune cells without such treatment. In some embodiments, the immune cells are contacted with the one or more agents to improve cell expansion, maintenance, differentiation, dedifferentiation, and/or survival rate in comparison to immune cells without the same treatment. In yet some other embodiments, the immune cells are contacted with the one or more agents to improve cell proliferation, cytotoxicity, persistence, and/or recall in comparison to immune cells without the same treatment.

In some embodiments, the immune cells contacted with the one or more agents have an increased number or ratio of a desired subpopulation of the immune cells in comparison to immune cells without the same treatment. In some embodiments, the immune cells comprise T, NK or NKT cells. In one embodiment, the composition comprises a population of T cells, as such the desired subpopulation of immune cells after contacting the agent(s) comprise naïve T cells, stem cell memory T cells, and/or central memory T cells. In some embodiments, the composition comprises a population of NKT cells, as such the desired subpopulation of immune cells after contacting the agents comprise type I NKT cells. In yet some other embodiments, the immune cells comprise a population of NK cells. In some other embodiments, the NK cells comprise CD57− NK cells or CD57−NKG2C+ NK cells. As such the desired subpopulation of immune cells after contacting the agents comprise CD57+ NK cells. In some embodiments, the CD57+ NK cells comprise adaptive NK cells. In other embodiments the adaptive NK cells comprise CD57+ and at least one of NKG2C+, low PLZF, low SYK, low FcεRγ, low EAT-2, low TIGIT, low PD1, low CD7, low CD161, high LILRB1, high CD45RO, and low CD45RA.

In some embodiments, the population or subpopulation of immune cells of the composition are isolated from or comprised in peripheral blood, bone marrow, lymph node tissue, cord blood, thymus tissue, tissue from a site of infection, ascites, pleural effusion, spleen tissue, or tumors of a subject. The subject may be healthy, may have an autoimmune disease, a hematopoietic malignancy, a virus infection or a solid tumor, or may have been previously administered with genetically modified immune cells. In some embodiments, the subject may be CMV seropositive. In some other embodiments, the isolated immune cells for modulation are genetically modified (genetically engineered or naturally derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, the genetically modified immune cells are isolated for ex vivo modulation using the present compositions and methods as disclosed. In some embodiments, after modulation, the genetically modified immune cells isolated from a subject may be administered to the same donor or a different patient.

In yet another embodiment, the immune cells are differentiated in vitro from stem cells, hematopoietic stem or progenitor cells, or progenitor cells; or are trans-differentiated in vitro from non-pluripotent cells of hematopoietic or non-hematopoietic lineage. In some particular embodiments, the immune cells of the composition comprise an exogenous nucleic acid encoding a T Cell Receptor (TCR), a Chimeric Antigen Receptor (CAR), and/or overexpression of CD16 and variants thereof. In one embodiment, the CD16 is hnCD16 (high-affinity non-cleavable CD16).

In still some other embodiments, the immune cells of the composition are differentiated in vitro from stem cells, hematopoietic stem or progenitor cells, or progenitor cells. In one embodiment, the stem cell is induced pluripotent stem cells (iPSCs) or embryonic stem cells (ESCs). In one embodiment, the progenitor cell is a CD34+ hemogenic endothelium cell, a multipotent progenitor cell, a T cell progenitor cell, a NK progenitor cell, or a NKT progenitor cell. In some embodiments, the stem cell, hematopoietic stem or progenitor cell, or progenitor cell is genomically engineered and comprises an insertion, a deletion, or a nucleic acid replacement, or comprises at least one genetically modified modality. In one particular embodiment, the stem cell, hematopoietic stem or progenitor cell, or progenitor comprises an exogenous nucleic acid encoding a T Cell Receptor (TCR), a Chimeric Antigen Receptor (CAR), and/or overexpression of CD16. In some other embodiments, the immune cells of the composition are trans-differentiated in vitro from non-pluripotent cells of hematopoietic or non-hematopoietic lineage. In some embodiments, the desired subpopulation of immune cells after modulation comprises immune cells having at least one genetically modified modality. In one embodiment, the desired subpopulation of immune cells comprises CD57+ NK cells having at least one genetically modified modality. In some embodiments, the genetically modified modality comprises at least one of safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modalities comprise one or more of (i) deletion or reduced expression of B2M, TAP1, TAP2, Tapasin, NLRC5, PD1, LAG3, TIM3, RFXANK, CIITA, RFX5, or RFXAP, and any gene in the chromosome 6p21 region; and (ii) introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers. In one particular embodiment, the CD57+ NK cells comprise expression of hnCD16. In yet another embodiment, the CD57+ NK cells comprising expression of hnCD16 are adaptive NK cells. In another embodiment, the CD57+ NK cells comprising expression of hnCD16 further comprise at least one of NKG2C+, low PLZF, low SYK, low FcεRγ, low EAT-2, low TIGIT, low PD1, low CD7, low CD161, high LILRB1, high CD45RO, and low CD45RA.

In some embodiments, the composition comprises one or more of a GSK3 inhibitor, a TGFβ receptor inhibitor, a ROCK inhibitor, a MEK inhibitor, a PDK1 agonist, and rapamycin. In some embodiments, the composition comprises a GSK3 inhibitor. In some embodiments, the composition comprising the immune cells and one or more agents selected from the group consisting of compounds listed in Table 1, further comprises one of more additional additives selected from the group consisting of peptides, cytokines, mitogens, growth factors, small RNAs, dsRNAs (double stranded RNAs), mononuclear blood cells, feeder cells, feeder cell components or replacement factors, vectors comprising one or more polynucleic acids of interest; an antibody, or an antibody fragment; and a chemotherapeutic agent, a radioactive moiety, or an immunomodulatory drug (IMiD). In some of these embodiments, the antibody, or antibody fragment, specifically binds to a viral antigen. In other embodiments, the antibody, or antibody fragment, specifically binds to a tumor antigen. In some embodiments, the additional additive comprises. Chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art.

In one specific embodiment, the composition comprises a mixture of a population or subpopulation of immune cells and one or more of a GSK3 inhibitor, a TGFβ receptor inhibitor, a ROCK inhibitor, a MEK inhibitor, a PDK1 agonist, and an mTOR inhibitor, wherein the immune cells comprise NK cells. In some embodiments, the mTOR inhibitor is selected from rapamycin, and analogues or derivatives thereof. In some embodiments, the mTOR inhibitor is selected from rapamycin, and analogues or derivatives thereof, which comprise sirolimus, sirolimus derivatives, temsirolimus, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, and other O-alkylated or O-methylated rapamycin derivatives. In one embodiment, the composition comprises a GSK3 inhibitor. In another embodiment, the composition comprises a GSK3 inhibitor, a MEK inhibitor and rapamycin. In yet another embodiment, the composition comprises a GSK3 inhibitor. In one embodiment, the composition comprising a GSK3 inhibitor further comprises at least one of the stimulating cytokines comprising IL2, IL15, IL12, IL18 and IL21. In one embodiment, the composition comprising a GSK3 inhibitor further comprises one or more of a MEK inhibitor, rapamycin, and a STING agonist. In some embodiments, the STING agonist comprises cyclic dinucleotides (CDN), or xanthenone, or an analog or a derivative thereof. In some embodiments, CDNs may be synthetic or originated from prokaryotic or mammalian cells. In some other embodiments, STING agonists comprise at least one molecule selected from the group consisting of cGAMP, c-di-GMP, c-di-AMP, c-di-IMP, c-di-UMP, cAMP-GMP, R,R dithio-modified CDA compounds (ML RR-S2 CDA and RR-S2 CDA), ML RR-S2 cGAMP, DMXAA (5,6-dimethylxanthenone-4-acetic acid), and analogs and derivatives thereof.

One aspect of the invention provides a composition for improving therapeutic potential of immune cells suitable for adoptive cell-based therapies, comprising one or more agents selected from the group consisting of compounds listed in Table 1, and derivatives and analogues thereof, wherein the one or more agents improves therapeutic potential of immune cells thereof via modulating the immune cells. In some embodiments of said composition, the agent is capable of modulating cell expansion, maintenance and/or differentiation; improving cell proliferation, cytotoxicity, cytokine response and secretion, recall, and/or persistence; improving cell survival rate; and/or increasing the ratio of one or more desired cell subpopulation of the immune cells. In some embodiments, the derivatives and analogues comprise salt, ester, ether, solvate, hydrate, stereoisomer, and prodrug of the agents of Table 1.

In some embodiments, the immune cells suitable for modulation by said agents comprise T cells, NKT cells, and/or NK cells. In some embodiments, the NK cells for modulation comprise CD57− NK cells, and/or CD57− NKG2C+ NK cells. In some embodiments, the modulated immune cells comprise one or more desired cell subpopulations with an increased ratio, and the subpopulation may be naïve T cells, stem cell memory T cells, and/or central memory T cells; type I NKT cells; or CD57+ NK cells. In some embodiments, the CD57+ NK cells comprise adaptive NK cells. In some embodiments, said adaptive NK cells is characterized as CD57+ and at least one of NKG2C+, low PLZF, low SYK, low FcεRγ, low EAT-2, low TIGIT, low PD1, low CD7, low CD161, high LILRB1, high CD45RO, and low CD45RA. In some embodiments, the adaptive NK cells is characterized as CD57+ NKG2C+.

In some embodiments, the immune cells suitable for modulation by said agents are isolated from or comprised in peripheral blood, bone marrow, lymph node tissue, cord blood, thymus tissue, tissue from a site of infection, ascites, pleural effusion, spleen tissue, or tumors. In one embodiment, the immune cells are isolated from a healthy subject; a subject having an autoimmune disease, a hematopoietic malignancy, a virus infection or a solid tumor; a subject previously administered with genetically modified immune cells; or a subject that is CMV seropositive. In some other embodiments, the isolated immune cells for modulation are genetically modified (genetically engineered or naturally derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, the genetically modified immune cells are isolated for ex vivo modulation using the present compositions and methods as disclosed. In some embodiments, after modulation, the genetically modified immune cells isolated from a subject may be administered to the same donor or a different patient.

In some other embodiments, the immune cells suitable for modulating by said agents are differentiated in vitro from stem cells, hematopoietic stem or progenitor cells, or progenitor cells; or, are trans-differentiated in vitro from non-pluripotent cells of hematopoietic or non-hematopoietic lineage. In some embodiments, said stem cells comprise induced pluripotent stem cells (iPSCs) or embryonic stem cells (ESCs). In other embodiments, the progenitor cell is a CD34+ hemogenic endothelium cell, a multipotent progenitor cell, a T cell progenitor cell, a NK progenitor cell, or a NKT progenitor cell.

In some embodiments, the stem cell, hematopoietic stem or progenitor cell, or progenitor cell for differentiating various immune cells including T, NK, NKT cell is genomically engineered and comprises an insertion, a deletion, or a nucleic acid replacement; or comprises at least one genetically modified modality. As such the desired subpopulation of modulated immune cells that are derived from the stem cell, hematopoietic stem or progenitor cell, or progenitor cell also comprise at least one genetically modified modality. In one particular embodiment, the desired subpopulation of immune cells comprises CD57+ NK cells having at least one genetically modified modality. In some embodiments, the genetically modified modality comprises at least one of safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modalities comprise one or more of deletion or reduced expression of B2M, TAP1, TAP2, Tapasin, NLRC5, PD1, LAG3, TIM3, RFXANK, CIITA, RFX5, or RFXAP, and any gene in the chromosome 6p21 region. In some embodiments, the genetically modified modalities comprise one or more introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers. In one particular embodiment, the CD57+ NK cells comprised in the desired subpopulation obtained from immune cell modulation comprise expression of hnCD16. In another embodiment, the CD57+ NK cells expressing hnCD16, further comprise at least one of NKG2C+, low PLZF, low SYK, low FcεRγ, low EAT-2, low TIGIT, low PD1, low CD7, low CD161, high LILRB1, high CD45RO, and low CD45RA.

In some embodiments, the immune cells are modulated by a composition comprising a GSK3 inhibitor. In some embodiments, the composition comprising a GSK3 inhibitor further comprises at least one of the stimulating cytokines comprising IL2, IL15, IL12, IL18 and IL21. In some embodiments, the composition comprising a GSK3 inhibitor further comprises one or more of a MEK inhibitor, rapamycin, and a STING agonist. As such, in some embodiments, the composition comprises a population of NK cells, and a GSK3 inhibitor. In some embodiments, the composition comprises a population of NK cells, a GSK3 inhibitor, and IL15. In some other embodiments, the composition comprises a population of NK cells, a GSK3 inhibitor, IL15, and a STING agonist. In some embodiments, the immune cells are modulated by a composition comprising a modulator and at least one organic solvent selected from the group consisting of dimethyl sulfoxide (DMSO), N,N-dimethylformamide (DMF), dimethoxyethane (DME), dimethylacetamide, ethanol and combinations thereof.

Still, another aspect of the invention provides a composition comprising an isolated population of immune cells that has been contacted or modulated with a composition comprising one or more agents listed in Table 1, or a derivative or an analogue thereof. In some embodiments, the composition provided is a therapeutic composition having the treated isolated population or subpopulation of immune cells including, but not limited to, T, NK, and NKT cells. The therapeutic composition can be washed with a buffer substantially free of the modulating agent.

In some embodiments, the modulated cell population comprises immune cells having improved therapeutic potential for adoptive cell therapy in comparison to unmodulated cell population. In some embodiments, the isolated population of immune cells has improved cell expansion, maintenance, differentiation, dedifferentiation, and/or survival rate in comparison to immune cells without the treatment by the one or more agents. In some embodiments, the isolated population of immune cells has improved cell proliferation, cytotoxicity, cytokine response and secretion, cell recall, and persistence in comparison to immune cells without the treatment by the one or more agents. In some other embodiments, the isolated population of immune cells has increased number or ratio of one or more desired subpopulations of the immune cells in comparison to immune cells without the same treatment.

In some embodiments, the isolated population of immune cells that treated with one or more agents selected from the group consisting of compounds listed in Table 1 comprises T cells, as such the obtained one or more desired subpopulation of immune cells comprise naïve T cells, stem cell memory T cells, and/or central memory T cells. In some embodiments, the isolated population of immune cells treated with one or more agents comprises NKT cells, as such the obtained one or more desired subpopulation of immune cells comprise type I NKT cells. In yet some other embodiments, the isolated population of immune cells treated with one or more agents comprises NK cells, as such the one or more desired subpopulation of immune cells comprise adaptive NK cells.

In some embodiments of the composition as provided, the isolated population of immune cells may be isolated from peripheral blood, bone marrow, lymph node tissue, cord blood, thymus tissue, tissue from a site of infection, ascites, pleural effusion, spleen tissue, or tumors of a subject. The subject may be healthy, may have an autoimmune disease, a hematopoietic malignancy, a virus infection or a solid tumor, or may have been previously administered with genetically modified immune cells. In some embodiments, the subject may be CMV seropositive. In some other embodiments, the isolated immune cells for modulation are genetically modified (genetically engineered or naturally derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, the genetically modified immune cells are isolated for ex vivo modulation using the present compositions and methods as disclosed. In some embodiments, after modulation, the genetically modified immune cells isolated from a subject may be administered to the same donor or a different patient.

In some embodiments of the composition as provided, the isolated population of immune cells may be differentiated from a stem cell, a hematopoietic stem or progenitor cell, or a progenitor cell. In some embodiments, the isolated population of immune cells may be differentiated from a stem cell, a hematopoietic stem or progenitor cell, or a progenitor cell prior to, or during, the treatment by the agent(s). In some embodiments, the stem cell is an induced pluripotent stem cell (iPSC) or embryonic stem cell (ESC). In some embodiments, the progenitor cell is a CD34+ hemogenic endothelium cell, a multipotent progenitor cell, a T cell progenitor cell, a NK progenitor cell, or a NKT progenitor cell. In some further embodiment, the stem cell, hematopoietic stem or progenitor cell, progenitor, the derived immune cell for modulation, or modulated derived immune cell is genomically engineered, for example, comprising an insertion, a deletion, and/or a nucleic acid replacement. In one particular embodiment, the stem cell, hematopoietic stem or progenitor cell, or progenitor comprises an exogenous nucleic acid encoding a T Cell Receptor (TCR), a Chimeric Antigen Receptor (CAR), and/or overexpression of CD16.

In some other embodiment of the composition as provided, the isolated population of immune cells may be trans-differentiated from a non-pluripotent cell of hematopoietic or non-hematopoietic lineage. In some embodiments, the isolated population of immune cells may be trans-differentiated from a non-pluripotent cell of hematopoietic or non-hematopoietic lineage prior to, or during, the treatment by the agent.

Another aspect of the present invention provides a method of modulating immune cells, comprising contacting the immune cells with a sufficient amount of a composition comprising at least one agent selected from the group consisting of the compounds listed in Table 1, and derivatives and analogues thereof, for a time sufficient to obtain a population of modulated immune cells having improved therapeutic potential for adoptive cell therapy in comparison to unmodulated immune cells. In some embodiments, the derivatives and analogues comprise salt, ester, ether, solvate, hydrate, stereoisomer, and prodrug of the agents of Table 1.

In some embodiments of said method, the modulated immune cells comprise cells have improved proliferation, cytotoxicity, cytokine response, cytokine release, cell recall, and/or persistence; improved cell expansion, maintenance, differentiation, dedifferentiation, and/or survival rate; and/or increased number or ratio of one or more desired subpopulations of immune cells, in comparison to immune cells not contacted with the one or more agents of Table 1. In some embodiments of said method, the method further comprises isolating the one or more desired subpopulations from the modulated immune cells. In one embodiment, the immune cells for modulation comprise T cells, NKT cells, or NK cells. In another embodiment, the NK cells for modulation comprise CD57− NK cells, or CD57−NKG2C+ NK cells. After immune cell modulation using said method, in one embodiment, the one or more desired subpopulations in the modulated immune cells may comprise naïve T cells, stem cell memory T cells, and/or central memory T cells; type I NKT cells; or CD57+ NK cells. In one embodiment, the CD57+ NK cells obtained after modulation comprise adaptive NK cells. In some embodiments, the adaptive NK cells are characterized by CD57+ and at least one of NKG2C+, low PLZF, low SYK, low FcεRγ, low EAT-2, low TIGIT, low PD1, low CD7, low CD161, high LILRB1, high CD45RO, and low CD45RA.

In some embodiments of said general method, the immune cells for modulation are isolated from or comprised in peripheral blood, bone marrow, lymph node tissue, cord blood, thymus tissue, tissue from a site of infection, ascites, pleural effusion, spleen tissue, or tumors. In some embodiments, the immune cells for modulation are isolated from a healthy subject; a subject having an autoimmune disease, a hematopoietic malignancy, a virus infection or a solid tumor; a subject previously administered with genetically modified immune cells; or a subject that is CMV seropositive. In some other embodiments, the isolated immune cells for modulation are genetically modified (genetically engineered or naturally derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, the genomically modified immune cells are isolated for ex vivo modulation using the present compositions and methods as disclosed. In some embodiments, after modulation, the genomically modified immune cells isolated from a subject may be administered to the same donor or a different patient.

In some embodiments, the immune cells for modulation are differentiated in vitro from stem cells, hematopoietic stem or progenitor cells, or progenitor cells. In some embodiments, the immune cells for modulation are trans-differentiated in vitro from non-pluripotent cells of hematopoietic or non-hematopoietic lineage. In some embodiments, said stem cells comprise induced pluripotent stem cells (iPSCs) or embryonic stem cells (ESCs). In some embodiments, said progenitor cell is a CD34+ hemogenic endothelium cell, a multipotent progenitor cell, a T cell progenitor cell, a NK progenitor cell, or a NKT progenitor cell. In yet some other embodiments, the stem cell, hematopoietic stem or progenitor cell, or progenitor cell is genomically engineered and comprises an insertion, a deletion, or a nucleic acid replacement, and/or comprises at least one genetically modified modality. As such, the desired subpopulation of modulated immune cells derived therefrom comprises immune cells having at least one genetically modified modality. In one embodiment, the desired subpopulation of immune cells comprises CD57+ NK cells having at least one genetically modified modality.

In some embodiments, said genetically modified modality comprises at least one of safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modalities comprise one or more of deletion or reduced expression of B2M, TAP1, TAP2, Tapasin, NLRC5, PD1, LAG3, TIM3, RFXANK, CIITA, RFX5, or RFXAP, and any gene in the chromosome 6p21 region. In some other embodiments, the genetically modified modalities comprise one or more introduced or increased expression of HLA-E, HLA-G HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers. In one embodiment, the CD57+ NK cells comprised in a desired subpopulation of modulated immune cell comprise expression of hnCD16. In another embodiment, the CD57+ NK cells expressing hnCD16 further comprise at least one of NKG2C+, low PLZF, low SYK, low FcεRγ, low EAT-2, low TIGIT, low PD1, low CD7, low CD161, high LILRB1, high CD45RO, and low CD45RA.

In some embodiments of said method of modulating immune cells, the composition comprises a GSK3 inhibitor as a modulator. In some embodiments, the composition further comprises at least one of the stimulating cytokines comprising IL2, IL15, IL12, IL18 and IL21. In some embodiments, the composition comprising a GSK3 inhibitor further comprises one or more of a MEK inhibitor, rapamycin, and a STING agonist. In some embodiments, the composition comprising a modulator further comprises at least one organic solvent selected from the group consisting of dimethyl sulfoxide (DMSO), N,N-dimethylformamide (DMF), dimethoxyethane (DME), dimethylacetamide, ethanol and combinations thereof.

In some embodiments of the method of modulating immune cells, said "time sufficient" or "sufficient length of time" is no less than 16 hours, 14 hours, 12 hours, 10 hours, 8 hours, 6 hours, 4 hours, 2 hours, or any length of time in between. As such, said sufficient length of time, for example, is no less than 15, 13, 11, 9, 7, 5, 3, or 1 hour(s). In some other embodiments of the method, said sufficient length of time is no less than 24 hours, 36 hours, 48 hours, 60 hours, 72 hours, or any length of time in between. As such, said sufficient length of time is, for example, no less than 30, 42, 54, 66, 78, 90 hour(s).

In some embodiments of said method, the immune cells, during and/or after modulation, are in a feeder-free environment. Feeder-free conditions include feeder cell free, and feeder-conditioned medium free. In some embodiments of said method, the immune cells, during modulation, are co-cultured with feeder cells.

Another aspect of the present invention provides a method of modulating immune cells, which method comprises contacting the immune cells with a sufficient amount of a composition comprising a GSK3 inhibitor for a time sufficient to obtain a population of modulated immune cells having improved therapeutic potential for adoptive cell therapy in comparison to unmodulated immune cells.

A further aspect of the invention provides a method of modulating NK cells, which method comprises contacting the NK cells with a sufficient amount of a composition comprising a GSK3 inhibitor for a time sufficient to obtain modulated NK cells having improved therapeutic potential for adoptive cell therapy in comparison to unmodulated NK cells. In some embodiments of said general method, the modulated NK cells have improved proliferation, cytotoxicity, cytokine response, cytokine release, cell recall, and/or persistence. In some embodiments, the modulated NK cells have improved cell expansion, maintenance, differentiation, dedifferentiation, and/or survival rate. In some embodiments, the modulated NK cells have increased number or ratio of one or more desired subpopulations of NK cells in comparison to NK cells not contacted with the composition comprising the GSK3 inhibitor. In some embodiments, the improved properties of the modulated NK cells are in vitro. In some embodiments, the improved properties of the modulated NK cells are in vivo. In some embodiments, the NK cells for modulation comprise CD57− NK cells. In some embodiments, the NK cells for modulation comprise CD57− NKG2C+ NK cells.

In one embodiment of the method of modulating NK cells with GSK3 inhibitor, the method further comprises isolating the one or more desired subpopulations from the modulated NK cells. In some embodiments, the one or more desired subpopulations of NK cells comprise CD57+ NK cells. In some embodiments, the CD57+ NK cells comprise adaptive NK cells. In some embodiments, the adaptive NK cells comprise CD57+ and at least one of NKG2C+, low PLZF, low SYK, low FcεRγ, low EAT-2, low TIGIT, low PD1, low CD7, low CD161, high LILRB1, high CD45RO, and low CD45RA.

In some embodiment of said method of modulating NK cells, the NK cells for modulation are isolated from or comprised in peripheral blood, bone marrow, lymph node tissue, cord blood, thymus tissue, tissue from a site of infection, ascites, pleural effusion, spleen tissue, or tumors. In one embodiment, the NK cells are isolated from a healthy subject. In another embodiment, the NK cells are isolated from a subject having an autoimmune disease, a hematopoietic malignancy, a virus infection or a solid tumor. In one embodiment, the NK cells are isolated from a subject previously administered with genetically modified immune cells; In yet another embodiment, the NK cells for modulation are isolated from a subject that is CMV seropositive. In some other embodiments, the isolated immune cells for modulation are genetically modified (genetically engineered or naturally derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, the genetically modified immune cells are isolated for ex vivo modulation using the present compositions and methods as disclosed. In some embodiments, after modulation, the genetically modified immune cells isolated from a subject may be administered to the same donor or a different patient.

In some other embodiments, the NK cells for modulation are genomically engineered and comprise an insertion, a deletion, or a nucleic acid replacement. In one embodiment, the NK cells for modulation comprise at least one genetically modified modality. In another embodiment, the NK cells for modulation are differentiated in vitro from stem cells, hematopoietic stem or progenitor cells, or progenitor cells; or are trans-differentiated in vitro from non-pluripotent cells of hematopoietic or non-hematopoietic lineage. In some embodiments, above said stem cells comprise induced pluripotent stem cells (iPSCs) or embryonic stem cells (ESCs). In some embodiments, said progenitor cell is a CD34+ hemogenic endothelium cell, a multipotent progenitor cell, or a NK progenitor cell. In some particular embodiments, above said stem cell, hematopoietic stem or progenitor cell, or progenitor cell is genomically engineered and comprises an insertion, a deletion, or a nucleic acid replacement. In one embodiment, above said stem cell, hematopoietic stem or progenitor cell, or progenitor cell comprises at least one genetically modified modality. Said stem cell, hematopoietic stem or progenitor cell, or progenitor cell comprising at least one genetically modified modality may be used to derive differentiated immune cells including NK cells.

In one embodiment, the desired subpopulation of modulated and derived NK cells comprises NK cells having at least one genetically modified modality. In one embodiment, the desired subpopulation of modulated NK cells comprises CD57+ NK cells having at least one genetically modified modality. In some embodiments, the genetically modified modality comprises at least one of safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modalities comprise one or more of (i) deletion or reduced expression of B2M, TAP1, TAP2, Tapasin, NLRC5, PD1, LAG3, TIM3, RFXANK, CIITA, RFX5, or RFXAP, and any gene in the chromosome 6p21 region; and (ii) introduced or increased expression of HLA-E, HLA-G HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers. In one particular embodiment, the CD57+ NK cells comprise expression of hnCD16. In another embodiment, the CD57+ NK cells expressing hnCD16 further comprise at least one of NKG2C+, low PLZF, low SYK, low FcεRγ, low EAT-2, low TIGIT, low PD1, low CD7, low CD161, high LILRB1, high CD45RO, and low CD45RA.

In some embodiment of the method, the composition comprising GSK3 inhibitor further comprises at least one of the stimulating cytokines comprising IL2, IL15, IL12, IL18 and IL21. In one embodiment, the composition comprising GSK3 inhibitor further comprises one or more of a MEK inhibitor, rapamycin, and a STING agonist. In some embodiment of the method, the composition comprising GSK3 inhibitor further comprises at least one organic solvent selected from the group consisting of dimethyl sulfoxide (DMSO), N,N-dimethylformamide (DMF), dimethoxyethane (DME), dimethylacetamide, ethanol and combinations thereof.

In some embodiments, the GSK3 inhibitor is CHIR99021, BIO, TWS119, or Kenpaullone. In one embodiment, the GSK3 inhibitor is CHIR99021. In some embodiments, the time sufficient for GSK3 inhibitor modulation is no less than 16 hours. In some embodiments, the modulated NK cell have increased expansion by at least 2 fold. In some other embodiments, the modulated NK cell have increased production of one or more cytokines comprising IFNγ and/or TNFα. In yet some other embodiments, the one or more subpopulations of the NK cells having increased number or ratio comprise adaptive NK cells; NK cells expressing CD57; or cells expressing CD57 and NKG2C. In one embodiment, this method is carried out in a feeder-free environment. In some embodiments of said method, the immune cells, during modulation, are co-cultured with feeder cells.

Also provided is a method of culturing a population of immune cells, comprising contacting the population with a composition comprising a GSK3 inhibitor to obtain selectively expanded NK cells in the population. The method further comprises obtaining a population of immune cells from a subject prior to contacting the immune cells with the composition comprising the GSK3 inhibitor, wherein the immune cells comprise peripheral blood mononuclear cells; and depleting CD3 and CD19 cells from the population of peripheral blood mononuclear cells. In some embodiments, the subject is healthy; is a subject having an autoimmune disease, a hematopoietic malignancy, a virus infection or a solid tumor; or is a subject that is CMV seropositive, or may have been previously administered with genetically modified immune cells. In some embodiments, the expanded NK cells have improved cytotoxicity and cytokine response and secretion; have improved proliferation, cell recall, and/or persistence; have improved cell expansion, and/or maintenance; have increased subtype-skewing towards maturation; have increased number or ratio of one or more subpopulations in the cell population; and/or maintain the adaptive/memory cell like state, when compared to NK cells not contacted with the composition comprising the GSK3 inhibitor. In some embodiments, the modulated NK cells have increased expansion by at least 2 fold. In some other embodiments, the modulated NK cell have increased production of one or more cytokines comprising IFNγ and/or TNFα. In yet some other embodiments, the one or more subpopulations of the NK cells having increased number or ratio comprise adaptive NK cells; NK cells expressing CD57; or cells expressing CD57 and NKG2C. In one embodiment, this method is carried out in a feeder-free environment. In some embodiments, this method is carried out comprising co-culturing with feeder cells. In some other embodiments, the composition comprising the GSK3 inhibitor further comprises one or more of IL15, IL12, IL18, a MEK inhibitor, and rapamycin. In one embodiment, the GSK3 inhibitor is CHIR999021.

Further provided is a composition comprising a population of immune cells, and a composition comprising a GSK3 inhibitor, wherein the population comprises immune cells having improved therapeutic potential of immune cells for adoptive cell therapy upon modulating the population with the composition comprising the GSK3 inhibitor.

Still another aspect of the application provides a method of modulating adaptive NK cells, which comprises contacting a population of immune cells comprising adaptive NK cells with a sufficient amount of a composition comprising a GSK3 inhibitor for a time sufficient to obtain a population of modulated adaptive NK cells. Said method may further comprise obtaining a population of immune cells from a subject, and depleting CD3 and/or CD19 cells from the obtained population of immune cells prior to contacting the immune cells with the composition comprising the GSK3 inhibitor. In some embodiments, the method further comprises activating the population of immune cells before or during the step of contacting the immune cells with the composition comprising the GSK3 inhibitor. In some embodiments, the modulated adaptive NK cells have: improved cytotoxicity and cytokine response and secretion; improved proliferation, cell recall, and/or persistence; and/or improved cell expansion, and/or maintenance; in comparison to adaptive NK cells not contacted with the composition comprising the GSK3 inhibitor. In some embodiments, the modulated adaptive NK cells comprised in the population of immune cells have increased expansion by at least 2 fold after contacting the composition comprising the GSK3 inhibitor. In one embodiment, this method is carried out in a feeder-free environment. In one embodiment, this method is carried out with feeder cells. In some other embodiments, the composition comprising the GSK3 inhibitor further comprises one or more of IL15, IL12, IL18, IL21, a MEK inhibitor, rapamycin, and a STING agonist. In one embodiment, the GSK3 inhibitor is CHIR999021. Also provided is a population of modulated NK cells having increased expression in one or more of CD107a, NKG2C, NKG2D, CD16, KIR, CD2, NKp30, NKp44 and NKp46 in comparison to unmodulated NK cells, wherein the expression thereof is increased by at least 10%, 20%, 30%, 40%, 50%, 60%, 70%, 80%, 90%, 100% or above.

A further aspect of the present invention provides using the above immune cell modulation methods to make therapeutic compositions comprising modulated immune cells for cell therapies. In some embodiment, the modulated immune cells comprise T, NK and/or NKT cells. In some embodiments, the modulated NK cells comprise adaptive NK cells. An additional aspect of the present invention provides a population of modulated immune cells comprising selectively expanded NK cells made by the method provided herein.

Yet another aspect of the present invention provides a therapeutic composition comprising the modulated cells obtained using the methods and composition disclosed herein, and a therapeutically acceptable medium. In some embodiments of the therapeutic composition, the composition further comprises one of more additional additives selected from the group consisting of peptides, cytokines, mitogens, growth factors, small RNAs, dsRNAs (double stranded RNAs), mononuclear blood cells, feeder cells, feeder cell components or replacement factors, vectors comprising one or more polynucleic acids of interest, antibodies, chemotherapeutic agents or radioactive moiety, and immunomodulatory drugs (IMiDs).

Further provided is a method of treating a subject by administering a therapeutically sufficient amount of the above said therapeutic composition to a subject in need of an adoptive cell therapy. In some embodiments, the cell therapy is autologous. In some other embodiments, the cell therapy is allogeneic. In some embodiments, the subject in need of the therapy has an autoimmune disorder, a hematological malignancy, a solid tumor, cancer, or an infection associated with HIV, RSV, EBV, CMV, adenovirus, or BK polyomavirus. In some embodiments, the method of treating a subject using the modulated immune cells is carried out by administering said therapeutic composition in combination with an antibody, a chemotherapeutic, or a radioactive treatment, wherein the antibody, chemotherapeutic, or radioactive treatment is prior to, during or after administering the therapeutic composition.

Still another aspect of the present invention provides the use of a mixture for manufacturing of a therapeutic composition for cell therapies according to methods provided herein, and the mixture for manufacturing comprises an isolated population of immune cells, and a composition for immune cell modulation comprising a GSK3 inhibitor, Various objects and advantages of this use will become apparent from the following description taken in conjunction with the accompanying drawings wherein are set forth, by way of illustration and example, certain embodiments of this invention.

BRIEF DESCRIPTION OF THE DRAWINGS

FIG. 4 is a graphic representation showing that GSK inhibition is the key reagent in the 7 day culture that efficiently augments NK cell expansion, skewing the population towards adaptive (NKG2C+/CD57+) and total CD57+ subsets. A. Fold increase in cell numbers. B. Percentage of cells.

FIG. 11 shows that GSK3 inhibitor treatment does not lead to a higher frequency of CD56+CD57+ cells in short term. A. CD57+ NK fraction in 16-hour culture with and without GSK3 inhibitor. B. CD57+ NK fraction in 0-7 day culture with and without GSK3 inhibitor.

DETAILED DESCRIPTION OF THE INVENTION

Figure 1:
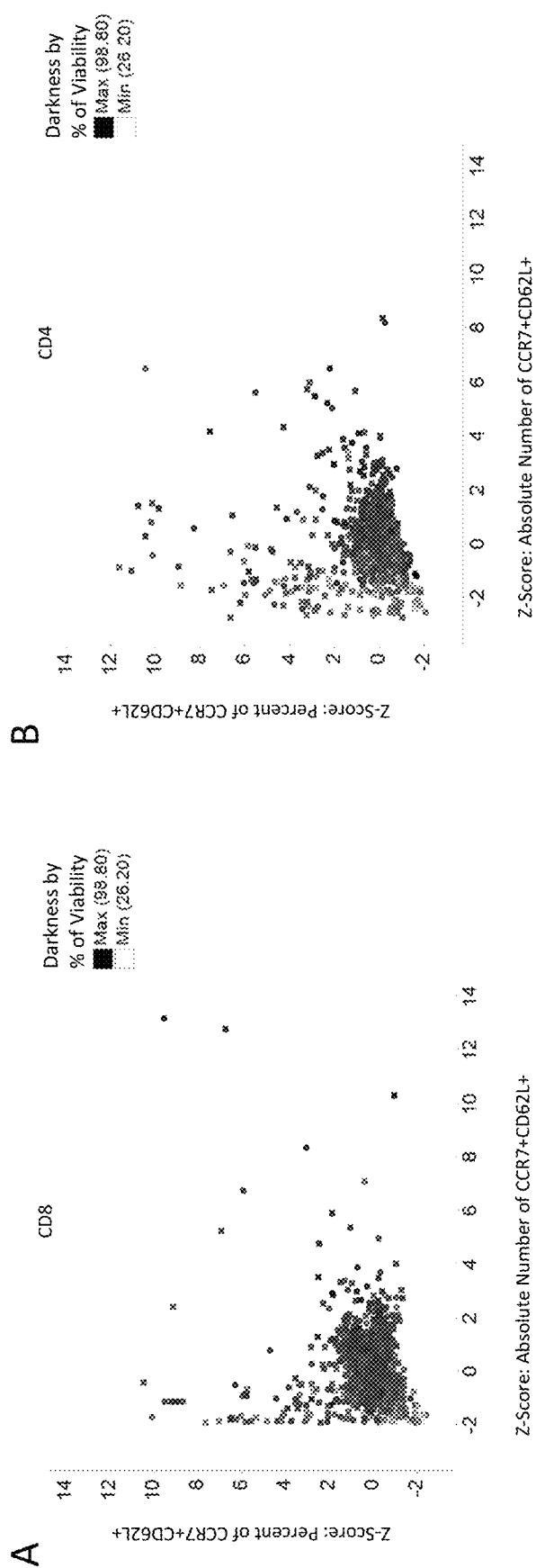
FIG. 1 is a graphic representation of z-Score of the percentage of cells co-expressing both of CCR7 and CD62L, and a relative measure of the absolute number of naïve, stem cell memory, or central memory T cells in (A) the viable CD8+ cell population and (B) the viable CD4+ cell population.

The present invention provides compositions and methods of modulating immune cell populations or subpopulations to obtain improved therapeutic potential for adoptive immunotherapies. The present invention also provides the method of using the modulated immune cells having improved therapeutic potential. In general, immune cells having improved therapeutic potential exhibit at least one of the following: improved proliferation, persistence, cytotoxicity, and/or cell recall/memory. The invention provides methods of improving immune cell therapeutic potential through improvements to the quality of the immune cells—for example, an increase in the number or ratio of a subpopulation of cells that displays improvement in at least one of the following qualities would be expected to result in better immunotherapeutic results: migration, homing, cytotoxicity, maintenance, expansion, persistence, longevity, differentiation, and/or de-differentiation of the same cells.

Definition

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein, the articles "a," "an," and "the" refer to one or to more than one of the grammatical object of the article. By way of example, a T cell means one T cell or more than one T cells.

As used herein, the terms "T lymphocyte" and "T cell" are used interchangeably and refer to a principal type of white blood cell that completes maturation in the thymus and that has various roles in the immune system, including the identification of specific foreign antigens in the body and the activation and deactivation of other immune cells. A T cell can be any T cell, such as a cultured T cell, e.g., a primary T cell, or a T cell from a cultured T cell line, e.g., Jurkat, SupT1, etc., or a T cell obtained from a mammal. The T cell can be CD3+ cells. The T cell can be any type of T cell and can be of any developmental stage, including but not limited to, CD4+/CD8+ double positive T cells, CD4+ helper T cells (e.g., Th1 and Th2 cells), CD8+ T cells (e.g., cytotoxic T cells), peripheral blood mononuclear cells (PBMCs), peripheral blood leukocytes (PBLs), tumor infiltrating lymphocytes (TILs), memory T cells, naïve T cells, regulator T cells, gamma delta T cells (γδ T cells), and the like. Additional types of helper T cells include cells such as Th3, Th17, Th9, or Tfh cells. Additional types of memory T cells include cells such as central memory T cells (Tcm cells), effector memory T cells (Tem cells and TEMRA cells). The T cell can also refer to a genetically engineered T cell, such as a T cell modified to express a T cell receptor (TCR) or a chimeric antigen receptor (CAR). The T cell can also be differentiated from a stem cell or progenitor cell.

As used herein, the term "naïve T cell" or Tn, refers to mature T cells that, unlike activated or memory T cells, have not encountered their cognate antigen within the periphery. Naïve T cells are commonly characterized by the surface expression of L-selectin (CD62L); the absence of the activation markers CD25, CD44 or CD69; and the absence of the memory CD45RO isoform. They also express functional IL-7 receptors, consisting of subunits IL-7 receptor-α, CD127, and common-γ chain, CD132. In the naïve state, T cells are thought to be quiescent and non-dividing, requiring the common-gamma chain cytokines IL-7 and IL-15 for homeostatic survival mechanisms.

As used herein, the term "central memory T cells" or Tcm, refers to a subgroup or subpopulation of T cells that have lower expression or pro-apoptotic signaling genes, for example, Bid, Bnip3 and Bad, and have higher expression of genes associated with trafficking to secondary lymphoid organs, which genes include CD62L, CXCR3, CCR7, in comparison to effector memory T cells, or Tem.

As used herein, the term "stem memory T cells," or "stem cell memory T cells", or Tscm, refers to a subgroup or subpopulation of T cells that are capable of self-renewing and generating Tcm, Tem and Teff (effector T cells), and express CD27 and lymphoid homing molecules such as CCR7 and CD62L, which are properties important for mediating long-term immunity.

As used herein, the term "NK cell" or "Natural Killer cell" refer to a subset of peripheral blood lymphocytes defined by the expression of CD56 or CD16 and the absence of the T cell receptor (CD3). As used herein, the terms "adaptive NK cell" and "memory NK cell" are interchangeable and refer to a subset of NK cells that are phenotypically CD3− and CD56+, and have at least one of CD57+, NKG2C+, low PLZF, low SYK, low FcεRγ, low EAT-2, low TIGIT, low PD1, low CD7, low CD161, high LILRB1, high CD45RO, and low CD45RA. In some embodiments, isolated subpopulations of CD56+ NK cells comprise expression of NKG2C and CD57. In some other embodiments, isolated subpopulations of CD56+ NK cells comprise expression of CD57, CD16, NKG2C, CD57, NKG2D, NCR ligands, NKp30, NKp40, NKp46, activating and inhibitory KIRs, NKG2A and/or DNAM-1. CD56+ can be dim or bright expression.

As used herein, the term "NKT cells" or "natural killer T cells" refers to CD1d-restricted T cells, which express a T cell receptor (TCR). Unlike conventional T cells that detect peptide antigens presented by conventional major histocompatibility (MHC) molecules, NKT cells recognize lipid antigens presented by CD1d, a non-classical MHC molecule. Two types of NKT cells are currently recognized. Invariant or type I NKT cells express a very limited TCR repertoire—a canonical α-chain (Vα24-Jα18 in humans) associated with a limited spectrum of β chains (Vβ11 in humans). The second population of NKT cells, called non-classical or noninvariant type II NKT cells, display a more heterogeneous TCR αβ usage. Type I NKT cells are currently considered suitable for immunotherapy. Adaptive or invariant (type I) NKT cells can be identified with the expression of at least one or more of the following markers, TCR Va24-Ja18, Vb11, CD1d, CD3, CD4, CD8, aGalCer, CD161 and CD56.

As used herein, the term "isolated" or the like refers to a cell, or a population of cells, which has been separated from its original environment, i.e., the environment of the isolated cells is substantially free of at least one component as found in the environment in which the "un-isolated" reference cells exist. The term includes a cell that is removed from some or all components as it is found in its natural environment, for example, tissue, biopsy. The term also includes a cell that is removed from at least one, some or all components as the cell is found in non-naturally occurring environments, for example, culture, cell suspension. Therefore, an isolated cell is partly or completely separated from at least one component, including other substances, cells or cell populations, as it is found in nature or as it is grown, stored or subsisted in non-naturally occurring environments. Specific examples of isolated cells include partially pure cells, substantially pure cells and cells cultured in a medium that is non-naturally occurring. Isolated cells may be obtained from separating the desired cells, or populations thereof, from other substances or cells in the environment, or from removing one or more other cell populations or subpopulations from the environment. As used herein, the term "purify" or the like refers to increasing purity. For example, the purity can be increased to at least 50%, 60%, 70%, 80%, 90%, 95%, 99%, or 100%.

As used herein, the term "population" when used with reference to T, NK or NKT cells refers to a group of cells including two or more T, NK, or NKT cells, respectively. Using T cell as an example, the isolated, or enriched, population of T cells may include only one type of T cell, or may include a mixture of two or more types of T cell. The isolated population of T cells can be a homogeneous population of one type of T cell or a heterogeneous population of two or more types of T cell. The isolated population of T cells can also be a heterogeneous population having T cells and at least a cell other than a T cell, e.g., a B cell, a macrophage, a neutrophil, an erythrocyte, a hepatocyte, an endothelial cell, an epithelial cell, a muscle cell, a brain cell, etc. The heterogeneous population can have from 0.01% to about 100% T cell. Accordingly, an isolated population of T cells can have at least 50%, 60%, 70%, 80%, 90%, 95%, 98%, or 99% T cells. The isolated population of T cells can include one or more, or all of, the different types of T cells, including but not limited to those disclosed herein. In an isolated population of T cells that includes more than one type of T cells, the ratio of each type of T cell can range from 0.01% to 99.99%. The isolated population also can be a clonal population of T cells, in which all the T cells of the population are clones of a single T cell.

An isolated population of T, NK or NKT cells may be obtained from a natural source, such as human peripheral blood or cord blood. Various ways of dissociating cells from tissues or cell mixtures to separate the various cell types have been developed in the art. In some cases, these manipulations result in a relatively homogeneous population of cells. The T cells can be isolated by a sorting or selection process as described herein or by other methods known in the art. The proportion of T cells in the isolated population may be higher than the proportion of T cells in the natural source by at least about 10%, about 20%, about 30%, about 40%, about 50%, about 60%, about 70%, about 80%, about 85%, about 90%, or about 95%. The isolated population of T cells can be for T cells in general, or one or more specific types of T cells.

As used herein, the term "subpopulation" when used in reference to T, NK or NKT cells refers to a population of T, NK or NKT cells that includes less than all types of T, NK, or NKT cells, respectively, that are found in nature.

As used herein, the term "pluripotent" refers to the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

As used herein, the term "induced pluripotent stem cells" or, "iPSCs," refers to stem cells produced from differentiated adult cells that have been induced or changed (i.e. reprogrammed) into cells capable of differentiating into tissues of all three germ or dermal layers: mesoderm, endoderm, and ectoderm.

As used herein, the term "embryonic stem cell" refers to naturally occurring pluripotent stem cells of the inner cell mass of the embryonic blastocyst. Embryonic stem cells are pluripotent and give rise during development to all derivatives of the three primary germ layers: ectoderm, endoderm and mesoderm. They do not contribute to the extra-embryonic membranes or the placenta and are not totipotent.

As used herein, the term "progenitor cell" refers to cells that have greater developmental potential, i.e., a cellular phenotype that is more primitive (e.g., is at an earlier step along a developmental pathway or progression) relative to a cell which it can give rise to by differentiation. Often, progenitor cells have significant or very high proliferative potential. Progenitor cells can give rise to multiple distinct cells having lower developmental potential, i.e., differentiated cell types, or to a single differentiated cell type, depending on the developmental pathway and on the environment in which the cells develop and differentiate.

As used herein, the terms "reprogramming" or "dedifferentiation" or "increasing cell potency" or "increasing developmental potency" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "differentiation" is the process by which an unspecialized ("uncommitted") or less specialized cell acquires the features of a specialized cell such as, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type.

As used herein, the term "encoding" refers to the inherent property of specific sequences of nucleotides in a polynucleotide, such as a gene, a cDNA, or a mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "exogenous" in intended to mean that the referenced molecule or the referenced activity is introduced into the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell. Similarly, the term when used in reference to expression of an encoding nucleic acid refers to expression of an encoding nucleic acid contained within the cell and not exogenously introduced.

As used herein, the term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. Polynucleotide also refers to both double- and single-stranded molecules.

As used herein, the term "peptide," "polypeptide," and "protein" are used interchangeably and refer to a molecule having amino acid residues covalently linked by peptide bonds. A polypeptide must contain at least two amino acids, and no limitation is placed on the maximum number of amino acids of a polypeptide. As used herein, the terms refer to both short chains, which are also commonly referred to in the art as peptides, oligopeptides and oligomers, for example, and to longer chains, which generally are referred to in the art as polypeptides or proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural polypeptides, recombinant polypeptides, synthetic polypeptides, or a combination thereof.

As used herein, the term "ex vivo" refers to activities that take place outside an organism, such as experimentation or measurements done in or on living tissue in an artificial environment outside the organism, preferably with minimum alteration of the natural conditions. The "ex vivo" procedures can involve living cells or tissues taken from an organism and cultured in a laboratory apparatus, usually under sterile conditions, and typically for a few hours or up to about 24 hours, but including up to 2 to 28 days, depending on the circumstances. Such tissues or cells can also be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo. Meanwhile, an "in vivo" activity takes place inside an organism, such as cell engraftment, cell homing, self-renewal of cells, and expansion of cells.

As used herein, the term "in vitro" refers to activities performed or taking place in a test tube, culture dish, or elsewhere outside a living organism.

As used herein, the terms "agent," "modulating agent," and "modulator" are used interchangeably herein to refer to a compound or molecule capable of modifying gene expression profile or a biological property of a cell including an immune cell. The agent can be a single compound or molecule, or a combination of more than one compound or molecule.

As used herein, the terms "contact," "treat," or "modulate," when used in reference to an immune cell, are used interchangeably herein to refer to culturing, incubating or exposing an immune cell with one or more of the agents disclosed herein.

As used herein, a "noncontacted" or an "untreated" cell is a cell that has not been treated, e.g., cultured, contacted, or incubated with an agent other than a control agent. Cells contacted with a control agent, such as DMSO, or contacted with another vehicle are examples of noncontacted cells.

As used herein, "feeder cells" or "feeders" are terms describing cells of one type that are co-cultured with cells of a second type to provide an environment in which the cells of the second type can grow, as the feeder cells provide stimulation, growth factors and nutrients for the support of the second cell type. The feeder cells are optionally from a different species as the cells they are supporting. For example, certain types of human cells, including stem cells, can be supported by primary cultures of mouse embryonic fibroblasts, or immortalized mouse embryonic fibroblasts. In another example, peripheral blood derived cells or transformed leukemia cells support the expansion and maturation of natural killer cells. The feeder cells may typically be inactivated when being co-cultured with other cells by irradiation or treatment with an anti-mitotic agent such as mitomycin to prevent them from outgrowing the cells they are supporting. Feeder cells may include endothelial cells, stromal cells (for example, epithelial cells or fibroblasts), and leukemic cells. Without limiting the foregoing, one specific feeder cell type may be a human feeder, such as a human skin fibroblast. Another feeder cell type may be mouse embryonic fibroblasts (MEF). In general, various feeder cells can be used in part to maintain pluripotency, direct differentiation towards a certain lineage, enhance proliferation capacity and promote maturation to a specialized cell types, such as an effector cell.

As used herein, a "feeder-free" (FF) environment refers to an environment such as a culture condition, cell culture or culture media which is essentially free of feeder or stromal cells, and/or which has not been pre-conditioned by the cultivation of feeder cells. "Pre-conditioned" medium refers to a medium harvested after feeder cells have been cultivated within the medium for a period of time, such as for at least one day. Pre-conditioned medium contains many mediator substances, including growth factors and cytokines secreted by the feeder cells cultivated in the medium. In some embodiments, a feeder-free environment is free of both feeder or stromal cells and is also not pre-conditioned by the cultivation of feeder cells.

As used herein, the term "analogue" refers to a chemical molecule that is similar to another chemical substance in structure and function, differing structurally by one single element or group, or more than one group (e.g., 2, 3, or 4 groups) if it retains the same chemical scaffold and function as the parental chemical. Such modifications are routine to persons skilled in the art, and include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), modifications to the level of saturation or unsaturation of side chains, and the addition of modified groups such as substituted phenyl and phenoxy. Analogues can also include conjugates, such as biotin or avidin moieties, enzymes such as horseradish peroxidase and the like, and including radio-labeled, bioluminescent, chemoluminescent, or fluorescent moieties. Also, moieties can be added to the agents described herein to alter their pharmacokinetic properties, such as to increase half-life in vivo or ex vivo, or to increase their cell penetration properties, among other desirable properties. Also included are prodrugs, which are known to enhance numerous desirable qualities of pharmaceuticals (e.g., solubility, bioavailability, manufacturing, etc.).

As used herein, the term "increase" refers to the ability of an agent to produce or cause a greater physiological response (i.e., downstream effects) in a cell, as compared to the response caused by either vehicle or a control molecule/composition, e.g., increased production of interleukin 4 or interleukin 10 by an isolated population of T cells. The increase can be an increase in gene expression as a result of increased signaling through certain cell signaling pathways. An "increased" amount is typically a statistically significant amount, and can include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) compared to the response produced by vehicle (the absence of an agent) or a control composition.

As used herein, the term "decrease" refers to the ability of an agent to produce or cause a lesser physiological response (i.e., downstream effects) in a cell, as compared to the response caused by either vehicle or a control molecule/composition. The decrease can be a decrease in gene expression, a decrease in cell signaling, or a decrease in cell proliferation. An "decreased" amount is typically a "statistically significant" amount, and can include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle (the absence of an agent) or a control composition.

As used herein, the term "synergy" or "synergistic" refers to a combination of two or more entities for an enhanced effect such that the working together of the two or more entities produces an effect greater than the sum of their individual effects, as compared to "antagonistic," which is used when two or more entities in a combination counteract or neutralize each other's effect, and compared to "additive," which is used when two or more entities in a combination produce an effect nearly equal to the sum of their individual effects.

As used herein, the terms "substantially free of," when used to describe a composition, such as a cell population or culture media, refers to a composition that is free of a specified substance of any source, such as, 95% free, 96% free, 97% free, 98% free, 99% free of the specified substance, or is undetectable as measured by conventional means. Similar meaning can be applied to the term "absence of," where referring to the absence of a particular substance or component of a composition.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. The range of quantity, level, value, number, frequency, percentage, dimension, size, amount, weight or length can be ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

As used herein, the term "subject," refers to a mammal. A subject can be a human or a non-human mammal such as a dog, cat, bovid, equine, mouse, rat, rabbit, or transgenic species thereof.

As used herein, the term "treat," and the like, when used in reference to a subject, refer to obtaining a desired pharmacologic and/or physiologic effect, including without limitation achieving an improvement or elimination of the symptoms of a disease. The effect can be prophylactic in terms of completely or partially preventing a disease or symptom thereof and/or can be therapeutic in terms of achieving an improvement or elimination of symptoms, or providing a partial or complete cure for a disease and/or adverse effect attributable to the disease. The term "treatment" includes any treatment of a disease in a mammal, particularly in a human, and includes: (a) preventing the disease from occurring in a subject which can be predisposed to the disease but has not yet been diagnosed as having it; (b) inhibiting the disease, or arresting its development; (c) relieving the disease, or causing regression of the disease, or to completely or partially eliminate symptoms of the disease; and (d) restoring the individual to a pre-disease state, such as reconstituting the hematopoietic system.

As used herein, "genetic modification" refers to genetic editing including those (1) naturally derived from rearrangements, mutations, genetic imprinting and/or epigenetic modification, (2) or obtained through genomic engineering through insertion, deletion or substitution in the genome of a cell. Genetic modification, as used herein, also includes one or more retainable therapeutic attributes of a source specific immune cell that is donor-, disease-, or treatment response-specific, As used herein, the term "genetic imprint" refers to genetic or epigenetic information that contributes to preferential therapeutic attributes in a source cell. In the aspect of a source cell obtained from a specifically selected donor, disease or treatment context, the genetic imprint contributing to preferential therapeutic attributes may include any context specific genetic or epigenetic modifications which manifest a retainable phenotype, i.e. a preferential therapeutic attribute, irrespective of the underlying molecular events being identified or not. Donor-, disease-, or treatment response-specific source cells may comprise genetic imprints that are retainable in iPSCs and derived hematopoietic lineage cells, which genetic imprints include but are not limited to, prearranged monospecific TCR, for example, from a viral specific T cell or invariant natural killer T (iNKT) cell; trackable and desirable genetic polymorphisms, for example, homozygous for a point mutation that encodes for the high-affinity CD16 receptor in selected donors; and predetermined HLA requirements, i.e., selected HLA-matched donor cells exhibiting a haplotype with increased population. As used herein, preferential therapeutic attributes include improved engraftment, trafficking, homing, viability, self-renewal, persistence, immune response regulation and modulation, survival, and cytotoxicity of a derived cell. A preferential therapeutic attribute may also relate to antigen targeting receptor expression; HLA presentation or lack thereof; resistance to tumor microenvironment; induction of bystander immune cells and immune modulations; improved on-target specificity with reduced off-tumor effect; resistance to treatment such as chemotherapy.

As used herein, the term "safety switch protein" refers to an engineered protein designed to prevent potential toxicity or otherwise adverse effects of a cell therapy. In some instances, the safety switch protein expression is conditionally controlled to address safety concerns for transplanted engineered cells that have permanently incorporated the gene encoding the safety switch protein into its genome. This conditional regulation could be variable and might include control through a small molecule-mediated post-translational activation and tissue-specific and/or temporal transcriptional regulation. The safety switch could mediate induction of apoptosis, inhibition of protein synthesis, DNA replication, growth arrest, transcriptional and post-transcriptional genetic regulation and/or antibody-mediated depletion. In some instance, the safety switch protein is activated by an exogenous molecule, e.g. a prodrug, that when activated, triggers apoptosis and/or cell death of a therapeutic cell. Examples of safety switch proteins, include, but are not limited to suicide genes such as caspase 9 (or caspase 3 or 7), thymidine kinase, cytosine deaminase, B-cell CD20, modified EGFR, and any combination thereof. In this strategy, a prodrug that is administered in the event of an adverse event is activated by the suicide-gene product and kills the transduced cell.

A "therapeutically sufficient amount", as used herein, includes within its meaning a non-toxic but sufficient and/or effective amount of the particular therapeutic and/or pharmaceutical composition to which it is referring to provide a desired therapeutic effect. The exact amount required will vary from subject to subject depending on factors such as the patient's general health, the patient's age and the stage and severity of the condition. In particular embodiments, a therapeutically sufficient amount is sufficient and/or effective to ameliorate, reduce, and/or improve at least one symptom associated with a disease or condition of the subject being treated.

I. Agents for Improving Efficacy of Cell-Based Adoptive Immunotherapy

The present invention provides a composition comprising one or more agents in an amount sufficient for improving therapeutic potential of immune cells suitable for adoptive cell-based therapies. Immune cells having improved therapeutic potential present improved proliferation, persistence, cytotoxicity, and/or cell recall/memory. Immune cells may have specifically improved in vivo proliferation, in vivo persistence, in vivo cytotoxicity, and/or in vivo cell recall/memory. To improve immune cell therapeutic potential generally requires better quality of the immune cells—in a T cell population, for example, increased number or ratio of naïve T cell, stem cell memory T cell, and/or central memory T cell through maintenance, expansion, differentiation, and/or de-differentiation thereof are indicative of better quality of the T cells for improved in vivo adoptive therapeutic potential. In a NK cell population, for example, increased number or ratio of adaptive NK cells through maintenance, subtype skewing, expansion, differentiation, and/or de-differentiation thereof are indicative of better quality of the NK cells for improved in vivo adoptive therapeutic potential. With respect to a NKT cell population, for example, an increased number or ratio of type I NKT cells through maintenance, subtype switching, expansion, differentiation, and/or de-differentiation thereof are indicative of better quality of the NKT cells for improved in vivo adoptive therapeutic potential.

The immune cells suitable for adoptive cell-based therapies are contacted, treated, or modulated with one or more agents included in Table 1. The treatment with the agent(s) can modify the biological properties of the cells, or a subpopulation of the cells, including by modulating cell expansion, maintenance, differentiation, dedifferentiation, and/or survival rate, and/or increasing proliferation, cytotoxicity, persistence, and/or cell recall/memory, and thus the therapeutic potential of the cells treated. For example, the treatment can improve the therapeutic immune cell survival rate both in vitro and in vivo. Further, the treatment can alter the ratios of different subpopulation of the treated cell population. For example, in one embodiment, the number and proportion of naïve T cells, stem cell memory T cells, and/or central memory T cells increase in an isolated T cell population upon treatment using one or more of the agents selected from Table 1. In another embodiment, upon treatment of a NK cell population using one or more of the agents selected from Table 1, the number and percentage of adaptive NK cells are increased in the population.

TABLE 1

| Agents for Immune Cell Modulation in Adoptive Cell Therapies | | | |
|---|---|---|---|
| Compounds | CAS Number | Group | Group Descriptor |
| Dorsomorphin | 866405-64-3 | I | Metabolism & Nutrient Sensing |
| Heptelidic acid | 74310-84-2 | I | Metabolism & Nutrient Sensing |
| 1-Pyrrolidinecarbodithioic acid, ammonium salt | 5108-96-3 | I | Metabolism & Nutrient Sensing |
| 2-dexoyglucose (2-DG) | 154-17-6 | I | Metabolism & Nutrient Sensing |
| GSK3 Inhibitor | Including for example-BIO: 667463-62-9; | II | Signaling Pathways |

TABLE 1-continued

Agents for Immune Cell Modulation in Adoptive Cell Therapies

| Compounds | CAS Number | Group | Group Descriptor |
|---|---|---|---|
| | TWS119: 601514-19-6; CHIR99021: 252917-06-9 | | |
| Rho kinase inhibitors | Including for example- Thiazovivin: 1226056-71-8 | II | Signaling Pathways |
| MEK inhibitors | Including for example- PD0325901: 391210-10-9; U0126: 109511-58-2 | II | Signaling Pathways |
| PDK1 agonist | Including for example- PS48: 1180676-32-7 | II | Signaling Pathways |
| TGFβ inhibitors | Including for example- SB431542: 301836-41-9 | II | Signaling Pathways |
| 6-Mercaptopurine | 6112-76-1 | II | Signaling Pathways |
| AC-93253 iodide | 108527-83-9 | II | Signaling Pathways |
| Tiratricol | 51-24-1 | II | Signaling Pathways |
| PI-103 | 371935-74-9 | II | Signaling Pathways |
| Fulvestrant | 129453-61-8 | II | Signaling Pathways |
| Thapsigargin | 67526-95-8 | II | Signaling Pathways |
| SU 4312 | 5812-07-7 | II | Signaling Pathways |
| Telmisartan | 144701-48-4 | II | Signaling Pathways |
| Cyclosporin A | 59865-13-3 | II | Signaling Pathways |
| 1,3,5-tris(4-hydroxyphenyl)-4-propyl-1H-pyrazole | 263717-53-9 | II | Signaling Pathways |
| BAY 61-3606 | 732983-37-8 | II | Signaling Pathways |
| Protoporphyrin IX disodium | 553-12-8 | II | Signaling Pathways |
| mTOR inhibitor | Including for example- Rapamycin: 53123-88-9 | II | Signaling Pathways |
| HS173 | 1276110-06-5 | II | Signaling Pathways |
| LY294002 | 154447-36-6 | II | Signaling Pathways |
| Pictilisib | 957054-30-7 | II | Signaling Pathways |
| 5-Azacytidine | 320-67-2 | III | Proliferation and Apoptosis |
| Fludarabine | 21679-14-1 | III | Proliferation and Apoptosis |
| Roscovitine, (S)-Isomer | 186692-45-5 | III | Proliferation and Apoptosis |
| PAC-1 | 315183-21-2 | III | Proliferation and Apoptosis |
| 8-Quinolinol, 5,7-dichloro- | 773-76-2 | IV | Anti-infective |
| Nitrofurantoin | 67-20-9 | IV | Anti-infective |
| 8-Quinolinol, 5-chloro-7-iodo- | 130-26-7 | IV | Anti-infective |
| 2-Naphthacenecarboxamide, 7-chloro-4-(dimethylamino)-1,4,4a,5,5a,6,11,12a-octahy | 64-73-3 | IV | Anti-infective |
| Nifuroxazide | 965-52-6 | IV | Anti-infective |
| Tosufloxacin hydrochloride | 100490-36-6 | IV | Anti-infective |
| Sertraline | 79617-96-2 | V | Other |
| Diethylenetriaminepentaacetic acid, penta sodium | 67-43-6 | V | Other |
| Edrophonium chloride | 116-38-1 | V | Other |
| BIX01294 | 1392399-03-9 | V | Other |
| Terfenadine | 50679-08-8 | V | Other |
| dmPGE2 (16,16-dimethyl Prostaglandin E2) | 39746-25-3 | V | Other |

Without being limited by the theory, the agents of Table 1 improve the therapeutic potential of an immune cell for adoptive therapy by modulating cell expansion, metabolism, and/or cell differentiation via regulating cell metabolism, nutrient sensing, proliferation, apoptosis, signal transduction, properties relating to infective process, and/or other aspects of cell function. As understood by those skilled in the art, the scope of the present invention also includes analogues or derivatives, including but not limited to, salt, ester, ether, solvate, hydrate, stereoisomer or prodrug of the listed agents in Table 1. For example, illustrative examples of analogues and derivatives of a Table 1 agent, dmPGE$_2$ (16,16-dimethyl Prostaglandin E2), include, without limitation, PGE$_2$, 16,16-dimethyl PGE$_2$ p-(p-acetamidobenzamido) phenyl ester, 11-deoxy-16,16-dimethyl PGE$_2$, 9-deoxy-9-methylene-16,16-dimethyl PGE$_2$, 9-deoxy-9-methylene PGE$_2$, 9-keto Fluprostenol, 5-trans PGE$_2$, 17-phenyl-omega-trinor PGE$_2$, PGE$_2$ serinol amide, PGE$_2$ methyl ester, 16-phenyl tetranor PGE$_2$, 15(S)-15-methyl PGE$_2$, 15(R)-15-methyl PGE$_2$, 8-iso-15-keto PGE$_2$, 8-iso PGE2 isopropyl ester, 8-iso-16-cyclohexyl-tetranor $PGE_2$, 20-hydroxy $PGE_2$, 20-ethyl $PGE_2$, 11-deoxy PGEi, nocloprost, sulprostone, butaprost, 15-keto $PGE_2$, and 19 (R) hydroxy $PGE_2$. Also included are PG analogues or derivatives having a similar structure to $PGE_2$ that are substituted with halogen at the 9-position (see, e.g., WO 2001/12596, the disclosure of which is hereby incorporated by reference in its entirety), as well as 2-decarboxy-2-phosphinico prostaglandin derivatives, such as those described in U.S. Publication No. 2006/0247214, the disclosure of which is hereby incorporated by reference in its entirety).

GSK3 (Glycogen synthase kinase 3) inhibitors can include antibodies that bind, dominant negative variants of, and siRNA, microRNA, antisense nucleic acids, and other polynucleotides that target GSK3. Suitable GSK3 inhibitor (GSK3i) for use in compositions contemplated herein include, but are not limited to: Kenpaullone; 1-Azakenpaullone; CHIR99021; CHIR98014; AR-A014418; CT 99021; CT 20026; SB216763; AR-A014418; lithium; TDZD-8; BIO; BIO-Acetoxime; (5-Methyl-1H-pyrazol-3-yl)-(2-phenylquinazolin-4-yl)amine; Pyridocarbazole-cyclopenadienylruthenium complex; TDZD-8 4-Benzyl-2-methyl-1,2,4-thiadiazolidine-3,5-dione; 2-Thio(3-iodobenzyl)-5-(1-pyridyl)-oxadiazole; OTDZT; alpha-4-Dibromoacetophenone; AR-AO 144-18; 3-(1-(3-Hydroxypropyl)-1H-pyrrolo pyridin-3-yl]-4-pyrazin-2-yl-pyrrole-2,5-dione; TWS119; L803 or its myristoylated form; 2-Chloro-1-(4,5-dibromo-thiophen-2-yl)-ethanone; GF109203X; RO318220; TDZD-8; TIBPO; and OTDZT. In one embodiment, the GSK-3 inhibitor is CHIR99021, BIO, TWS119, or Kenpaullone. In one embodiment, the GSK3 inhibitor is TWS119. In another embodiment, the GSK-3 inhibitor is CHIR99021. In yet another embodiment the GSK3 inhibitor is BIO.

MEK/ERK pathway inhibitors refer to inhibitors of either MEK or ERK serine/threonine kinases that are part of the Raf/MEK/ERK pathway. ERK/MEK inhibitors suitable for use in compositions contemplated herein include, but not limited to: PD0325901, PD98059, U0126, SL327, ARRY-162, PD184161, PD184352, sunitinib, sorafenib, vandetanib, pazopanib, axitinib, GSK1 120212, ARRY-438162, R05126766, XL518, AZD8330, RDEA1 19, AZD6244, FR180204, PTK787, 6-(4-Bromo-2-chloro-phenylamino)-7-fluoro-3-methyl-3H-benzoimidazol-e-5-carboxylic acid (2,3-dihydroxy-propoxy)-amide; 6-(4-Bromo-2-chloro-phenylamino)-7-fluoro-3-(tetrahydro-pyran-2-ylm-ethyl)-3H-benzoimidazole-5-carboxylic acid (2-hydroxy-ethoxy)-amide, 1-[6-(4-Bromo-2-chloro-phenylamino)-7-fluoro-3-methyl-3H-benzoimidazol-5-yl]-2-hydroxy-ethanone, 6-(4-Bromo-2-chloro-phenylamino)-7-fluoro-3-methyl-3H-benzoimidazole-5-carboxylic acid (2-hydroxy-1,1-dimethyl-ethoxy)-amide, 6-(4-Bromo-2-chloro-phenylamino)-7-fluoro-3-(tetrahydro-furan-2-ylmethyl)-3H-benzoimidazole-5-carboxylic acid (2-hydroxy-ethoxy)-amide, 6-(4-Bromo-2-fluoro-phenylamino)-7-fluoro-3-methyl-3H-benzoimidazol-e-5-carboxylic acid (2-hydroxy-ethoxy)-amide, 6-(2,4-Dichloro-phenylamino)-7-fluoro-3-methyl-3H-benzoimidazole-5-carboxylic acid (2-hydroxy-ethoxy)-amide, 6-(4-Bromo-2-chloro-phenylamino)-7-fluoro-3-methyl-3H-benzoimidazole-5-carboxylic acid (2-hydroxy-ethoxy)-amide, 2-[(2-fluoro-4-iodophenyl)amino]-N-(2-hydroxyethoxy)-1,5-dimethyl-6-oxo-1,6-dihydropyridine-3-carboxamide; referred to hereinafter as MEK inhibitor 2; and 4-(4-bromo-2-fluorophenylamino)-N-(2-hydroxyethoxy)-1,5-dimethyl-6-oxo-1,6-dihydropyridazine-3-carboxamide or a pharmaceutically acceptable salt thereof. Additional illustrative MEK/ERK inhibitors include those compounds disclosed in International Published Patent Applications WO 99/01426, WO 02/06213, WO 03/077914, WO 05/051301 and WO2007/044084. In one embodiment, the MEK inhibitor is PD0325901. In another embodiment, the MEK inhibitor is U0126.

ROCK (Rho associated kinases) inhibitors refer to inhibitors of the Rho-GTPase/ROCK pathway. The pathway includes the downstream protein Myosin II, which is further downstream of ROCK (Rho-ROCK-Myosin II forms the pathway/axis). Thus, one can use any or all of a Rho GTPase inhibitor, a ROCK inhibitor, or a Myosin II inhibitor to achieve the effects described herein. ROCK inhibitors suitable for use in compositions contemplated herein include, but are not limited to: thiazovivin, Y27632, fasudil, AR122-86, Y27632 H-1152, Y-30141, Wf-536, HA-1077, hydroxyl-HA-1077, GSK269962A, SB-772077-B, N-(4-Pyridyl)-N'-(2,4,6-trichlorophenyl)urea, 3-(4-Pyridyl)-1H-indole, (R)-(+)-trans-N-(4-Pyridyl)-4-(1-aminoethyl)-cyclohexanecarboxamide, and ROCK inhibitors disclosed in U.S. Pat. No. 8,044,201, which is herein incorporated by reference in its entirety. In one embodiment, the ROCK inhibitor is thiazovivin, Y27632, or pyrintegrin. In one embodiment, the ROCK inhibitor is thiazovivin.

Activin receptor-like kinase 5 (ALK5) is the principal TGFβ receptor that mediates cellular responses to TGFβs. Upon ligand binding, constitutively active Tβ RII kinase phosphorylates ALK5 which, in turn, activates the downstream signal transduction cascades. TGFβ receptor/ALK5 inhibitors can include antibodies to, dominant negative variants of, and siRNA, microRNA, antisense nucleic acids, and other polynucleotides that suppress expression of, TGFβ/ALK5 receptors. TGFβ receptor/ALK5 inhibitors suitable for use in compositions contemplated herein include, but are not limited to: SB431542; A-83-01 (3-(6-Methyl-2-pyridinyl)-N-phenyl-4-(4-quinolinyl)-1H-pyrazole-1-carbothioamide; 2-(3-(6-Methylpyridin-2-yl)-1H-pyrazol-4-yl)-1,5-naphthyridine, Wnt3a/BIO, GW788388 (−{4-[3-(pyridin-2-yl)-1H-pyrazol-4-yl]pyridin-2-yl}-N-(tetrahydro-2H-pyran-4-yl)benzamide), SM16, IN-1130 (3-((5-(6-methylpyridin-2-yl)-4-(quinoxalin-6-yl)-1H-imidazol-2-yl)methyl)benzamide), GW6604 (2-phenyl-4-(3-pyridin-2-yl-1H-pyrazol-4-yl)pyridine), SB-505124 (2-(5-benzo[1,3]dioxol-5-yl-2-tert-butyl-3H-imidazol-4-yl)-6-methylpyridine hydrochloride); SU5416; 2-(5-benzo[1,3] dioxol-5-yl-2-tert-butyl-3H-imidazol-4-yl)-6-methylpyridine hydrochloride (SB-505124); lerdelimumb (CAT-152); metelimumab (CAT-192); GC-1008; ID11; AP-12009; AP-11014; LY550410; LY580276; LY364947; LY2109761; SD-208; SM16; NPC-30345; Ki26894; SB-203580; SD-093; Gleevec; 3,5,7,2',4'-pentahydroxyflavone (Morin); activin-M108A; P144; soluble TBR2-Fc; and pyrimidine derivatives (see, e.g., those listed in Stiefl, et al., WO2008/006583, herein incorporated by reference). Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman, et al., J, Mol. Pharmacol. 62(1): 65-74 (2002). It is further believed that inhibition of the TGFβ/activin pathway will have similar effects of inhibiting ALK5. Thus, any inhibitor (e.g., upstream or downstream) of the TGFβ/activin pathway can be used in combination with, or instead of, ALK5 inhibitors as described in each paragraph herein. Exemplary TGFβ/activin pathway inhibitors include but are not limited to: TGFβ receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described herein are merely for organizational purposes and one of skill in the art would know that compounds can affect one or more points within a pathway, and thus compounds may function in more than one of the defined categories. In one embodiment, the TGFβ receptor inhibitor comprises SB431542.

PDK1 or 3'-phosphoinositide-dependent kinase-1 is a master kinase associated with the activation of AKT/PKB and many other AGC kinases including PKC, S6K, SGK. An important role for PDK1 is in the signaling pathways activated by several growth factors and hormones including insulin signaling. Exemplary PDK1 agonists include sphingosine (King et al, Journal of Biological Chemistry, 275: 18108-18113, 2000). Exemplary allosteric activators of PDK1 include PS48 ((Z)-5-(4-Chlorophenyl)-3-phenylpent-2-enoic acid), PS08 ((Z)-5-(4-Bromo-2-fluorophenyl)-3-phenylpent-2-enoic acid), 1-(2-(3-(4-Chlorophenyl)-3-oxo-1-phenylpropylthio)acetic acid; 3,5-diphenylpent-2-enoic acids such as compound 12Z (2-(3-(4-Chlorophenyl)-3-oxo-1-phenylpropylthio)acetic acid, (Z)-5-(Napthalen-2-yl)-3-phenylpent-2-enoic acid), and compound 13Z ((Z)-5-(1H-Indol-3-yl)-3-phenylpent-2-enoic acid). In one embodiment, the PDK1 agonist comprises PS48.

Mammalian target of rapamycin (mTOR) inhibitors block the activity of the mammalian target of rapamycin. mTOR is a protein kinase, which regulates growth factors that stimulate cell growth and angiogenesis. mTOR inhibitors suitable for the composition and method of the present invention include, but not limited to rapamycin, and analogues and derivatives thereof comprising sirolimus, sirolimus derivatives, temsirolimus, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, and other O-alkylated or O-methylated rapamycin derivatives.

In some embodiments, the composition for improving therapeutic potential of immune cells suitable for adoptive cell-based therapies comprises at least one agent selected from Table 1. In one embodiment, the composition for improving therapeutic potential of immune cells comprises a combination of at least 2, 3, 4, 5, or 6, or any number, of the agents selected from Table 1.

In one embodiment, the composition comprising at least one agent selected from Table 1 further comprises an organic solvent. In certain embodiments, the organic solvent is substantially free of methyl acetate. In certain embodiments, the organic solvent is selected from the group consisting of dimethyl sulfoxide (DMSO), N,N-dimethylformamide (DMF), dimethoxyethane (DME), dimethylacetamide, ethanol, and combinations thereof. In some embodiments, the organic solvent is DMSO. In some embodiments, the organic solvent is ethanol. In some other embodiments, the organic solvent is a mixture of DMSO and ethanol.

In some embodiments, the composition for improving therapeutic potential of immune cells suitable for adoptive cell-based therapies comprises at least one agent selected from Group I: dorsomorphin, heptelidic acid, 1-Pyrrolidinecarbodithioic acid, and 2-DG. Without being limited to the theory, Group I agents, among other potential roles, may impact cell metabolism and nutrient sensing.

In some embodiments, the composition for improving therapeutic potential of immune cells suitable for adoptive cell-based therapies comprises at least one agent selected from Group II: GSK3 Inhibitor, ROCK inhibitor, TGFβ receptor inhibitor, MEK inhibitor, PDK1 agonist, 6-Mercaptopurine, AC-93253 iodide, tiratricol, PI-103, fulvestrant, thapsigargin, SU 4312, U0126, telmisartan, cyclosporin A, 1,3,5-tris(4-hydroxyphenyl)-4-propyl-1H-pyrazole, BAY 61-3606, protoporphyrin IX disodium, mTOR inhibitor, TWS119, HS173, LY294002, and Pictilisib. Without being limited to the theory, Group II agents, among other potential roles, may impact signal transduction in various functional pathways.

In some embodiments, the composition for improving therapeutic potential of immune cells suitable for adoptive cell-based therapies comprises at least one agent selected from Group III: 5-Azacytidine, fludarabine, roscovitine, and PAC-1. Without being limited to the theory, Group III agents, among other potential roles, may impact cell proliferation and apoptosis.

In some embodiments, the composition for improving therapeutic potential of immune cells suitable for adoptive cell-based therapies comprises at least one agent selected from Group IV: 5,7-dichloro-8-Quinolinol, 2-Naphthacenecarboxamide, 7-chloro-4-(dimethylamino)-1,4,4a,5,5a,6,11,12a-octahy, Nifuroxazide, and Tosufloxacin hydrochloride. Without being limited to the theory, Group IV agents, among other potential roles, may impact cell properties relating to infective processes.

In some embodiments, the composition for improving therapeutic potential of immune cells suitable for adoptive cell-based therapies comprises at least one agent selected from Group V: sertraline, diethylenetriaminepentaacetic acid, edrophonium chloride, BIX01294, terfenadine, and dmPGE2. Without being limited to the theory, Group V agents, among other potential roles, generally may impact other cell properties relating to expansion, maintenance, differentiation, dedifferentiation, survival rate, proliferation, cytotoxicity, cell recall, and/or persistence.

In yet some other embodiments, the composition for improving therapeutic potential of immune cells suitable for adoptive cell-based therapies comprises at least one agent selected from Group I, and one or more agents selected from Group II, Group III, Group IV, and/or Group V.

In some other embodiments, the composition for improving therapeutic potential of immune cells suitable for adoptive cell-based therapies comprises at least one agent selected from Group II, and one or more agents selected from Group I, Group III, Group IV, and/or Group V.

In yet some other embodiments, the composition for improving therapeutic potential of immune cells suitable for adoptive cell-based therapies comprises at least one agent selected from Group III, and one or more agents selected from Group I, Group II, Group IV, and/or Group V.

In still some other embodiments, the composition for improving therapeutic potential of immune cells suitable for adoptive cell-based therapies comprises at least one agent selected from Group IV, and one or more agents selected from Group I, Group II, Group III, and/or Group V.

In still some other embodiments, the composition for improving therapeutic potential of immune cells suitable for adoptive cell-based therapies comprises at least one agent selected from Group IV, and one or more agents selected from Group I, Group II, Group III, and/or Group IV.

In some embodiments, the composition for improving therapeutic potential of immune cells suitable for adoptive cell-based therapies comprises at least one agent selected from a group consisting of a GSK3 inhibitor, a MEK inhibitor, a ROCK inhibitor, a TGFβ inhibitor, a PDK1 agonist, and an mTOR inhibitor.

In some embodiments, the composition comprises a combination of two or more agents selected from Table 1, wherein the agents have additive effect in the combination.

As defined, "additive" refers to when two or more agents in a combination produce an effect nearly equal to the sum of their individual effects. In some embodiments, one or more of the agents in a combination are from the same group: Group I, II, III, IV, or V. In some embodiments, one or more of the agents in a combination are from different groups.

In some embodiments, the composition comprises a synergistic combination of two or more agents selected from Table 1. As defined, "synergy" is an enhanced effect such that the working together of two or more agents to produce an effect greater than the sum of their individual effects. In one embodiment, the composition comprising a synergistic combination comprises at least one agent selected from the group consisting of TWS119, HS173, LY294002, Pictilisib, and 2-DG. In one embodiment, the composition comprises a combination comprising at least one agent selected from the group consisting of TWS119, HS173, LY294002, Pictilisib, and 2-DG, and one or more additional agent selected from the group of compounds listed in Table 1. In one embodiment, the composition comprising TWS119, further comprises two or more additional agents selected from Table 1. In one embodiment, the composition comprising HS173, further comprises two or more additional agents selected from Table 1. In one embodiment, the composition comprising LY294002, further comprises two or more additional agents selected from Table 1. In one embodiment, the composition comprising Pictilisib, further comprises two or more additional agents selected from Table 1. In one embodiment, the composition comprising 2-DG, further comprises two or more additional agents selected from Table 1.

In some embodiments, the composition comprising one or more agents selected from the group consisting of the compounds listed in Table 1, further comprises one of more additional additives selected from the group consisting of peptides, cytokines, mitogens, growth factors, small RNAs, dsRNAs (double stranded RNA), mononuclear blood cells, feeder cells, feeder cell components or replacement factors, vectors comprising one or more polynucleic acids of interest, antibodies and antibody fragments thereof, and/or chemotherapeutic agent or radioactive moiety. In some embodiments, the additional additive comprises an antibody, or an antibody fragment. In some of these embodiments, the antibody, or antibody fragment, specifically binds to a viral antigen. In other embodiments, the antibody, or antibody fragment, specifically binds to a tumor antigen.

In some embodiments, the cytokine and growth factor comprise one or more of the following cytokines or growth factors: epidermal growth factor (EGF), acidic fibroblast growth factor (aFGF), basic fibroblast growth factor (bFGF), leukemia inhibitory factor (LIF), hepatocyte growth factor (HGF), insulin-like growth factor 1 (IGF-1), insulin-like growth factor 2 (IGF-2), keratinocyte growth factor (KGF), nerve growth factor (NGF), platelet-derived growth factor (PDGF), transforming growth factor beta (TGF-β), vascular endothelial cell growth factor (VEGF) transferrin, various interleukins (such as IL-1 through IL-18), various colony-stimulating factors (such as granulocyte/macrophage colony-stimulating factor (GM-CSF)), various interferons (such as IFN-γ), stem cell factor (SCF) and erythropoietin (Epo). In some embodiments, the cytokine comprises at least interleukin-2 (IL-2), interleukin 7 (IL-7), interleukin-12 (IL-12), interleukin-15, interleukin 18 (IL-18), interleuckin 21 (IL-21), or any combinations thereof. In some embodiments, the growth factor of the composition comprises fibroblast growth factor. These cytokines may be obtained commercially, for example from R&D Systems (Minneapolis, Minn.), and may be either natural or recombinant. In particular embodiments, growth factors and cytokines may be added at concentrations contemplated herein. In certain embodiments growth factors and cytokines may be added at concentrations that are determined empirically or as guided by the established cytokine art.

In some embodiments, the mitogen of the composition comprises concanavalin A. In some other embodiments, the feeder cells are genetically modified. In some embodiments, the feeder cells comprise one or more of the followings: mononuclear blood cells, thymic epithelial cells, endothelial cells, fibroblasts, leukemic cells K562, Raji cells, or feeder cell components or replacement factors thereof.

In some embodiments, the small RNA comprises one or more of siRNA, shRNA, miRNA and antisense nucleic acids. In some other embodiments, the small RNA comprises one or more of the followings: miR-362-5p, miR-483-3p, miR-210 and miR-598.

In some embodiments, the vector comprising one or more polynucleic acids of interest is integrating or non-integrating. In some embodiments, the vector comprising one or more polynucleic acids of interest further comprises backbones of an adenovirus vector, plasmid vector, adeno-associated virus vector, retrovirus vector, lentivirus vector, Sendai virus vector, episomal vector and the like. In some embodiments, the plasmid vectors for the expression in animal cells include, for example, pAl-11, pXT1, pRc/CMV, pRc/RSV, pcDNAI/Neo, and the like. In some embodiments, the one or more polynucleic acids comprised in the vector encode one or more proteins or polypeptides. In some embodiments, the one or more polynucleic acids encode Delta-like 1 (DLL1), Delta-like 3 (DLL3), Delta-like 4 (DLL4), Jagged1 (Jag1), or Jagged2. In some embodiments, the one or more polynucleic acids encode Jagged 1.

II. Immune Cells for Adoptive Cellular Therapies

The present invention provides a composition comprising an isolated population or subpopulation of immune cells that have been contacted with one or more agents selected from Table 1. In one embodiment, the isolated population or subpopulation of immune cells have been contacted with one or more agents selected from Table 1 in an amount sufficient to improve the therapeutic potential of the immune cells. In some embodiments, the treated immune cells are used in a cell-based adoptive therapy. The present invention further provides a population or subpopulation of immune cells, and one or more agents selected from the agents listed in Table 1, wherein a treatment of the population or subpopulation of immune cells using the one or more agents selected from the agents listed in Table 1 improves the therapeutic potential of the immune cells for adoptive therapy. The treatment can modify the biological properties of the immune cells to improve cell proliferation, cytotoxicity, and persistence, and/or reduce the relapse rate of the cell therapy.

In some embodiments, the population of immune cells comprises T cells. In some embodiments, the population of immune cells comprises NK cells. In some embodiments, the population of immune cell comprises NKT cell.

In some embodiments, a population or subpopulation of T cells contacted with one or more agents selected from Table 1 comprises an increased number or ratio of naïve T cells (Tn), stem cell memory T cells (Tscm), and/or central memory T cells (Tcm), and/or improved cell proliferation, cytotoxicity, cell recall, and/or persistence in comparison to the T cells without the same treatment. In some embodiments the number of Tn, Tscm, and/or Tcm is increased by at least 10%, 20%, 30%, 40%, 50%, 60%, 70%, 80%, 90%, or increased by at least 5, 10, 15, or 20 fold compared to the number of Tn, Tscm, and/or Tcm in the cell population without the same treatment with one or more agents selected from Table 1.

In some embodiments, a population or subpopulation of NK cells contacted with one or more agents selected from Table 1 comprises an increased number or ratio of adaptive (or memory) NK cells, and/or improved cell proliferation, cytotoxicity, cell recall, and/or persistence in comparison to the NK cells without the same treatment. In some embodiments the number of adaptive NK cells is increased by at least 10%, 20%, 30%, 40%, 50%, 60%, 70%, 80%, 90%, or increased by at least 5, 10, 15, or 20 fold compared to the number of adaptive NK cells in the cell population without the same treatment with one or more agents selected from Table 1. In one embodiment, a population or subpopulation of NK cells contacted with a GSK3 inhibitor, a MEK inhibitor, a ROCK inhibitor, a TGFβ inhibitor, a PDK1 agonist, and/or rapamycin comprises an increased number or ratio of adaptive NK cells. In one embodiment, the adaptive NK cell is characterized by CD3− and CD56+, and at least one of CD57+, NKG2C+, low PLZF, low SYK, low FcεRγ, low EAT-2, low TIGIT, low PD1, low CD7, low CD161, high LILRB1, high CD45RO, and low CD45RA. In some embodiments, the adaptive NK cells are at least two of CD57+, NKG2C+, low PLZF, low SYK, low FcεRγ, low EAT-2, low TIGIT, low PD1, low CD7, low CD161, high LILRB1, high CD45RO, and low CD45RA. For example, the adaptive NK cell can be CD57+ and NKG2C+. In some embodiments, the adaptive NK cells are at least three of CD57+, NKG2C+, low PLZF, low SYK, low FcεRγ, low EAT-2, low TIGIT, low PD1, low CD7, low CD161, high LILRB1, high CD45RO, and low CD45RA. For example, the adaptive NK cell can be SYK−, FcεRγ−, and EAT-2−. In one embodiment, the GSK-3β inhibitor is CHIR99021, BIO, TWS119, or Kenpaullone. In one embodiment, the GSK-3β inhibitor is TWS119. In another embodiment, the GSK-3β inhibitor is CHIR99021. In yet another embodiment the GSK-3β inhibitor is BIO.

In some other embodiments, a population or subpopulation of NKT cells contacted with one or more agents selected from Table 1 comprises an increased number or ratio of type I NKT cells vs type II, and/or improved cell proliferation, cytotoxicity, cell recall, and/or persistence in comparison to the isolated population or subpopulation of NKT cells without the treatment with one or more agents selected from Table 1. In some embodiments the number of type I NKT cells is increased by at least 10%, 20%, 30%, 40%, 50%, 60%, 70%, 80%, 90%, or increased by at least 5, 10, 15, or 20 fold compared to the number of type I NKT cells in the cell population without the same treatment with one or more agents selected from Table 1.

In some embodiments, the increased number or ratio of naïve T cells (Tn), stem cell memory T cells (Tscm), central memory T cells (Tcm), adaptive NK cells, and/or type I NKT cells are due to improved maintenance and expansion of these cell subtypes, and/or increased cell dedifferentiation/reprogramming from more mature cell subtypes to cell subtypes in a desired differentiation state.

In some embodiments, after contacting a population of immune cells with one or more of the agents included in Table 1, the number of naïve T cells (Tn), stem cell memory T cells (Tscm), central memory T cells (Tcm) in the population is increased in comparison to untreated immune cell population, wherein the Tn, Tscm and Tcm are characterized by co-expression of CCR7 and/or CD62L.

In some embodiments, after contacting a population of immune cells with one or more of the agents included in Table 1, the number of adaptive NK cells in the population is increased in comparison to untreated immune cell population, wherein the adaptive NK cells are characterized by CD3−, CD56+, CD16+, NKG2C+, and CD57+. In some other embodiments, the adaptive NK cells are characterized by CD3−, CD56+, and at least one, two or three of CD57+, NKG2C+, low PLZF, low SYK, low FcεRγ, low EAT-2, low TIGIT, low PD1, low CD7, low CD161, high LILRB1, high CD45RO, and low CD45RA.

In some embodiments, after contacting a population of immune cells with one or more of the agents included in Table 1, the number of type I NKT cells in the population is increased in comparison to untreated immune cell population, wherein the type I NKT cells are characterized by surface antigens CD3+, CD56+, TCR Vα24+, and/or TCR Vβ11+.

In some embodiments, the population or subpopulation of T, NK or NKT cells for treatment by the agents disclosed herein can be isolated from a human or a non-human mammal. Examples of such non-human mammals include, but are not limited to rabbit, horse, bovine, sheep, pigs, dogs, cats, mice, rats, and transgenic species thereof.

The population or subpopulation of T cells can be obtained or isolated from a number of sources, including but not limited to peripheral blood, bone marrow, lymph node tissue, cord blood, thymus tissue, and tissue from a site of infection, ascites, pleural effusion, spleen tissue, and tumors. The bone marrow can be obtained from femurs, iliac crest, hip, ribs, sternum, and other bones. In addition, the T cell lines available in the art can also be used, such as Jurkat, SupT1, and others.

The population or subpopulation of NK cells can be obtained or enriched from a number of sources, including but not limited to peripheral blood, cord blood, and tumors.

Fully mature NKT cells can be obtained or enriched from peripheral blood, with smaller populations of mature NKT cells potentially found in bone marrow, lymph node tissue and cord blood, thymus tissue.

In certain embodiments of the present invention, an isolated or enriched population or subpopulation of T, NK, NKT cells can be obtained from a unit of blood using any number of techniques known to the skilled artisan, such as Ficoll™ separation. In one embodiment, T, NK or NKT cells from the circulating blood of an individual are obtained by apheresis. The apheresis product typically contains cells, including T cells, monocytes, granulocytes, B cells, NK cells, NKT cells, other nucleated white blood cells, red blood cells, and platelets. In one embodiment, the cells collected by apheresis can be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and can lack magnesium or can lack many if not all divalent cations. As those of ordinary skill in the art would readily appreciate a washing step can be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells can be resuspended in a variety of biocompatible buffers, such as, for example, Ca-free, Mg-free PBS, PlasmaLyte A, or other saline solution with or without buffer. Alternatively, the undesirable components of the apheresis sample can be removed and the cells directly resuspended in culture media.

In another embodiment, the population or subpopulation of T, NK or NKT cells are isolated or enriched from peripheral blood lymphocytes by lysing the red blood cells and depleting the monocytes, for example, by centrifugation through a PERCOLL™ gradient or by counterflow centrifugal elutriation.

In one embodiment, a specific subpopulation of T cells, can be further isolated or enriched by positive or negative selection techniques such as CD3, CD28, CD4, CD8, CD45RA, CD45RO, CD62L, CCR7, CD27, and/or CD122 antibodies. For example, in one embodiment, the isolated or enriched population or subpopulation of T cells are expanded and activated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 72 hours or longer and all integer values between. In a further embodiment, the time period is at least 1, 2, 3, 4, 5, or 6 hours. In yet another preferred embodiment, the time period is 10 to 72 hours. In one preferred embodiment, the incubation time period is 24 hours. For isolation of T cells from patients with leukemia, use of longer incubation times, such as 24 hours, can increase cell yield. Longer incubation times can be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), specific populations or subpopulations of T cells can be further selected for or against at culture initiation or at other time points during the process. Additionally, by increasing or decreasing the ratio of anti-CD3 and/or anti-CD28 antibodies on the beads or other surface, specific populations or subpopulations of T cells can be preferentially selected for or against at culture initiation or at other desired time points. The skilled artisan would recognize that multiple rounds of selection can also be used in the context of this invention. In certain embodiments, it can be desirable to perform the selection procedure and use the "unselected" cells in the activation and expansion process. "Unselected" cells can also be subjected to further rounds of selection.

Isolation or enrichment of a population or subpopulation of T, NK or NKT cells by negative selection can be accomplished with a combination of antibodies directed to surface markers unique to the negatively selected cells. One method is cell sorting and/or selection via negative magnetic immuno-adherence or fluorescence-activated cell sorting that uses a cocktail of monoclonal antibodies directed to cell surface markers present on the cells negatively selected. For example, to enrich for CD3+ cells by negative selection, a monoclonal antibody cocktail typically includes antibodies to CD14, CD20, CD11b, CD16, and HLA-DR. In certain embodiments, it can be desirable to enrich for or positively select for regulatory T cells which typically express CD4+, CD25+, CD62Lhi, GITR+, and FoxP3+. Alternatively, in certain embodiments, T regulatory cells are depleted by anti-CD25 conjugated beads or other similar method of selection. In some embodiments, a desired T cell subpopulation for immunotherapy is enriched or selected from the modulated immune cells comprising T cells by CCR7 and CD62L. Alternatively cells of interest may be selected according to physical parameters including differential size, density, granularity, deformability, resistance or capacitance.

In one embodiment, a population or subpopulation of adaptive NK cells are enriched by selecting within the modulated immune cells comprising NK cells for those phenotypically CD3− and CD56+, using the identifiers such as include positive expression of CD16, NKG2C, and CD57. Further, negative selection of adaptive subpopulation can be based on lack of expression of NKG2C and/or CD57, and additionally lack expression of one or more of the following: low PLZF, low SYK, low FcεRγ, low EAT-2, low TIGIT, low PD1, low CD7, low CD161, high LILRB1, high CD45RO, and low CD45RA.

In one embodiment, a population or subpopulation of NKT cells are enriched by selecting within the population of NK cells for those phenotypically expressing the invariant TCRα chain, and specifically the following combination of markers: CD3+, CD56+, TCR Vα24+, and/or TCR Vβ11+. Alternatively, NKT cells can be selected based on a combination of phenotype combined with expression of the invariant TCRα chain.

The blood samples or apheresis product from a subject can be collected at a time period prior to when the immune cells as described herein are isolated. As such, the source of the cells to be modulated can be collected at any time point necessary, and desired cells, such as T cells, NK cells and NKT cells, isolated and frozen for later use in cell-based immunotherapy for any number of diseases or conditions that would benefit from such cell therapy, such as those described herein. In one embodiment a blood sample or an apheresis product is collected from a generally healthy subject. In certain embodiments, a blood or an apheresis product is collected from a generally healthy subject who is at risk of developing a disease, but who has not yet developed a disease, and the cells of interest are isolated and frozen for later use. In other embodiments, a blood sample or an apheresis product is collected from a subject who has been previously administered with genetically modified immune cells (genetically engineered or naturally derived from rearrangements, mutations, genetic imprinting and/or epigenetic modification). In certain embodiments, the T, NK, NKT or other immune cells can be expanded, frozen, and treated and used at a later time. In certain embodiments, samples are collected from a patient shortly after diagnosis of a particular disease as described herein but prior to any treatments. In some embodiments, the cells are isolated from a subject presenting CMV (cytomegalovirus) seropositivity. In a further embodiment, the cells are isolated from a blood or an apheresis product from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. In a further embodiment, the cells are isolated from a patient and frozen for later use in conjunction with (e.g., before, simultaneously or following) bone marrow or stem cell transplantation. T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In some embodiments, the population or subpopulation of T, NK or NKT cells are genomically engineered, which include insertion, deletion, or nucleic acid replacement. Modified immune cells may express cytokine transgenes, silenced inhibitory receptors; or overexpress activating receptors, or CARs for retargeting the immune cells. In some embodiments, the population of immune cells isolated for modulation from a subject, or donor, or isolated from or comprised in peripheral blood, bone marrow, lymph node tissue, cord blood, thymus tissue, tissue from a site of infection, ascites, pleural effusion, spleen tissue, tumors of a subject/donor may be genetically modified. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof.

The genomically engineered immune cells comprise genetically modified modalities including one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the immune cells. In some other embodiments, the genetically modified modalities include one or more of (i) deletion or reduced expression of B2M, TAP1, TAP2, Tapasin, NLRC5, PD1, LAG3, TIM3, RFXANK, CIITA, RFX5, or RFXAP, and any gene in the chromosome 6p21 region; (ii) introduced or increased expression of HLA-E, HLA-G, HACD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers. In some embodiments, the T, NK or NKT cells comprise an exogenous nucleic acid. In some embodiments, the exogenous nucleic acid is introduced to the immune cells via direct genomic editing of the cells. In some other embodiments, the exogenous nucleic acid is introduced to the immune cells via retaining the same from a genomically engineered hematopoietic stem or progenitor cell or iPSC, which gives rise to the immune cell through differentiation. In some embodiments, the exogenous nucleic acid for a T cell can encode a TCR (T Cell Receptor), a CAR (Chimeric Antigen Receptor), a bi-specific T cell engager (BiTE), a tri-specific T cell engager, a multi-specific T cell engager, or a universal engager compatible with multiple immune cell types. In some embodiments, the exogenous nucleic acid for a NK cell can encode a TCR, a CAR, a CD16 or a variant thereof, a NY-ESO, a bi-specific killer cell engager (BiKE), a tri-specific killer cell engager (TriKE), a multi-specific killer cell engager, or a universal engager compatible with multiple immune cell types. In some embodiments, the exogenous nucleic acid for a NKT cell can be an altered TCR or CAR. In some embodiments, the exogenous nucleic acid encoding CAR19. In some embodiments, CD16 variants comprise high-affinity CD16 (HACD16), non-cleavable CD16, and high-affinity non-cleavable CD16 (hnCD16). Accordingly, in view of the methods and compositions for modulating immune cells using GSK3i, some aspects of the present invention provide GSK3i modulated genetically engineered T, NK, or NKT cells. One aspect of the present invention provides GSK3i modulated NK cells comprising hnCD16. Another aspect of the present invention provides GSK3i modulated immune cells with modified HLA class I and/or II. In some embodiments, GSK3i modulated immune cells with modified HLA class I and/or II comprise null or low expression of at least one of B2M, HLA-E/G; PDL1, A2AR, CD47, LAG3, TIM3, TAP1, TAP2, Tapasin, NLRC5, PD1, RFKANK, CIITA, RFX5, and RFXAP.

In some embodiments, the population or subpopulation of immune cells for modulation is differentiated in vitro from a stem cell or progenitor cell. In some embodiments, the isolated population or subpopulation of T, NK or NKT cells can be differentiated from a stem cell, a hematopoietic stem or progenitor cell (HSC), or a progenitor cell. The progenitor cell can be a CD34+ hemogenic endothelium cell, a multipotent progenitor cell, a T cell progenitor, a NK cell progenitor, or a NKT cell progenitor. The stem cell can be a pluripotent stem cell, such as induced pluripotent stem cells (iPSCs) and embryonic stem cells (ESCs). The iPSC is a non-naturally occurring reprogrammed pluripotent cell. Once the cells of a subject have been reprogrammed to a pluripotent state, the cells can then be programmed or differentiated to a desired cell type or subtypes, such as T, NK, or NKT cells. In some embodiments, the iPSC is differentiated to a T, NK or NKT cells by a multi-stage differentiation platform wherein cells from various stages of development can be induced to assume a hematopoietic phenotype, ranging from mesodermal stem cells, to fully differentiated T, NK or NKT cells (See e.g. US Applications 62/107,517 and 62/251,016, the disclosures of which are incorporated herein in their entireties).

In some embodiments, the iPSC, HSC, or progenitor for T, NK or NKT cell differentiation is genomically engineered, which include insertion, deletion, or nucleic acid replacement. In some embodiments, the genomically engineered iPSC, HSC or hematopoietic progenitor cells comprise genetically modified modalities including one or more of: safety switch proteins, targeting modalities, receptors, signaling molecules, transcription factors, pharmaceutically active proteins and peptides, drug target candidates; or proteins promoting engraftment, trafficking, homing, viability, self-renewal, persistence, immune response regulation and modulation, and/or survival of the iPSC, HSC, progenitor, or their derived cells. In some other embodiments, the genetically modified modalities include one or more of (i) deletion or reduced expression of B2M, TAP1, TAP2, Tapasin, NLRC5, PD1, LAG3, TIM3, RFXANK, CIITA, RFX5, or RFXAP, and any gene in the chromosome 6p21 region; (ii) introduced or increased expression of HLA-E, HLA-G, HACD16, hnCD16, 41BBL, CD3, CD4, CD8, CD47, CD113, CD131, CD137, CD80, PDL1, A2AR, Fc receptor, surface triggering receptors for coupling with bi- or multi-specific or universal engagers, a TCR (T Cell Receptor), or a CAR (Chimeric Antigen Receptor). In some embodiments, the iPSC, HSC, or progenitor for T, NK or NKT cell differentiation comprises modified HLA class I and/or II. In some embodiments, the iPSC, HSC, or progenitor for T, NK or NKT cell differentiation with modified HLA class I and/or II comprises null or low expression of at least one of B2M, HLA-E/G; PDL1, A2AR, CD47, LAG3, TIM3, TAP1, TAP2, Tapasin, NLRC5, PD1, RFKANK, CIITA, RFX5, and RFXAP. In some embodiments, the iPSC, HSC, or progenitor for T, NK or NKT cell differentiation has an exogenous nucleic acid. In some embodiments, the exogenous nucleic acid can encode, a bi-specific T cell engager (BiTE), a tri-specific T cell engager, a multi-specific T cell engager, a CD16 or a variant thereof, a NY-ESO, a bi-specific killer cell engager (BiKE), a tri-specific killer cell engager (TriKE), a multi-specific killer cell engager, or a universal engager compatible with multiple immune cell types. In some embodiments, the exogenous nucleic acid encoding hnCD16 in the iPSC, HSC, or progenitor for T, NK or NKT cell differentiation. In some embodiments, the exogenous nucleic acid encoding CAR19 in the iPSC, HSC, or progenitor for T, NK or NKT cell differentiation.

In some embodiments, the population or subpopulation of immune cells is trans-differentiated in vitro from a non-pluripotent cell of non-hematopoietic fate to a hematopoietic lineage cell or from a non-pluripotent cell of a first hematopoietic cell type to a different hematopoietic cell type, which can be a T, NK, or NKT progenitor cell or a fully differentiated specific type of immune cell, such as T, NK, or NKT cell (See e.g. U.S. Pat. No. 9,376,664 and U.S. application Ser. No. 15/072,769, the disclosure of which is incorporated herein in their entirety). In some embodiments, the non-pluripotent cell of non-hematopoietic fate is somatic cells, such as skin fibroblasts, adipose tissue-derived cells and human umbilical vein endothelial cells (HUVEC). Somatic cells useful for trans-differentiation may be immortalized somatic cells.

Various strategies are being pursued to induce pluripotency, or increase potency, in cells (Takahashi, K., and Yamanaka, S., Cell 126, 663-676 (2006); Takahashi et al., Cell 131, 861-872 (2007); Yu et al., Science 318, 1917-1920 (2007); Zhou et al., Cell Stem Cell 4, 381-384 (2009); Kim et al., Cell Stem Cell 4, 472-476 (2009); Yamanaka et al., 2009; Saha, K., Jaenisch, R., Cell Stem Cell 5, 584-595 (2009)), and improve the efficiency of reprogramming (Shi et al., Cell Stem Cell 2, 525-528 (2008a); Shi et al., Cell Stem Cell 3, 568-574 (2008b); Huangfu et al., Nat Biotechnol 26, 795-797 (2008a); Huangfu et al., Nat Biotechnol 26, 1269-1275 (2008b); Silva et al., Plos Bio 6, e253. Doi: 10.1371/journal. Pbio. 0060253 (2008); Lyssiotis et al., PNAS 106, 8912-8917 (2009); Ichida et al., Cell Stem Cell 5, 491-503 (2009); Maherali, N., Hochedlinger, K., Curr Biol 19, 1718-1723 (2009b); Esteban et al., Cell Stem Cell 6, 71-79 (2010); and Feng et al., Cell Stem Cell 4, 301-312 (2009)), the disclosures of which are hereby incorporated by reference in their entireties.

III. Method of Modulating Immune Cells for Adoptive Therapies

The present invention provides a method of modulating a population or a subpopulation of immune cells suitable for adoptive cell-based therapies, and the method comprises contacting the immune cells with a composition comprising at least one agent selected from Table 1.

In one embodiment, the method of modulating a population or a subpopulation of immune cells suitable for adoptive cell-based therapies comprises contacting the immune cells with a composition comprising at least one agent selected from Table 1 wherein the contacted immune cells have increased cell expansion, increased number or ratio of one or more desired cell subpopulations, and/or improved proliferation, cytotoxicity, cell recall, and/or persistence in comparison to immune cells without contacting the agents of Table 1.

In some embodiments, the method of modulating a population or a subpopulation of immune cells suitable for adoptive cell-based therapies comprises contacting the immune cells with a composition comprising at least one agent selected from Table 1, wherein the maintenance and expansion of one or more desired subpopulation of cells are improved in comparison to immune cells without contacting the agents of Table 1.

In some embodiments, the method of modulating a population or a subpopulation of immune cells suitable for adoptive cell-based therapies comprises contacting the immune cells with a composition comprising at least one agent selected from Table 1, wherein the number or ratio of immune cells in the population reprogrammed to a desired state of differentiation is increased in comparison to immune cells without contacting the agents of Table 1.

In some embodiments, the method of modulating a population or a subpopulation of immune cells suitable for adoptive cell-based therapies comprises contacting the immune cells with a composition comprising at least one agent selected from Table 1 in a sufficient amount for increasing cell expansion, increasing number or ratio of one or more desired immune cell subpopulations, and/or improving proliferation, cytotoxicity, cell recall, and/or persistence of the immune cell in comparison to immune cells without contacting the agents of Table 1. In one embodiment, the agent for immune cell treatment is between about 0.1 nM to about 50 µM. In one embodiment, the agent for immune cell treatment is about 0.1 nM, 0.5 nM, 1 nM, 5 nM, 10 nM, 50 nM, 100 nM, 500 nM, 1 µM, 5 µM, 10 µM, 20 µM, or 25 µM, or any concentration in-between. In one embodiment, the agent for immune cell treatment is between about 0.1 nM to about 5 nM, is between about 1 nM to about 100 nM, is between about 50 nM to about 250 nM, between about 100 nM to about 500 nM, between about 250 nM to about 1 µM, between about 500 nM to about 5 µM, between about 3 µM to about 10 µM, between about 5 µM to about 15 µM, between about 12 µM to about 20 µM, or between about 18 µM to about 25 µM.

In some embodiments, the method of modulating a population or a subpopulation of immune cells suitable for adoptive cell-based therapies comprises contacting the immune cells with a composition comprising at least one agent selected from Table 1 for a time sufficient for increasing cell expansion, increasing number or ratio of one or more desired immune cell subpopulations, and/or improving proliferation, cytotoxicity, cell recall, and/or persistence of the immune cell in comparison to immune cells without contacting the agents of Table 1. In one embodiment, the immune cells are contacted with one or more agent of Table 1 for at least 30 minutes, 1 hours, 2, hours, 5 hours, 12 hours, 16 hours, 18 hours, 1 day, 2 days, 3 days, 4 days, 5 days, 6 days, 7 days, 10 days, 15 days, 20 days, 25 days, 30 days, or any length of period in between. In one embodiment, the immune cells are contacted with one or more agent of Table 1 for between about 0.5 hour to about 2 hours, between about 1 hour to about 12 hours, between about 10 hours to about 2 days, between about 1 day to about 3 days, between about 2 days to about 5 days, between about 3 days to about 6 days, between about 5 days to about 8 days, between about 7 days to about 14 days, between about 12 days to about 22 days, between about 14 days to about 25 days, between about 20 days to about 30 days. In some embodiments, the immune cells are contacted with one or more agent of Table 1 for no less than 16 hours, 14 hours, 12 hours, 10 hours, 8 hours, 6 hours, 4 hours, 2 hours, or any length of time in between. As such, said sufficient length of time, for example, is no less than 15, 13, 11, 9, 7, 5, 3, or 1 hour(s). In some other embodiments of the method, said sufficient length of time is no less than 24 hours, 36 hours, 48 hours, 60 hours, 72 hours, or any length of time in between. As such, said sufficient length of time is, for example, no less than 30, 42, 54, 66, 78, 90 hour(s).

The method of modulating a population or a subpopulation of immune cells suitable for adoptive cell-based therapies that comprises contacting the immune cells with a composition comprising at least one agent selected from Table 1, may further comprise enriching or isolating one or more desired subpopulations from the immune cells after the contacting, wherein the one or more desired subpopulations are selected from the group consisting of naïve T cell, stem cell memory T cell, central memory T cell, adaptive NK cell, and type I NKT cell. The adaptive NK cells may have the phenotype of CD57+NKG2C+ or further matured population of CD57+. In some embodiments, a sufficient amount of composition comprising a GSK3 inhibitor, and at least one of the stimulating cytokines comprising IL2, IL15, IL12, IL18 and IL21, or one or more of a MEK inhibitor, a rapamycin, and a STING agonist may be used for treatment/modulation. In some embodiments, the composition comprising a GSK3 inhibitor may further comprise one or more additional additives selected from the group consisting of peptides, cytokines, mitogens, growth factors, small RNAs, dsRNAs (double stranded RNAs), mononuclear blood cells, feeder cells, feeder cell components or replacement factors, vectors comprising one or more polynucleic acids of interest, and antibodies or fragments thereof. In some embodiments, the GSK3 inhibitor is CHIR99021. In some embodiments, the additional additive comprises an antibody, or an antibody fragment. In some of these embodiments, the antibody, or antibody fragment, specifically binds to a viral antigen. In other embodiments, the antibody, or antibody fragment, specifically binds to a tumor antigen.

The population of immune cells to be treated or modulated may be isolated from a subject, or donor, or isolated from or comprised in peripheral blood, bone marrow, lymph node tissue, cord blood, thymus tissue, tissue from a site of infection, ascites, pleural effusion, spleen tissue, tumors of a subject/donor. The subject may be healthy, or may have an autoimmune disease, a hematopoietic malignancy, a virus infection or a solid tumor. In some embodiments, the subject is CMV seropositive, or may have been previously administered with genetically modified immune cells. In some embodiments, the subject may be CMV seropositive. In some other embodiments, the isolated immune cells for modulation are genetically modified (genetically engineered or naturally derived from rearrangements, mutations, genetic imprinting and/or epigenetic modification). In some embodiments, the isolated immune cells for modulation comprise at least one genetically modified modality. In some embodiments, the isolated population of immune cells are genomically engineered and comprise an insertion, a deletion, and/or a nucleic acid replacement. In some particular embodiments, the immune cells comprise an exogenous nucleic acid encoding a T Cell Receptor (TCR), a Chimeric Antigen Receptor (CAR), and/or overexpression of CD16 or a variant thereof. As such, the genetically modified immune cells are isolated for ex vivo modulation using the present compositions and methods as disclosed. In some embodiments, after modulation, the genetically modified immune cells isolated from a subject may be administered to the same donor or a different patient.

Alternatively, the population of immune cells for modulation may be differentiated in vitro from stem cell, hematopoietic stem or progenitor cells, or progenitor cells; or trans-differentiated from a non-pluripotent cell of hematopoietic or non-hematopoietic lineage. In some embodiments, the stem cells, hematopoietic stem or progenitor cells, progenitor cells, or a non-pluripotent cell that derive the immune cells for modulation are genomic engineered and comprise an insertion, a deletion, and/or a nucleic acid replacement, as such the derived immune cells for modulation comprise the same genetic modalities introduced by genomic engineering in the source cells.

In a method of modulating a population of NK cells using a GSK3 inhibitor, the population of NK cells is cultured with a sufficient amount of a composition comprising a GSK3 inhibitor for a time sufficient to improve therapeutic potential of the NK cells for adoptive cell therapy. To obtain the population of NK cell for modulation, peripheral blood mononuclear cells (PBMCs) may be isolated from a subject. PBMCs consist of lymphocytes (T cells, approximately 30%-70%; B cells, approximately 10%-20%; NK cells, approximately 5%-20%) and monocytes. The subject may be healthy; may have an autoimmune disease, a hematopoietic malignancy, a virus infection or a solid tumor; or may be CMV seropositive, or may have been previously administered with genetically modified immune cells.

In some embodiments of the method, the isolated PBMCs may be depleted of T cells and B cells, for example, using CD3 and CD19 antibodies, or other sorting methods known in the art. In some embodiments, the isolated PBMCs may be without any prolonged, or with minimal, pre-depletion culturing or expansion. By "without any prolonged, or with minimum, pre-depletion culturing or expansion," it means the pre-depletion culturing of the PBMCs is less than 48 hours, 36 hours, 24 hours, 12 hours, 8 hours, 6 hours, or less than 2 hours. In some embodiments, the pre-depletion culturing of the PBMCs is no more than 2, 4, 6, 8, 10, 12, 24, 48 hours. In one embodiment, pre-depletion culturing of the PBMCs is no more than overnight. In some embodiments, the PBMCs are not cultured at all prior to depletion. By "pre-depletion culturing," it means culturing PBMCs, prior to depletion of T cells and B cells, with cytokine, feeder cells, blocking or activating antibodies, recombinant activating ligands, and/or autologous leukocytes, but without the small molecules as disclosed herein, to maintain or expand the PBMCs. Under typical cytokine culturing conditions, T and B cells may expand more rapidly than other subpopulations, such as NK cells, especially some NK cell subsets including, but not limited to, CD57+ and CD57+ NKG2C+ NK cells. This may be because T and B cells may grow more easily under these culture conditions; may have a faster growth rate; may have a larger percentage in the starting cell population; and/or because the condition is not suitable for these NK cell subsets to grow and expand. Therefore, extended pre-depletion culturing may result in a smaller percentage of the NK cell subsets in the cultured cell population as these NK cell subsets are overgrown. CD57+ cells and adaptive NK cells have been shown to be less proliferative than other NK subpopulations even without the growth pressure/competition from T and B cells under conventional cytokine culturing. As such, culturing PBMCs having less than about 0.1%, about 1%, about 5%, or less than about 10% of CD57+ or adaptive NK cells to start with, without T & B cell depletion, would diminish or even eliminate CD57+ and CD57+NKG2C+ NK subsets from the PBMC population.

Accordingly, one aspect of the present invention provides multiday culturing of a sample comprising PBMCs with GSK3i to selectively expand NK subsets in the PBMC sample. In some embodiments, the PBMCs have been depleted of T cells and B cells. In some embodiments, the PBMCs do not undergo pre-deletion culturing prior to culture with GSK3 inhibitor. In other embodiments, pre-depletion culturing is minimal, and is less than 24 hours, 16 hours, 8 hours or 2 hours, or any length of time in-between. In one embodiment, the multiday culturing in the presence of GSK3 inhibitor is under feeder-free condition. In one embodiment, the multiday culturing in the presence of GSK3 inhibitor is with feeder cells.

According to the present disclosure, in one embodiment, the cell population does not undergo prolonged pre-depletion culturing, and after depletion of T cells and B cells, said cell population comprises CD57−, CD57−NKG2C+, CD57+ and/or CD57+NKG2C+ NK cells. In some embodiments, the percentage of NK cells in the population after depletion but without pre-depletion culturing is about 5%, about 10%, about 15%, about 20%, about 25%, or about 30%. In some embodiment, the percentage of NK cell in the population after depletion but without pre-depletion culturing is at most about 10%, at most about 20%, at most about 30%, at most about 40%, at most about 40%, at most about 50%, at most about 60%, or at most about 70%. In some embodiment, the percentage of CD57+ NK cells or CD57+NKG2C+ cells in the population after depletion but without pre-depletion culturing is about 0.1%, about 0.5%, about 1%, about 5%, about 10%, about 15%, about 20%, about 25%, 30%, 35%, 40%, 45%, 50%, and any percentage in-between.

The above NK cell population, isolated from PBMCs which have been depleted of T and B cells and which have undergone minimal or no pre-depletion culturing, referred to as "overnight primed" NK cells, is then subject to a modulation in the presence of the small molecule(s) provided herein for a time sufficient to modulate the phenotype and functionalities of the NK cells and subpopulations thereof. In some embodiments, modulating the NK cells comprises skewing the NK cells to maturation. In one embodiment, modulating the NK cells comprises skewing the CD57− NK cells to CD57+ NK cells to drive NK cell maturation. In some embodiments, modulating the NK cells comprises skewing the CD57− NKG2C+ NK cells to CD57+ NKG2C+ NK cells. In some embodiments, modulating the NK cells comprises increasing NK cell cytotoxicity, and/or improving cytokine response. In some embodiments, modulating the NK cells comprises skewing the CD57− NK cells to CD57+ NK cells to drive NK cell maturation, to increase cytotoxicity, and to improve cytokine response. In some other embodiments, modulating the NK cells comprises increasing cell expression of one or more of CD107a, NKG2C, NKG2D, CD16, KIR, CD2, and natural cytotoxicity receptor (NCRs). NCRs include NKp30, NKp44 and NKp46. In some other embodiments, modulating the NK cells comprises increasing NKp30 expression. In some other embodiments, modulating the NK cells comprises increasing CD107a. Accordingly, the present invention also provides a population of modulated NK cells having increased expression in one or more of CD107a, NKG2C, NKG2D, CD16, KIR, CD2, NKp30, NKp44 and NKp46 in comparison to unmodulated NK cells, wherein the expression thereof is increased by at least 10%, 20%, 30%, 40%, 50%, 60%, 70%, 80%, 90%, 100% or above. In yet some other embodiments, modulating the NK cells comprises improving proliferation, cytokine release, cell recall, and/or persistence of NK cells or subpopulations thereof. In yet some other embodiments, modulating the NK cells comprises improving cell expansion, maintenance, differentiation, de-differentiation, and/or survival rate of the NK cells or subpopulations thereof.

A time sufficient to modulate the phenotype and/or functionalities of NK cells may comprise, for example, at least 0.5, 1, 2, 3, 4, 5, 6, 7, 8, 9, 10, 11, 12, 13, 14 days, 21 days, 28 days, or any length of time in-between. In some embodiments, NK cells obtained in the method of the invention are modulated in the presence of GSK3 inhibitor for at least 1, 2, 3, 4, 5, 6, 7, 8, 9, 10, 11, 12, 13, 14 days, 21 days, 28 days, or any length of time in-between. In some embodiments, a time sufficient to modulate NK cells is no less than 12 hours, 16 hours, 24 hours, 48 hours, 3 days, 4 days, 5 days, 6 days, or 7 days. In some embodiments, NK cells obtained in the method of the invention are modulated in the presence of GSK3 inhibitor for no less than 24 hours, 48 hours, 3 days, 4 days, 5 days, 6 days, or 7 days. In some embodiments, a time sufficient to modulate NK cells is between 1-28 days, 1-21 days, 1-14 days, 1-7 days, 2-12 days, 3-11 days, 4-10 days, 5-9 days, 6-8 days, 7-14 days, 14-21 days, 21-28 days, or any range included therein. In some embodiments, the NK cells obtained in the method of the invention are modulated in the presence of GSK3i for between 1-28 days, 1-21 days, 1-14 days, 1-7 days, 2-12 days, 3-11 days, 4-10 days, 5-9 days, 6-8 days, 7-14 days, 14-21 days, 21-28 days, or any range included therein. In some embodiments, a time sufficient to modulate NK cells is about 3 days, about 5 days, about 7 days, or about 9 days. In some embodiments, the NK cells obtained in the method of the invention are modulated in the presence of GSK3i for about 3 days, 5 days, about 7 days, or about 9 days.

In some embodiments, the modulation of immune cells for a time sufficient is in the presence of small molecule(s) at less than 30 µM, 25 µM, 20 µM, 15 µM, 10 µM, or 1 µM. In some embodiments, the small molecules used in modulating immune cells for a time sufficient is no more than 25 µM, 20 µM, 15 µM, 10 µM, 5 µM, or 1 µM. In some embodiments, a population of NK cells modulated in the presence of a GSK3 inhibitor for a time sufficient have increased NK cell expansion in number or in percentage by at least 2, 3, 4, 5, 6, 7, 8, 9, or 10 fold. In some embodiments, the population of NK cells modulated in the presence of a GSK3 inhibitor has an NK cell purity of at least about 80%, 85%, 90%, 95%, or at least about 99%. In some embodiments, the population of NK cells modulated in the presence of a GSK3 inhibitor has an increased CD57+ NK cell expansion in number or in percentage by at least 2, 3, 4, 5, 6, 7, 8, 9, or 10 fold. In some embodiments, the percentage of CD57+ NK cells or CD57+NKG2C+ cells in the population after modulation is at least 10%, 15%, 20%, 25%, 30%, 35%, 40%, 45%, 50%, 60%, 70% or 80%, and any percentage there between. In some embodiments, the population of NK cells modulated in the presence of a GSK3 inhibitor has an increased CD57+NKG2C+ NK cell expansion in number or in percentage by at least 2, 3, 4, 5, 6, 7, 8, 9, or 10 fold.

The method of modulating a population of NK cells using a GSK3 inhibitor following the process disclosed herein provides modulated NK cells for cell therapy with increased number or ratio of NK subpopulations such as CD57+ NK cells, and CD57+NKG2C+ NK cells; improved cell expansion, maintenance and maturation; enhanced adaptive/memory-like state of NK cell subsets that leads to improved proliferation, cell recall, and/or persistence; and improved cytotoxicity and cytokine response and secretion. Accordingly, different aspects of the present invention further provide a method of selectively expanding NK cells and subpopulation(s) thereof; a method of expanding and modulating adaptive NK cells; a method of improving NK cell expansion, maintenance or maturation; a method of enhancing adaptive/memory-like state of NK cells; a method of improving NK cell therapeutic potential including, but not limited to, cell proliferation, cell recall, and cell persistence; a method of improving NK cell cytotoxicity; and a method of increasing NK cell cytokine secretion and response, comprising contacting a depleted PBMC sample without pre-depletion culturing, for modulation, with a composition comprising a sufficient amount of GSK3 inhibitor for a time sufficient to obtain modulated cells having improved potential for cell therapies.

In another embodiment, the above methods comprise obtaining a sample of PBMCs from a subject; depleting the PBMC sample, without pre-depletion culturing of the sample, for example, using antibodies comprising CD3 and CD19; and contacting the depleted PBMC sample with a composition comprising a sufficient amount of GSK3i for a time sufficient to obtain modulated cells having improved potential for cell therapies.

In yet another embodiment, the above methods comprise obtaining a sample of PBMCs from a subject; depleting the PBMC sample without pre-depletion culturing of the sample, using antibodies comprising CD3 and CD19 or other non-NK specific markers; contacting the depleted PBMC samples, for modulation, with a composition comprising a sufficient amount of GSK3i for a time sufficient to obtain modulated cells; and isolating CD57+ NK cells from the modulated cells.

In some embodiments of the above methods, the method may further comprise activating the population of NK cells before or during the step of contacting the NK cells with the composition comprising the GSK3 inhibitor.

In some embodiments of the above methods, contacting with a composition comprising a sufficient amount of GSK3i for a time sufficient may be carried out in a feeder-free condition, i.e. without feeder cells or components thereof, and without feeder cell conditioned medium.

In some embodiments of the above methods, contacting with a composition comprising a sufficient amount of GSK3i for a time sufficient may be carried out in the presence of feeder cells. In some embodiments, the feeder cells are modified by genomic editing to express exogenous surface proteins.

IV. Therapeutic Use of the Treated Immune Cells, Immune Cell Population or Subpopulations The present invention provides a composition comprising an isolated population or subpopulation of immune cells that have been contacted with one or more agents selected from Table 1 in an amount sufficient to improve the therapeutic potential of the immune cells when used in a cell based adoptive therapy. In one embodiment, the isolated population or subpopulation of immune cell that has been treated comprises an increased number or ratio of naïve T cells, stem cell memory T cells, and/or central memory T cells. In one embodiment, the isolated population or subpopulation of immune cell that has been contacted comprises an increased number or ratio of type I NKT cells. In another embodiment, the isolated population or subpopulation of immune cell that has been contacted comprises an increased number or ratio of adaptive NK cells. It is contemplated herein that combination treatments using NK cell therapy products together with other drugs that target tumor cells or modulate cytotoxic activity of NK cells. In some embodiments of the composition, the composition further comprises one of more additional additives selected from the group consisting of peptides, cytokines, mitogens, growth factors, small RNAs, dsRNAs (double stranded RNAs), mononuclear blood cells, feeder cells, feeder cell components or replacement factors, vectors comprising one or more polynucleic acids of interest, antibodies, chemotherapeutic agents or radioactive moiety, and immunomodulatory drugs (IMiDs).

The present invention also provides compositions and methods of combinational treatment comprising the immune cells modulated with one or more agents comprising the compounds listed in Table 1, and additional therapeutic agents. In some embodiments, the additional therapeutic agent comprises an antibody, or an antibody fragment. In some embodiments, the antibody may be a humanized antibody, a humanized monoclonal antibody, a chimeric antibody. In some embodiments, the antibody, or antibody fragment, specifically binds to a viral antigen. In other embodiments, the antibody, or antibody fragment, specifically binds to a tumor antigen. In some embodiments, the tumor or viral specific antigen activates the modulated NK cells to make use of antibody-dependent cellular cytotoxicity (ADCC) and lysis of the target cell. Monoclonal antibodies (mAbs) bind to the target cell plus engaging CD16 on NK cells and other cell types resulting in killing of tumor cell by ADCC both in vivo and in vitro. mAbs can also enhance ADCC and stimulate NK cells by blocking NK cell inhibition. In some embodiments, the NK cell mediated ADCC is through expressed CD16 and genetically engineered variants thereof by the modulated NK cells. The genetically engineered variants of CD16 include, but are not limited to, non-cleavable CD16, high affinity CD16 (haCD16), and high affinity non-cleavable CD16 (hnCD16). As such, the above aspect of the present invention provides GSK3i modulated NK cells capable of performing ADCC in antibody combination cancer treatments. In some embodiments, the antibodies suitable for combinational treatment with anti-cancer NK cells provided herein include, but are not limited to, anti-CD20 (retuximab, veltuzumab, ofatumumab, ublituximab, ocaratuzumab, obinutuzumab), anti-Her2 (trastuzumab), anti-CD52 (alemtuzumab), anti-EGFR (certuximab), and anti-CD38 (daratumumab), and their humanized and Fc modified variants. Additionally, the design of bi- and trispecific antibodies, fusing the Fab region of the antibody targeting the tumor cell antigen, such as the anti-CD19, CD20, and CD33 antigens, in combination with another Fab region recognizing CD16 on NK cell leads to stimulation of the NK cells followed by tumor cell killing.

In some embodiments, the additional therapeutic agent comprises one or more chemotherapeutic agents or a radioactive moiety. Chemotherapeutic agent refers to cytotoxic antineoplastic agents, that is, chemical agents which preferentially kill neoplastic cells or disrupt the cell cycle of rapidly-proliferating cells, or which are found to eradicate stem cancer cells, and which are used therapeutically to prevent or reduce the growth of neoplastic cells. Chemotherapeutic agents are also sometimes referred to as antineoplastic or cytotoxic drugs or agents, and are well known in the art.

In some embodiments, the chemotherapeutic agent comprises an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, and an interleukin. Exemplary chemotherapeutic agents include, but are not limited to, alkylating agents (cyclophosphamide, mechlorethamine, mephalin, chlorambucil, heamethylmelamine, thiotepa, busulfan, carmustine, lomustine, semustine), animetabolites (methotrexate, fluorouracil, floxuridine, cytarabine, 6-mercaptopurine, thioguanine, pentostatin), vinca alkaloids (vincristine, vinblastine, vindesine), epipodophyllotoxins (etoposide, etoposide orthoquinone, and teniposide), antibiotics (daunorubicin, doxorubicin, mitoxantrone, bisanthrene, actinomycin D, plicamycin, puromycin, and gramicidine D), paclitaxel, colchicine, cytochalasin B, emetine, maytansine, and amsacrine. Additional agents include aminglutethimide, cisplatin, carboplatin, mitomycin, altretamine, cyclophosphamide, lomustine (CCNU), carmustine (BCNU), irinotecan (CPT-11), alemtuzamab, altretamine, anastrozole, L-asparaginase, azacitidine, bevacizumab, bexarotene, bleomycin, bortezomib, busulfan, calusterone, capecitabine, celecoxib, cetuximab, cladribine, clofurabine, cytarabine, dacarbazine, denileukin diftitox, diethlstilbestrol, docetaxel, dromostanolone, epirubicin, erlotinib, estramustine, etoposide, ethinyl estradiol, exemestane, floxuridine, 5-flourouracil, fludarabine, flutamide, fulvestrant, gefitinib, gemcitabine, goserelin, hydroxyurea, ibritumomab, idarubicin, ifosfamide, imatinib, interferon alpha (2a, 2b), irinotecan, letrozole, leucovorin, leuprolide, levamisole, meclorethamine, megestrol, melphalin, mercaptopurine, methotrexate, methoxsalen, mitomycin C, mitotane, mitoxantrone, nandrolone, nofetumomab, oxaliplatin, paclitaxel, pamidronate, pemetrexed, pegademase, pegasparagase, pentostatin, pipobroman, plicamycin, polifeprosan, porfimer, procarbazine, quinacrine, rituximab, sargramostim, streptozocin, tamoxifen, temozolomide, teniposide, testolactone, thioguanine, thiotepa, topetecan, toremifene, tositumomab, trastuzumab, tretinoin, uracil mustard, valrubicin, vinorelbine, and zoledronate. Other suitable agents are those that are approved for human use, including those that will be approved, as chemotherapeutics or radiotherapeutics, and known in the art. Such agents can be referenced through any of a number of standard physicians' and oncologists' references (e.g. Goodman & Gilman's *The Pharmacological Basis of Therapeutics*, Ninth Edition, McGraw-Hill, N.Y., 1995) or through the National Cancer Institute website (fda.gov/cder/cancer/druglistframe.htm), both as updated from time to time.

Immunomodulatory drugs (IMiDs) such as thalidomide, lenalidomide, and pomalidomide stimulate both NK cells and T cells. As provided herein, IMiDs may be used with the modulated therapeutic immune cells for cancer treatments.

A variety of diseases may be ameliorated by introducing the cells of the invention to a subject suitable for adoptive cell therapy. Examples of diseases including various autoimmune disorders, including but not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barré syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus, erythematosus, some forms of thyroiditis, some forms of uveitis, vitiligo, granulomatosis with polyangiitis (Wegener's); hematological malignancies, including but not limited to, acute and chronic leukemias, lymphomas, multiple myeloma and myelodysplastic syndromes; solid tumors, including but not limited to, tumor of the brain, prostate, breast, lung, colon, uterus, skin, liver, bone, pancreas, ovary, testes, bladder, kidney, head, neck, stomach, cervix, rectum, larynx, or esophagus; and infections, including but not limited to, HIV—(human immunodeficiency virus), RSV—(Respiratory Syncytial Virus), EBV—(Epstein-Barr virus), CMV—(cytomegalovirus), adenovirus- and BK polyomavirus-associated disorders.

EXAMPLES

The following examples are offered by way of illustration and not by way of limitation.

Example 1

Methods and Materials

In Vitro T Cell Culture. Fresh leukopaks (AllCells, Alameda, Calif.) were obtained from healthy donors, from which T cells were negatively selected using the EasySep Human T cell Enrichment Kit (Stem Cell Technologies, Vancouver, Canada). The freshly isolated T cells were aliquoted and cryopreserved. On the day the screens were initiated, T cells were thawed and washed into X-Vivo 15 with 5% human AB serum, IL-2, pen/strep, and additional supplements. Cells were dispensed into flat-bottom 384-well plates at $5 \times 10^5$ cells/ml with anti-CD3/Anti-CD28 dynabeads (ThermoFisher, Waltham, Mass.) at a 3:1 bead-to-cell ratio. Individual compounds were added at a final concentration of 10 µM to each well from column 3 to column 22 of each plate. Positive and negative controls were added to additional wells. Cells were incubated for about 6 days at 37 degrees with 5% CO2.

Flow Cytometry. On Day 6 of culture, cells were stained with a fixable viability marker and fluorophore-conjugated antibodies: CD3, CD4, CD8, CD45RA, CD45RO, CD62L, CCR7, CD27, and CD122 (BD Biosciences, San Jose, Calif.; and BioLegend, San Diego, Calif.). Fluorescent absolute counting beads (Spherotech, Lake Forest, Ill.) were added just prior to acquisition. Data acquisition was performed on a BD Fortessa X-20 (BD Biosciences) and data were analyzed using Treestar software (FlowJo, Ashland, Oreg.) and Spotfire (Tibco, Boston, Mass.).

NK Cell Isolation. Healthy adult donor blood was obtained from commercial sources or from GCRC core laboratory of Scripps Research Institute, La Jolla, Calif. Peripheral blood mononuclear cells (PBMC) were isolated by density gradient centrifugation using Ficoll-Paque PLUS (GE Healthcare: Life Sciences) and then depleted of B and T cells without culturing the PBMC using CD19 Microbeads (Miltenyi Biotec, #130-050-301) and CD3 Microbeads (Miltenyi Biotec, #130-050-101) within 24 to 36 hours according to manufacturer directions.

NK cell culture: CD3/CD19 depleted PBMC (0.5-1× 10E6/mL) were cultured in B0 medium (2:1 mixture of DMEM, (Corning Cell-Gro #10-017-CV) and Ham's F12 (Corning Cell-Gro #10-080-C) with 10% human AB serum (Valley Biomedical, #HP1022), 100 U/mL penicillin and 100 ug/mL streptomycin (Corning, 30-002-CI), 20 uM 2-mercaptoethanol (Sigma, M3148), 50 uM ethanolamine (Sigma, E0135), 10 ug/mL ascorbic acid (Sigma, A4544), and 1.6 ng/mL sodium selenite (Sigma, S5261). Cells were cultured for 7-8 days (up to four weeks) in medium containing 10 ng/mL recombinant human IL-15 (Life Technologies, PHC9154) with or without GSK3 inhibitor CHIR99021 (BioVision #1677-5), histone lysine methyltransferase inhibitor BIX 01294 (Tocris, 3364), TGF-β1 receptor inhibitor SB-431542 (BioVison, 1674-5), or human interferon alpha (R&D Systems, 11200-1). After culturing, cells were counted using trypan blue or by Cellometer (Nexcelom) and used for flow cytometry and functional assays. Flow cytometry was performed on a BD LSR-Fortessa and results were analyzed by FlowJo software. Commercially available antibodies to the following surface markers were used for flow cytometry: CD3, CD14, CD16, CD19, CD56, CD57 and NKG2C (BD Biosciences, Biolegend, or R&D Systems). Where indicated, K562 feeder cells were used. Where indicated other modulators and culture reagents were added.

NK Cell Sorting: CD3/CD19 depleted PBMC were labelled with 10 uM e450 proliferation dye (eBioscience) and stained with FITC-conjugated anti-CD57, PE-Conjugated anti-NKG2C, APC-conjugated anti-CD56, and Percp-Cy5.5-conjugated anti-CD3 antibodies (BD Biosciences and R&D Systems). Four populations of CD3−CD56+ NK cells were sorted according to the expression of CD57 and NKG2C; CD57+NKG2C−, CD57+NKG2C+, CD57−NKG2C+, and CD57−NKG2C−. Sorted NK cell populations were cultured at a 2:1 ratio of NK:monocytes in B0 media with 10 ng/ml IL-15 and CHIR99021 or vehicle control. Stained but unsorted cells were cultured in parallel as a control.

NK Cell Cytotoxicity Assay: Cytotoxicity was determined using a flow cytometry based method based on a previously published method (Kim, et al. J Immunol Methods. 2007 Aug. 31; 325(1-2): 51-66). NK cells were co-cultured with e450-proliferation dye-labelled targets for 4 hours. CellEvent™ Caspase-3/7 Green Flow Cytometry Assay Kit (Lifer Technologies) was used to assay for cell death among target cells, and samples were read on a BD LSRFortessa cytometer. Killing of SKOV-3 targets was quantified using the Incucyte Zoom instrument. SKOV-3 cells were transiently transduced with NucLight-Red Bac-Mam reagent (Essen Biosciences) and co-cultured with the indicated NK cell populations for 74 hours, with images taken on two hour intervals. Caspase 3/7 activity was monitored to indicate target cells undergoing apoptosis using the CellEvent™ Caspase-3/7 Green Detection Reagent. The number of target cells was normalized to SKOV-3 cells cultured alone, and targets undergoing apoptosis were quantified based on caspase 3/7 activity.

NK Cell Intracellular Cytokine Staining: CD3/CD9 depleted PBMC were cultured for 7 days with 10 ng/ml IL-15 and 5 uM CHIR99021 or vehicle control. On culture day 7 cells were washed and cultured separately with IL-12 and IL-18 (10 ng/ml and 50 ng/ml, respectively) (Life Technologies) or with K562 cells at a 1:1 ratio. Golgistop (BD Biosciences) was included in the culture media to facilitate intracellular detection of cytokines. After a 4 hour culture period, cells were stained for cell surface antigens and fixed prior to intracellular staining with antibodies to IFN-gamma and TNF-alpha (BD Biosciences). Staining was performed using the BD Cytofix/Cytoperm™ Kit according to the manufacturer's instructions.

NK Cell Modulating Compound Screening: CD3/CD19 depleted PBMC were cultured with or without feeder cells for 7 days with 10 ng/ml IL-15 and 5 uM CHIR99021. Various small molecules and/or cytokines were added at multiple doses on day 0 to assess their effect on proliferation and phenotype. Cultures were monitored throughout the 7 days for acidification of the media or overgrowth of cells. After culture, cells were harvested and stained for phenotypic analysis by flow cytometry. Data was analyzed for shifts in proliferation and marker expression. Flow cytometry was performed on a BD LSRFortessa and results were analyzed by FlowJo software. Commercially available antibodies to the following surface markers were used for flow cytometry: CD3, CD14, CD16, CD19, CD56, CD57 and NKG2C (BD Biosciences, Biolegend, or R&D Systems).

In vivo tumor clearing using Modulated NK cells: NSG mice were irradiated with 300 rads one day prior to intra-peritoneal transplant of $2 \times 10^5$ luciferase-expressing SKOV-3 cells. 5 days after transplant of the ovarian carcinoma cells, mice were either left untreated, treated with Herceptin only, or treated with Herceptin, IL-15, and NK cells cultured for 7 days with IL-15 and CHIR99021. Luciferase-expressing SKOV-3 cells were imaged on day 21 using the IVIS imaging system.

Example 2

Agent for Immune Cell Modulation

Data were analyzed to identify compounds that either produced a higher proportion or greater absolute number of phenotypically identified naïve, stem cell memory, or central memory T cells. These cells are characterized by expression of CCR7 and CD62L. Therefore, cells co-expressing both of these identifying markers were evaluated. Within the viable CD4+ population and viable CD8+ population, the percent of cells co-expressing CCR7 and CD62L was determined. The expression of either CD62L or CCR7 on T cells, as indicative of the desired T cell subsets, have been described as having favorable functional characteristics for CAR-T cell therapy, and potentially other adoptive T cell therapies. Under the treatment of dorsomorphin, heptelidic acid, GSK3 inhibitor, 6-Mercaptopurine, AC-93253 iodide, tiratricol, PI-103, 5-Azacytidine, 5,7-dichloro-8-Quinolinol, Nitrofurantoin, 5-chloro-7-iodo-8-Quinolinol, or diethylenetri-aminepentaacetic acid, the number or ratio of cells co-expressing CCR7 and CD62L increased in both viable CD4+ population and viable CD8+ population (Table 2). Under the treatment of fulvestrant, thapsigargin, SU 4312, fludarabine, 2-Naphthacenecarboxamide, 7-chloro-4-(dimethylamino)-1,4,4a,5,5a,6,11,12a-octahy, nifuroxazide, edrophonium chloride, the number or ratio of cells co-expressing CCR7 and CD62L increased at least in viable CD8+ population (Table 2). Under the treatment of 1-Pyrrolidinecarbodithioic acid, ammonium salt, U0126, telmisartan, cyclosporin A, 1,3,5-tris(4-hydroxyphenyl)-4-propyl-1H-pyrazole, BAY 61-3606, Protoporphyrin IX disodium, rapamycin, roscovi-tine, PAC-1, tosufloxacin hydrochloride, BIX01294, and terfenadine, the number or ratio of cells co-expressing CCR7 and CD62L increased at least in viable CD8+ population (Table 2).

In addition, GSK3 (Glycogen synthase kinase 3) inhibitor was shown to preserve CD3−CD19−CD56+ NK cells, and increased the adaptive NK cell subpopulation by affecting cell maturation and subtype skewing, based on observation of including, but not limited to CD57+ and NKG2C+ expression.

The number of events in each of these gates relative to the number of absolute counting beads in each sample was calculated, defining a relative measure of the absolute number of naïve, stem cell memory, or central memory T cells within the CD4+ and/or CD8+ populations. A z-Score relative to the screened compound samples within each 384-well plate was calculated for each of these four values: 1) percent CCR7+CD62L+ in CD4+, 2) percent CCR7+CD62L+in CD8+, 3) absolute relative number of CCR7+CD62L+in CD4+, and 4) absolute relative number of CCR7+CD62L+in CD8+ (FIGS. 1A and 1B). Z-scores were also calculated for the percent viability of all cells within each sample and the relative absolute number of cells within each sample. A "Z-Score" is a statistical measurement of a score's relationship to the mean in a group of scores. A Z-score of 0 means the score is the same as the mean. A Z-score can also be positive or negative, indicating whether it is above or below the mean and by how many standard deviations.

Eliminating compounds that have a detrimental impact on T cell proliferation or viability focuses efforts on compounds that are most likely to be amenable to T cell manufacturing strategies. Primary hit compounds were selected by the following criteria: 'percent viability' Z-score of greater than −1, 'relative absolute number of cells' Z-score of greater than −1, and Z-score of one of the 4 values of greater than +2. 34 compounds (Table 2) were selected for having much higher Z-Scores and meeting the above criteria for more than 1 of the 4 primary values. An additional 5 compounds are also included for their abilities to modulate T cells (Table 3)

TABLE 2

Agents For T Cell Modulation In Adoptive Cell Therapies

| Compounds | CAS Number | Compound Information | Group | Group Descriptor | CD8 Hit | CD4 Hit |
| --- | --- | --- | --- | --- | --- | --- |
| Dorsomorphin | 866405-64-3 | AMPK inhibitor | I | Metabolism & Nutrient Sensing | CD8 | CD4 |
| Heptelidic acid | 74310-84-2 | GAPDH inhibitor | I | Metabolism & Nutrient Sensing | CD8 | CD4 |
| 1-Pyrrolidinecarbodithioic acid, ammonium salt | 5108-96-3 | Prevents induction of nitric oxide synthetase | I | Metabolism & Nutrient Sensing | | CD4 |
| GSK3 Inhibitor | Including for example- BIO; 667463-62-9 | GSK-3α/β inhibitor | II | Signaling Pathways | CD8 | CD4 |
| 6-Mercaptopurine | 6112-76-1 | Competes with purine derivatives hypoxanthine and guanine for enzyme HGPRT | II | Signaling Pathways | CD8 | CD4 |
| AC-93253 iodide | 108527-83-9 | Subtype selective RAR (RARα) agonist | II | Signaling Pathways | CD8 | CD4 |
| Tiratricol | 51-24-1 | Thyroid hormone analogue | II | Signaling Pathways | CD8 | CD4 |
| PI-103 | 371935-74-9 | mTOR/PI3K inhibitor | II | Signaling Pathways | CD8 | CD4 |
| Fulvestrant | 129453-61-8 | Estrogen receptor antagonist | II | Signaling Pathways | CD8 | |
| Thapsigargin | 67526-95-8 | sarco/ER Ca2+-ATPase antagonist | II | Signaling Pathways | CD8 | |
| SU 4312 | 5812-07-7 | VEGF receptor protein tyrosine kinase 1/2 and PDGF receptor inhibitor | II | Signaling Pathways | CD8 | |
| U0126 | 109511-58-2 | MAPK/ERK kinase; antagonizes AP-1 transcriptional activity | II | Signaling Pathways | | CD4 |
| Telmisartan | 144701-48-4 | Micardis; angiotensin II receptor anatagonist | II | Signaling Pathways | | CD4 |
| Cyclosporin A | 59865-13-3 | Neoral; immunosuppressive | II | Signaling Pathways | | CD4 |
| 1,3,5-tris(4-hydroxyphenyl)-4-propyl-1H-pyrazole | 263717-53-9 | PPT; a specific estrogen receptor α (ERα) agonist | II | Signaling Pathways | | CD4 |
| BAY 61-3606 | 732983-37-8 | Spleen tyrosine kinase (Syk) inhibitor | II | Signaling Pathways | | CD4 |
| Protoporphyrin IX disodium | 553-12-8 | GCS (guanylate cyclase) activator | II | Signaling Pathways | | CD4 |
| rapamycin | 53123-88-9 | Sirolimus; immunosuppressant | II | Signaling Pathways | | CD4 |
| 5-Azacytidine | 320-67-2 | Cytosine nucleoside analog that interferes with nucleic acid synthesis | III | Proliferation and Apoptosis | CD8 | CD4 |
| Fludarabine | 21679-14-1 | Purine analog that interferes with nucleic acid synthesis | III | Proliferation and Apoptosis | CD8 | |
| Roscovitine, (S)-Isomer | 186692-45-5 | Cyclin-dependent kinase (Cdk) inhibitor | III | Proliferation and Apoptosis | | CD4 |
| PAC-1 | 315183-21-2 | Procaspase-3 activating compound; | III | Proliferation and Apoptosis | | CD4 |

TABLE 2-continued

Agents For T Cell Modulation In Adoptive Cell Therapies

| Compounds | CAS Number | Compound Information | Group | Group Descriptor | CD8 Hit | CD4 Hit |
|---|---|---|---|---|---|---|
| 8-Quinolinol, 5,7-dichloro- | 773-76-2 | Capitrol; Antibiotic | IV | Anti-infective | CD8 | CD4 |
| Nitrofurantoin | 67-20-9 | Antibiotic | IV | Anti-infective | CD8 | CD4 |
| 8-Quinolinol, 5-chloro-7-iodo- | 130-26-7 | Clioquinol; Antibiotic | IV | Anti-infective | CD8 | CD4 |
| 2-Naphthacenecarboxamide, 7-chloro-4-(dimethylamino)-1,4,4a,5,5a,6,11,12a-octahy | 64-73-3 | Ribosomal protein synthesis inhibitor | IV | Anti-infective | CD8 | |
| Nifuroxazide | 965-52-6 | Nitrofuran antibiotic | IV | Anti-infective | CD8 | |
| Tosufloxacin hydrochloride | 100490-36-6 | Ozex; Fluoroquinolone antibiotic | IV | Anti-infective | | CD4 |
| Sertraline | 79617-96-2 | Zoloft; antidepressant | V | Other | CD8 | CD4 |
| Diethylenetria minepentaacetic acid, penta sodium | 67-43-6 | Iron chelating agent | V | Other | CD8 | CD4 |
| Edrophonium chloride | 116-38-1 | Reversible acetylcholinesterase inhibitor | V | Other | CD8 | |
| BIX01294 | 1392399-03-9 | GLP and G9a histone lysine methyltransferase inhibitor | V | Other | | CD4 |
| Terfenadine | 50679-08-8 | Antihistamine | V | Other | | CD4 |
| dmPGE2 | 39746-25-3 | Prostaglandin molecule | V | Other | | |

TABLE 3

Additional Agents for T Cell Modulation in Adoptive Cell Therapies

| Compounds | CAS Number | Compound Information | Group | Group Descriptor |
|---|---|---|---|---|
| 2-DG | 154-17-6 | Inhibits glycolysis | I | Metabolism & Nutrient Sensing |
| GSK3 Inhibitor | For example-TWS119: 601514-19-6 | GSK3 inhibitor | II | Signaling Pathways |
| HS173 | 1276110-06-5 | PI3K inhibitor | II | Signaling Pathways |
| LY294002 | 154447-36-6 | PI3K inhibitor | II | Signaling Pathways |
| Pictilisib | 957054-30-7 | PI3K inhibitor | II | Signaling Pathways |

Example 3

In Vitro Triage Experiments of the Selected Compounds

In vitro experiments are performed to optimize methods for compound exposure and triage compounds that have detrimental impacts on T cell functions. Initial tests determine optimal dose of individual compounds while also evaluating whether the impact on naïve, stem cell memory, and central memory T cells observed previously are replicated in additional donors. To triage compounds with potential detrimental functional impacts on T cells, in vitro assessments for proliferative capacity, ability to polarize to Th1 and Th17, survival through a cryopreservation/thaw cycle, transduction efficiency, and tumoricidal activity of CAR-transduced T cells are performed. Compounds that reproducibly improve ratio or number of naïve, stem cell memory, or central memory T cells during expansion without significant negative impacts on T cell function are tested in combination and assessed for additive or synergistic effects. Through these assessments, lead candidates or combinations are prioritized for additional testing in vivo.

Example 4

In Vivo Models of Adoptive Cellular Therapy Using the Selected Compounds

To translate the results of the in vitro screening and follow up in vitro triage experiments the lead candidates of the selected compounds are applied to in vivo models of adoptive cellular therapy. Specifically, the impact of small molecule modulation is interrogated on adoptive cellular therapy in regards to engraftment, tumoricidal activity, secondary tumoricidal responses, migration, cellular persistence, and graft-versus-host disease. Other readouts which are hall marks of durable adoptive cellular therapy that have been found to correlate with efficacious responses in the clinic are also interrogated.

These experiments are conducted either in a humanized system, in which human cells are adoptively transferred into immuno-deficient NSG mice bearing human tumors, or in a surrogate murine model, in which an immuno-competent animal bears a syngeneic tumor and is treated with syngeneic cellular therapy.

In either the surrogate or humanized model system, mice are injected with a luciferized lymphoma or other tumor of interest. Soon thereafter, the adoptive cellular therapy which has been pre-treated with vehicle or modulating compounds disclosed herein is administered. Dose of both the cell therapy and tumor is optimized to enable a window in which positive or detrimental effects of the compound treatment can be observed. The animal weight, plasma cytokine concentrations, abundance of tumor and adoptive cellular therapy in peripheral blood, secondary lymphoid organs and tumor mass; tumor burden, tumor metastasis, and phenotype of the cellular therapy are monitored for the duration of the experiment.

Compounds that are able to ameliorate one or many tumor-related parameters in vivo have expected effects including, but not limited to, decreasing the cellular therapy dose required for effective tumor clearance, increasing the persistence of adoptive cellular therapy in the peripheral blood, enhancing migration to tumor sites, and/or increased survival against challenge with high tumor dose.

Example 5

Selective Expansion of NK Cells and Subpopulations Thereof Using GSK3 Inhibitor

Figure 2:
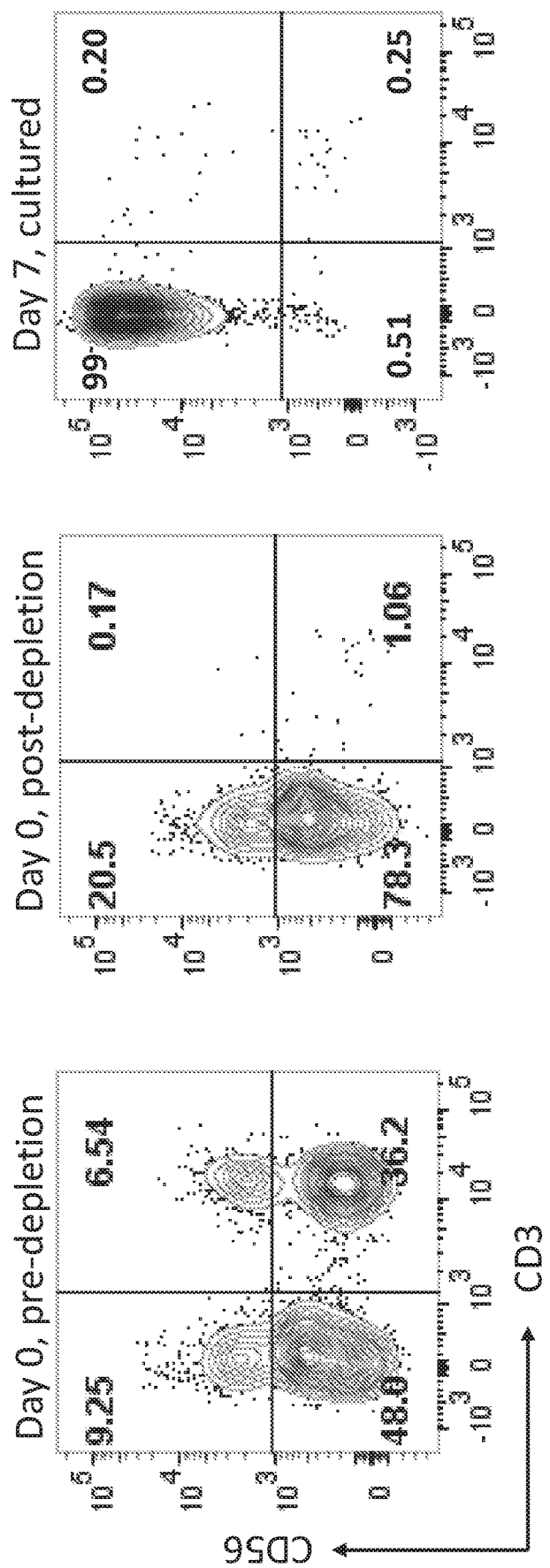
FIG. 2 is a graphic representation showing that the multi-day culture process selectively expands PBMC derived NK cells and not T cells. Percentage of CD56+ and CD3+ cells from apheresis product before (left) and after depletion (middle) and after 7 day culture with IL-15 (10 ng/mL) plus 5 µM CHIR 99021 (right) were shown.

One aspect of the present invention is to provide a method and a system to culture, expand and/or modulate NK cells for adoptive cell therapy. In some embodiments, the method and system for culturing, expanding and/or modulating NK cells is without the use of feeder cells, or feeder cell conditioned medium. Peripheral blood mononuclear cells (PBMC) were isolated from healthy adult donors. The isolated apheresis product (Day 0, pre-depletion; FIG. 2A) was T and B cell depleted using anti-CD19 and CD3 antibodies without pre-depletion culturing (Day 0, post-depletion; FIG. 2B). The post-depletion cell population was then cultured in a feeder free condition with the presence of recombinant human IL-15 (10 ng/mL) and 5 µM CHIR99021, a GSK3 inhibitor, for about 3 to 7 days. As shown, the culture with IL-15 and GSK3 inhibitor appears to selectively and significantly drive NK cell (CD56+CD3−) expansion from about 20% (FIG. 2B) to about 99% on Day 7 culturing (FIG. 2C). In contrast, the remaining T cells (CD56−CD3+) in the post-depletion population (about 1%; FIG. 2B) were not expanded, resulting in a reduced percentage in the population (to 0.25%; FIG. 2C).

After depletion and overnight culture (Day 0, post-depletion; overnight cultured with IL15 only; also referred to as "primed"), the cell population contains approximately 10-40% (due to donor variability) NK cells. The selective and significant expansion of NK cells after culturing with cytokine and GSK3 inhibitor for 7 days resulted in a highly improved NK cell purity of about 80% to more than about 99% (FIG. 3A), representing a NK cell number increase on average of about 8 fold (FIG. 3B), with some samples having a larger increase, of about 18 fold. Note that donor variation and process variation may contribute to variability.

Figure 3:
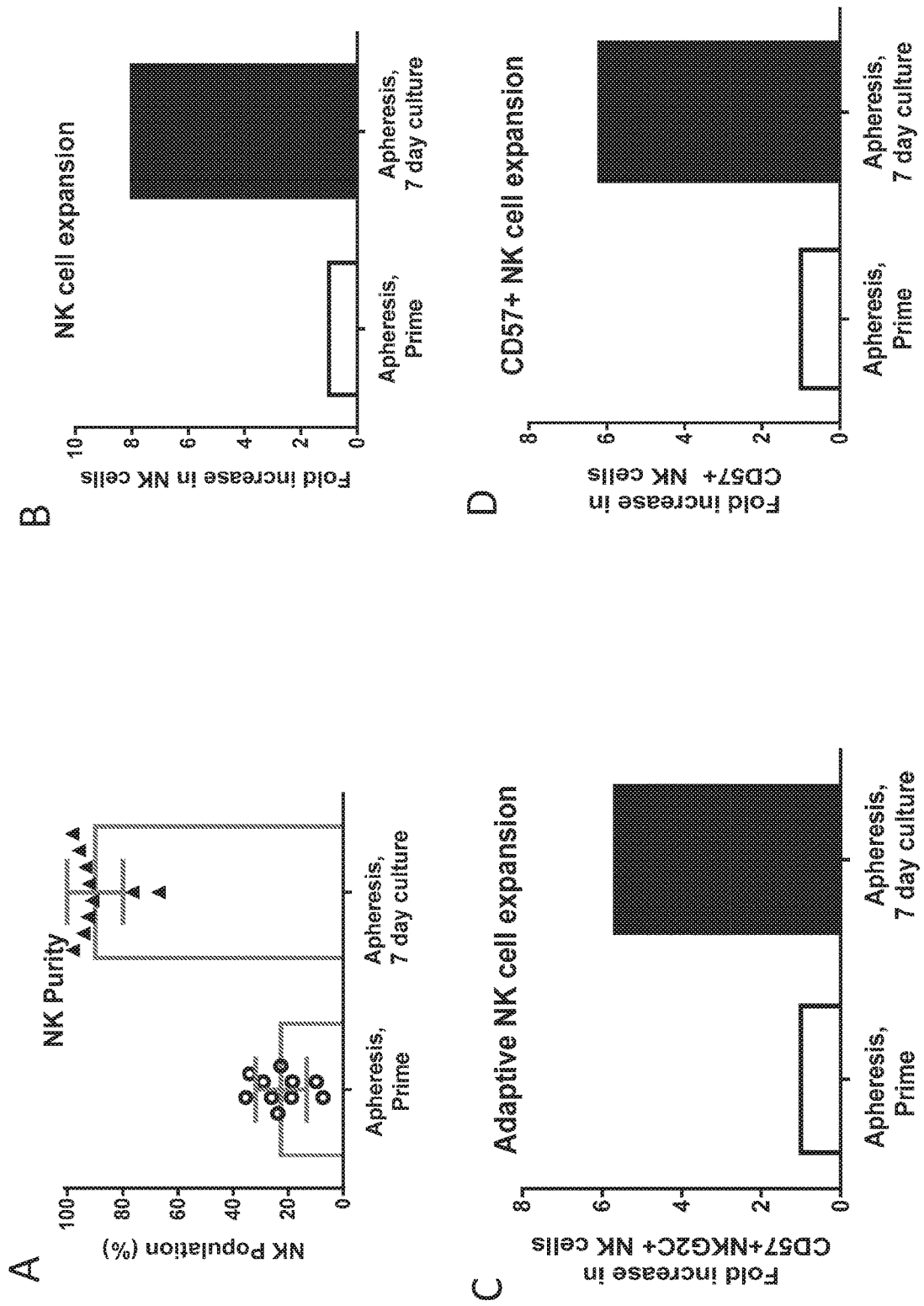
FIG. 3 is a graphic representation showing that the multi-day GSK3i culture process increases the purity, number of total NK cells and number of adaptive NK cells relative to current processes.

The NK cell subpopulations in the overnight primed cell population, and the NK cell subpopulations in the Day 7 GSK3i cultured cell populations were further analyzed and compared. These analyses illustrate that the cell number of CD57+NKG2C+ and CD57+ NK subsets have increased on average about 5-6 fold after culturing with a GSK3 inhibitor (FIGS. 3C and 3D). Typically, CD57+ and CD57+NKG2C+ NK subsets exist in a relatively small number in donor derived samples. Moreover, it was shown that CD57+ and CD57+NKG2C+ NK subsets were not well maintained when cultured under cytokine only (7 day culture without GSK3i; FIG. 4A), which was further represented by the reduced percentage of CD57+ NK cells in the NK population (FIG. 4B). In comparison, when cultured with GSK3 inhibitor, the CD57+ and CD57+NKG2C+ NK cell numbers were significantly increased on an average of 7-8 fold in comparison to those cell numbers when cultured without GSK3i (FIG. 4A). Further, 7 day culture with GSK3i also resulted in an increased percentage of CD57+ cells in the total NK populations in comparison to 7 day culturing without GSK3i (FIG. 4B). The data herein demonstrated that a traditional culturing process (i.e. using cytokine without GSK3 inhibitor) of NK cell population, and particularly when the NK cells are comprised in a donor derived PBMC population without T and/or B cell depletion, would diminish, or even eliminate CD57+ and CD57+NKG2C+NK subsets from the population.

Example 6

GSK3 Inhibition Drives Maturation of NK Cells

Figure 5:
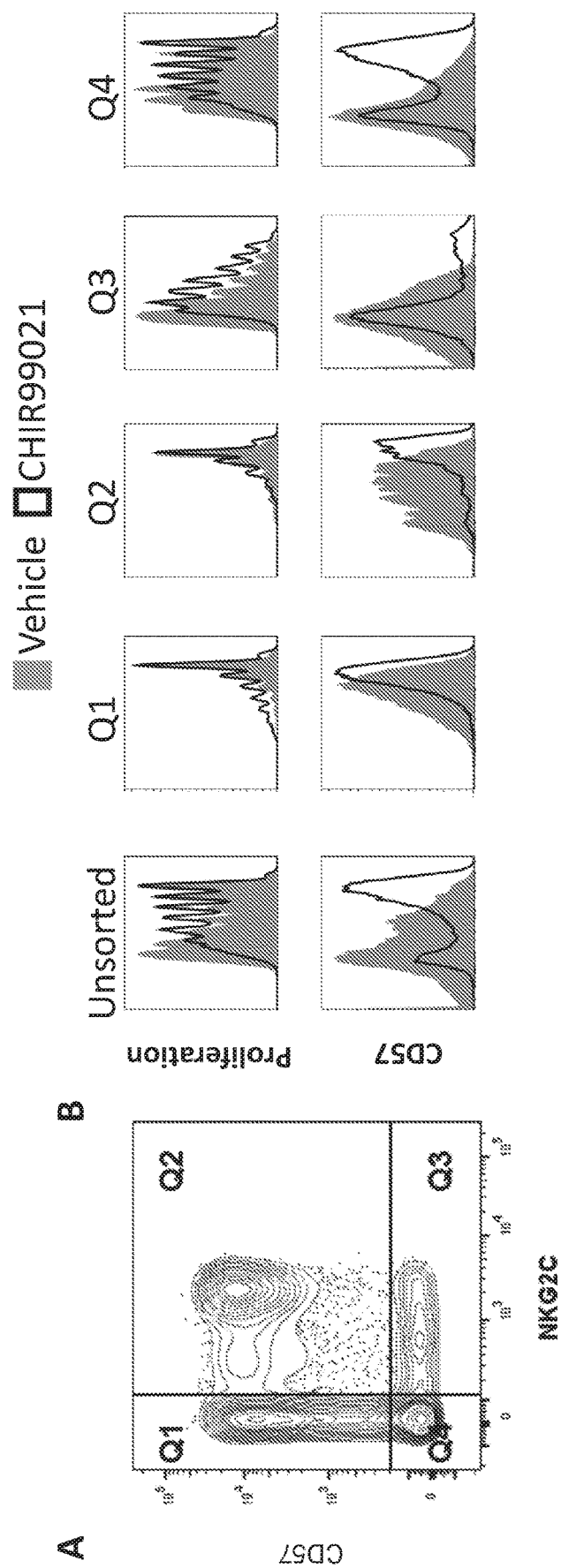
FIG. 5 is a graphic representation showing that GSK3 inhibition drives maturation of immature NK cells. A. Gating strategy and the cell quadrants after the 7 day GSK3i culture period. B. Cell proliferation and cell surface marker expression in each cell quadrant.

CD3/CD19 depleted PBMC were labelled with e450 proliferation dye, and CD56+CD3− NK cells were sorted in bulk or were sorted into 4 populations based on expression of CD57 and NKG2C expression (FIG. 5A). Total, unfractionated, NK cells were cultured alongside CD57+NKG2C− (Q1), CD57+NKG2C+ (Q2), CD57−NKG2C+ (Q3), CD57−NKG2C− (Q4) sorted NK cells with either (1) cytokine (10 ng/ml IL15) and 5 µM CHIR99021, or (2) cytokine only with vehicle control (for example, DMSO only) (FIG. 5B) with autologous CD14+ monocytes in a 1:1 ratio of NK cells:monocytes. After the 7 day culture period, cultures of each sorted population were stained for flow cytometry and analyzed for proliferation and cell surface marker expression. It was shown that there was a significant increase of CD57 expression in the total NK cells after the 7 day culturing with GSK3 inhibitor (FIG. 5B, lower panel of Unsorted). When analyzing each cell quadrant, the increased CD57 expression appeared to be not solely accounted for by the observed enhancement of proliferation of CD57+ cells (FIG. 5B, Q1 and Q2). It was further discovered that the upregulated expression of CD57 in the Q3 and Q4 sorted cells, which were CD57− before culturing with GSK3 inhibitor, underwent maturation and largely contributes to the increased CD57 level (FIG. 5B, Q3 and Q4). It was therefore concluded that GSK3 inhibitor drives NK cell maturation as indicated by upregulation of CD57 expression in CD57− cells, which also contributes to the significantly increased percentage of CD57+ and CD57+NKG2C+ NK cells in the population modulated with GSK3i.

It was further observed that when the same CD3/CD19 depleted PBMC sample underwent treatment with GSK3 inhibitor for a short term, for example, for a period of 16 hours, GSK3 inhibitor did not generate a higher frequency of CD57+ cells in the culture (FIG. 11A), which is comparable to the vehicle treatment. The quantification of CD57+ NK cell fraction in culture with or without GSK3i is further demonstrated in FIG. 11B, in which GSK3i was shown to drive the generation of a modulated NK cell population with a higher frequency of CD57+ fraction when the NK cell population is treated with GSK3i for a time sufficient that is more than 16 hours.

Highly stable expression of CD57 likely is the late stage in NK cell maturation. Compared with CD57$^-$ cells, CD57$^+$ NK cells are potentially less proliferative in response to IL-2 and IL-15 and believed to produce less IFN-γ in response to IL-12 and IL-18. Therefore, it is surprising to discover that the modulation of NK cells using a composition comprising GSK3 inhibitor for a sufficient length of time drives CD57-skewing towards CD57+, while both the number and ratio of CD57+ NK cells improved after modulation, and with enhanced NK cellular cytotoxicity and cytokine response, as further described below.

Example 7

GSK3 Inhibition Enhances NK Cellular Cytotoxicity and Cytokine Response

Figure 6:
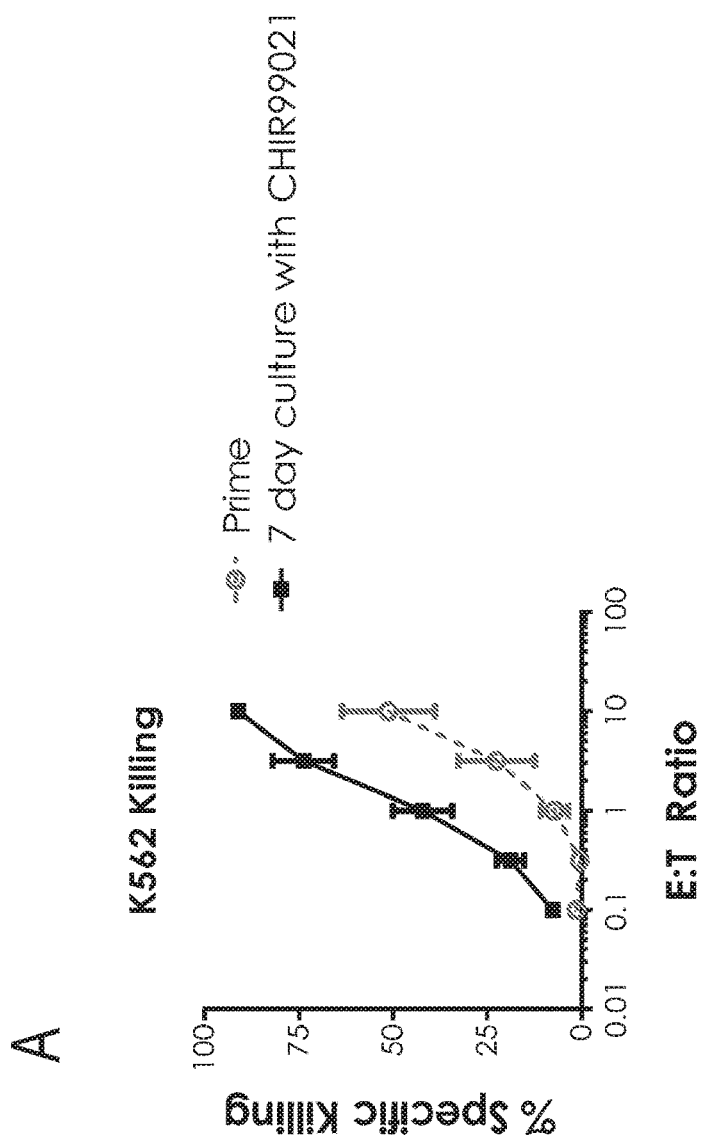
FIG. 6 is a graphic representation showing that GSK3 inhibition enhances cellular cytotoxicity. A. K562 cell specific killing. B. Raji cell specific killing. C. and D. NK cells cultured with GSK3 inhibitor have increased killing kinetics of SKOV-3 cells. E. GSK inhibition expanded adaptive NKs enhanced killing of SKOV3 that further synergized with Her2 ADCC. F. and G. 7 Day GSK3 inhibitor treatment enhances ADCC-mediated killing of A549 cells.
Figure 6:
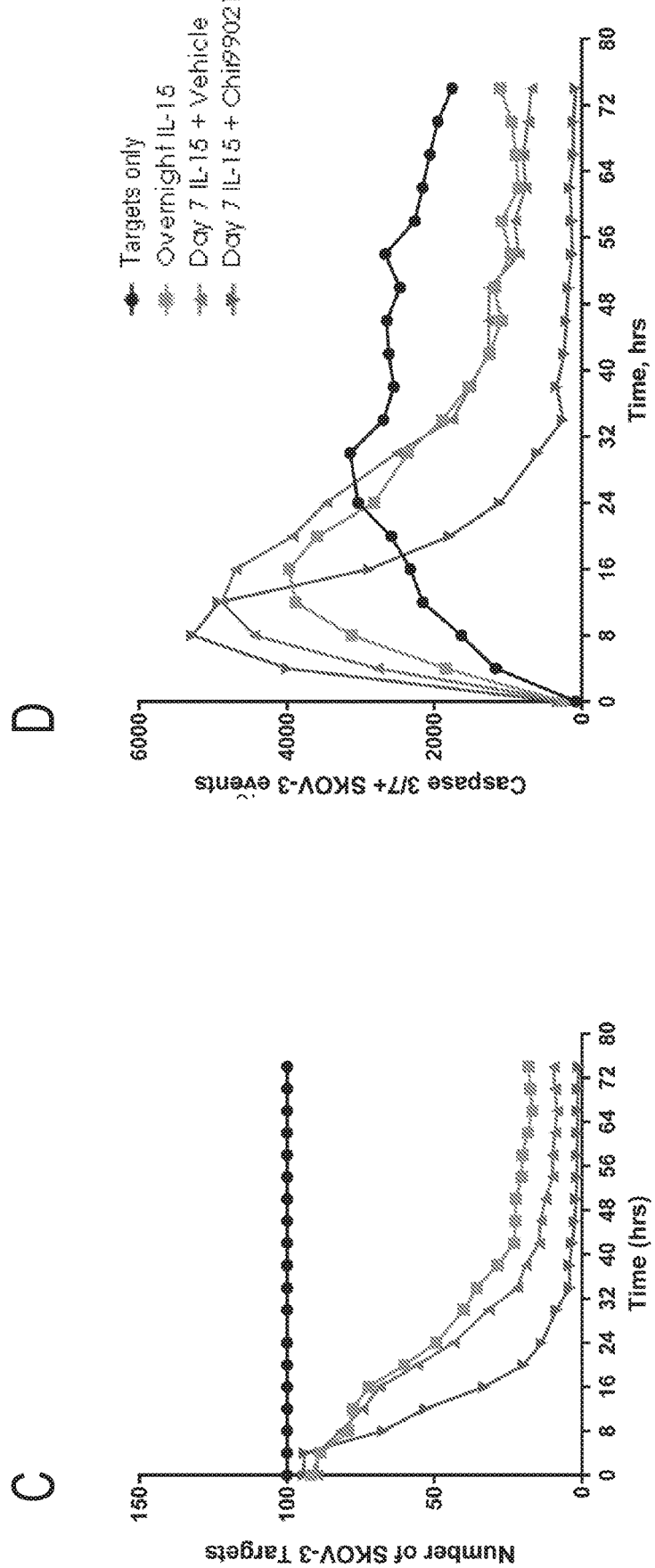

The ability of GSK3 inhibition to enhance cytotoxicity of NK cells isolated directly from donors was assessed using in vitro killing assays. C3/C19 depleted PBMC population was treated overnight with 10 ng/mL IL-15 only (primed), or a 7 day culture combination of 10 ng/mL IL-15 and 5 μM CHIR99021. The target cells for the killing assays included K562 cells, CD20+ Raji cells, HER2+ SKOV3 cells and HER2+ A549 cells. The E:T (Effector:Target) ratio applied to each assay ranged from 0.1, 0.5, 1, 5 to 10. After the target cells were incubated with the differently treated NK cells for 4 hours, the respective percentage of specific killing (target cell lysis) was calculated. In the K562 killing assay, the $E:T_{50}$ (E:T ratio when there is 50% of target cell lysis) for NK cells treated with IL15 only was about 10, whereas the $E:T_{50}$ for GSK3i and IL15 treated NK cell was reduced to about 1, representing an greatly improved cytotoxic activity (FIG. 6A). Raji cells are less prone to NK mediated cytotoxicity. FIG. 6B shows that while Raji cells are still quite resistant to overnight IL-15 treated NK cells, with an $E:T_{50}$ almost as high as 100, after treating the NK cells with IL15 in the presence of GSK3i for 7 days, the $E:T_{50}$, however, was dramatically reduced to 1-2, demonstrating a significant effect of the combination of IL15 and GSK3 inhibitor in increasing NK cell cytotoxicity to even kill resistant cells.

In a similar fashion, SKOV3 cells were treated with NK cells derived from overnight culture with IL15, 7 day culture with IL15 and 7 day culture with IL15 and GSK3i. The data shows that based on cell killing as indicated by elimination of SKOV3 cells (FIG. 6C) and earliest maximal peak of caspase 3/7 events (apoptosis) (FIG. 6D), the NK cells treated with GSK3i are the most effective in killing the SKOV3 cells in terms of both killing rate and killing efficiency.

Figure 6E:
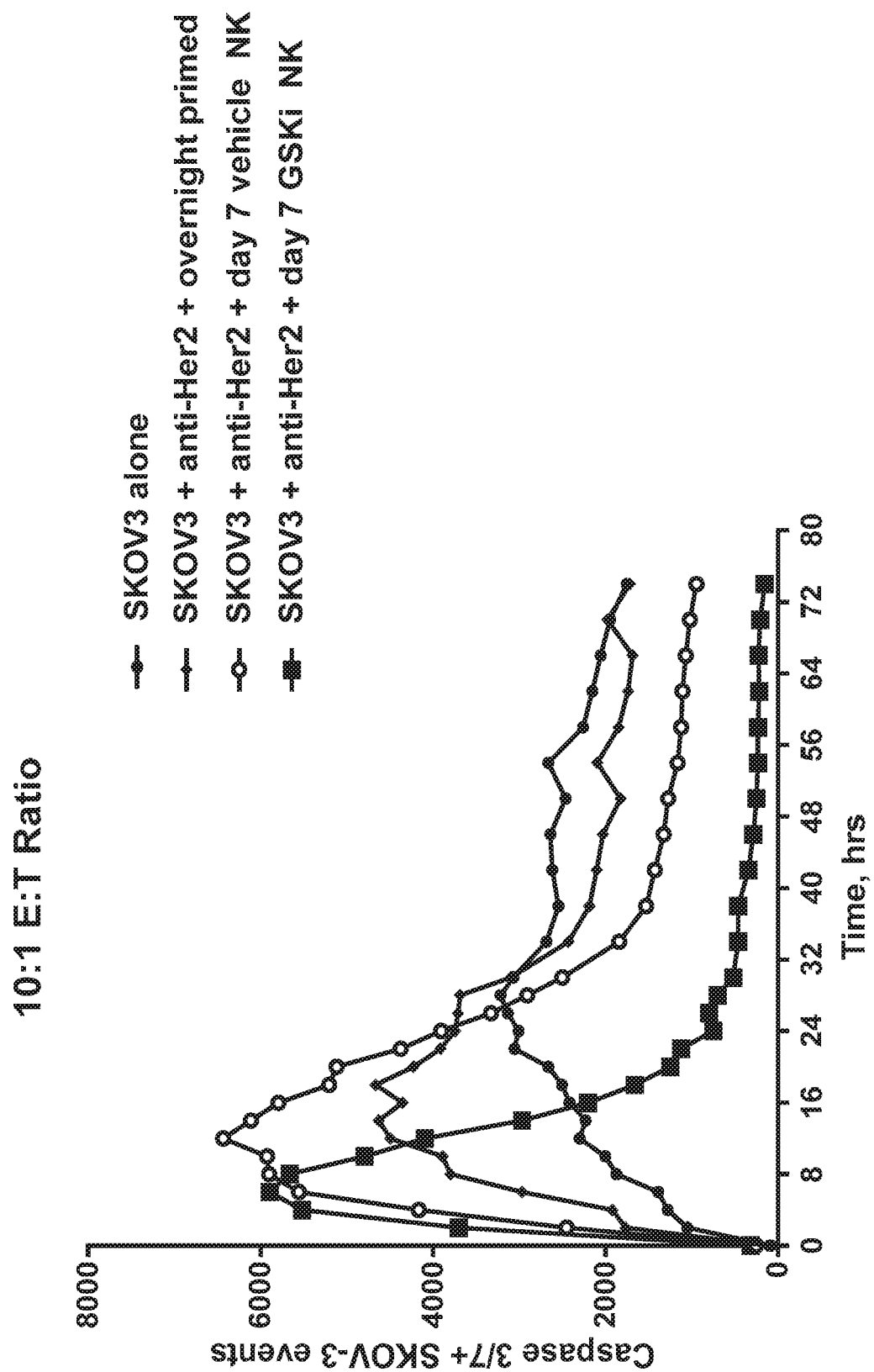
Figure 6F:
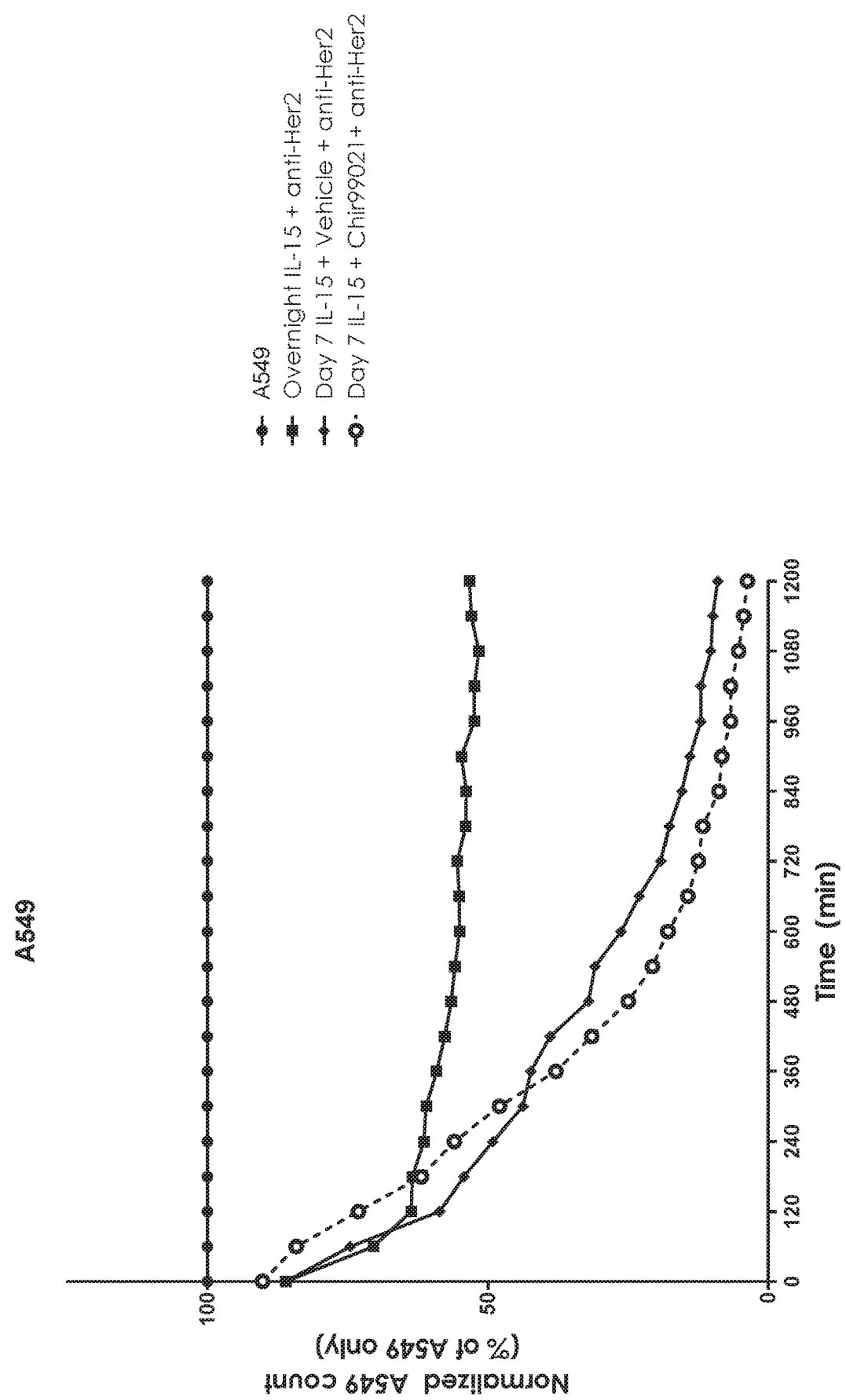
Figure 6G:
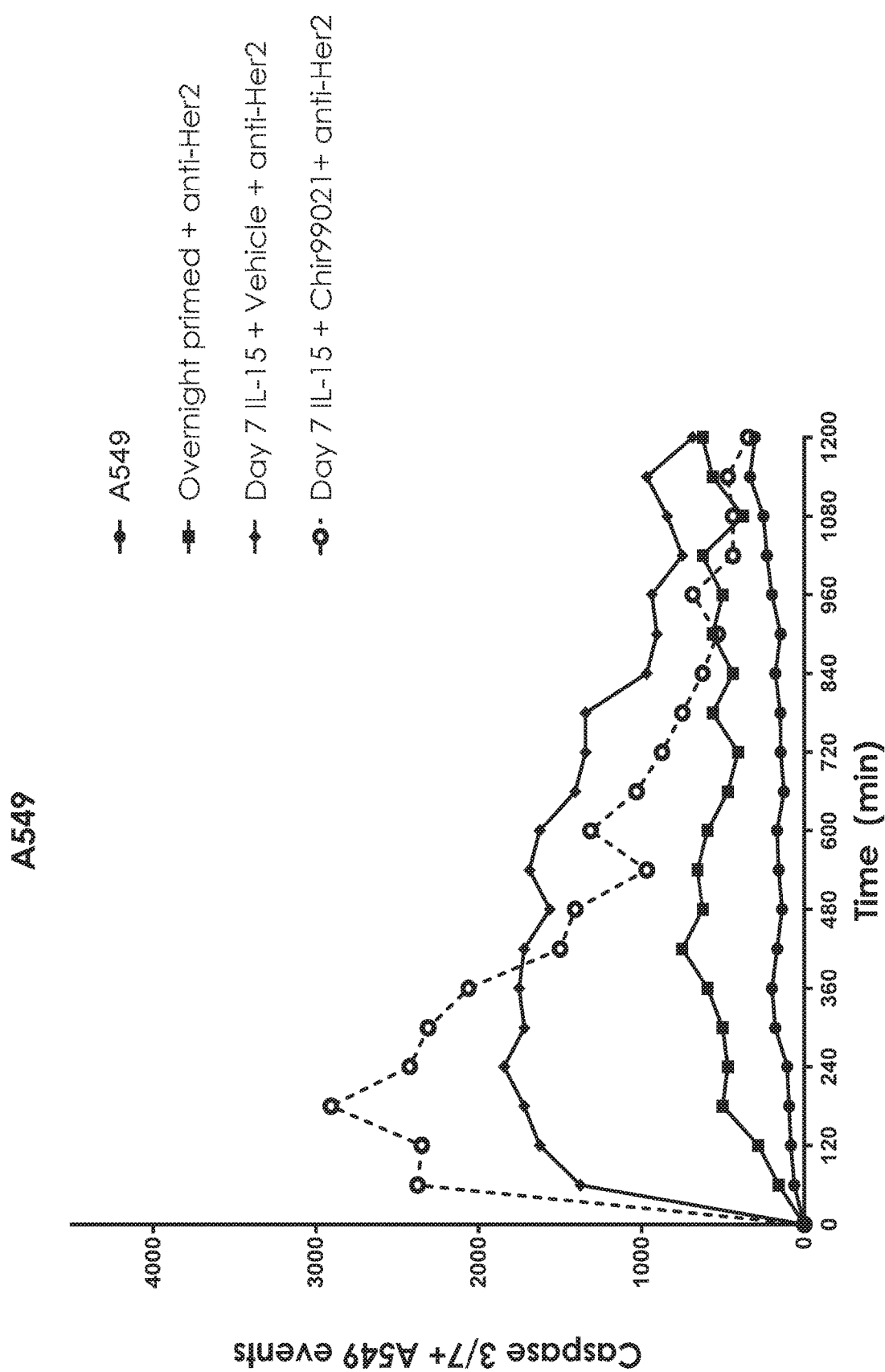

Antibody directed cellular cytotoxicity (ADCC) was also shown to be enhanced with NK cells cultured with IL15 and GSK3i for 7 days when HER2 antibody (Herceptin) was used to mediate the killing of SKOV3, in comparison to ADCC killing using NK derived from overnight culture with IL15 and 7 day culture with IL15 (FIG. 6E). For further demonstration, A549 cell lines (small-cell lung cancer lines) having high expression of the HER2 antigen, which can be targeted by the Herceptin antibody to test ADCC-mediated killing, were applied for testing NK cell killing. Similar enhanced ADCC-mediated cell killing by NK cells cultured with GSK3i for 7 days was observed in both killing rate (FIG. 6F) and efficiency (FIG. 6G) of A549 cell killing. Combined, the data demonstrate that by modulating an NK culture for multiple days in IL15+GSK3i, adaptive and CD57+ mature cells are maintained and expanded, resulting in a significant increase in cytotoxic effect of the NK cells.

Figure 7:
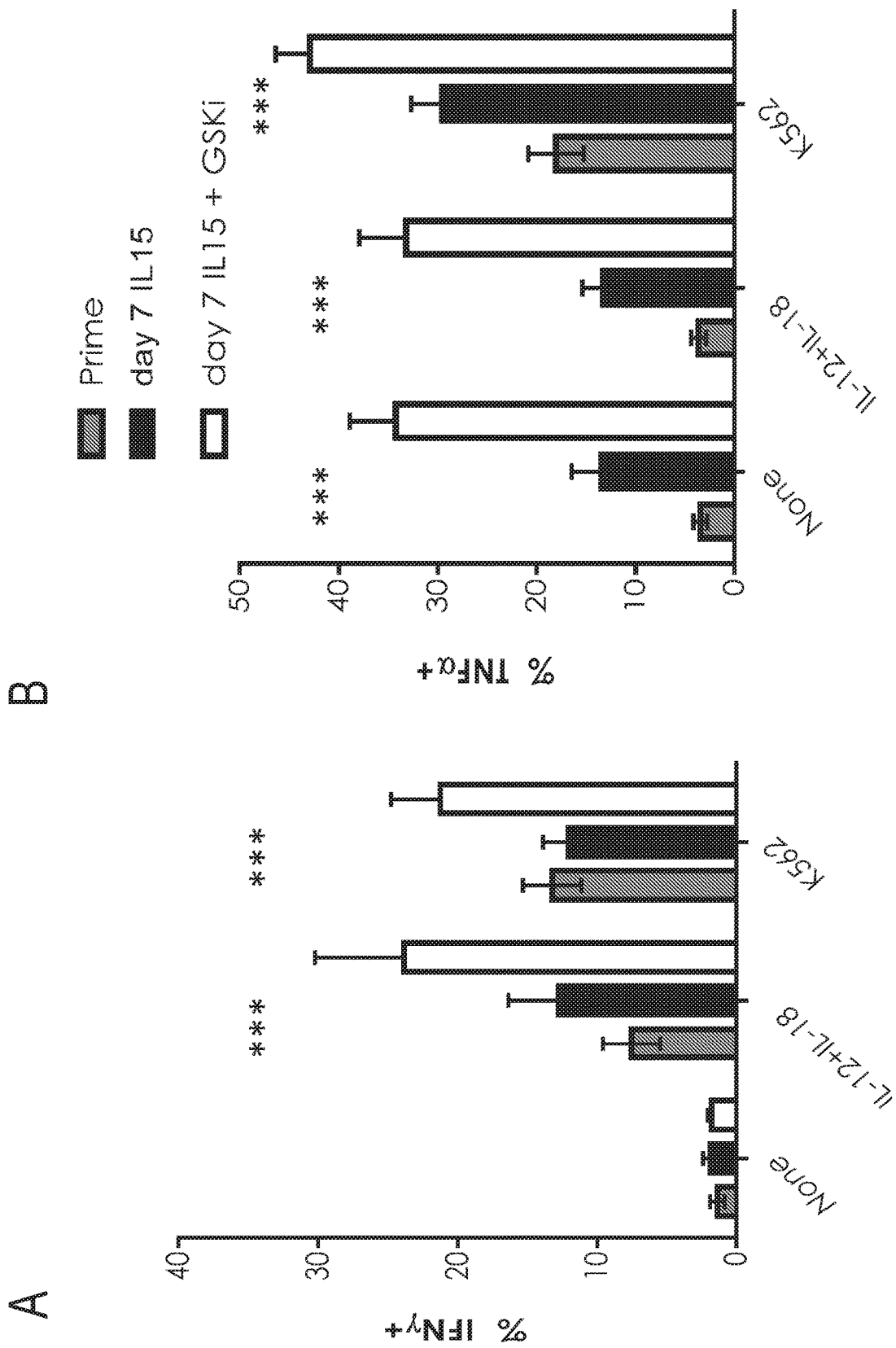
FIG. 7 is a graphic representation showing that GSK3 inhibition enhances NK cell cytokine response. A. IFNγ. B. TNFα.

Also analyzed was the effect of GSK3 inhibitor treatment to NK cell cytokine response. PBMC obtained directly from donors were cultured after CD3/CD9 depletion for 7 days with 10 ng/ml IL-15 and 5 uM CHIR99021, or with IL15 only. On day 7, cells were washed and cultured separately with IL-12 (10 ng/ml) and IL-18 (50 ng/ml), or with K562 cells at a 1:1 ratio for stimulation. After a 4-hour culture period, cells were stained for cell surface antigens and fixed prior to intracellular staining with antibodies to IFNγ and TNFα, respectively. FIG. 7 shows that the IFNγ and TNFα production in the GSK3i and IL15 treated NK cells were enhanced under both IL12+IL18 and K562 stimulation in comparison to primed (depleted, overnight with IL15) or to 7 day IL15 only treated samples. The enhanced cytokine production in GSK3i and IL15 treated NK cells is demonstrated by a significant percentage increase shown in FIGS. 7A (IFNγ) and 7B (TNFα) in comparison to control NK cells (overnight with IL15), and NK cells cultured with IL15 for 7 days. Further, because the response to IL-12 and IL-18 is typically associated with immature NK cells, the above observed enhanced IFNγ and TNFα response supports that the composition and method disclosed herein lead to enhanced functions associated with both mature NK (cytotoxicity) and immature NK (cytokine responsiveness) in CD3/19 depleted PBMC obtained directly from donors.

Example 8

GSK3 Inhibitor Effecting NK Proliferation and Subtype Skewing in the Presence of Modified K562 Feeder Cells It was observed that the co-culturing of NK cells with K562 feeder cells using the process disclosed herein, i.e., depleting the PBMCs on Day 0, and then culturing the NK cells in the presence of GSK3i for multiple days, allows for a significant increase in selective NK cell subset expansion with enhanced functionality over feeder-free culture. Unmodified and modified K562 cells (for example, with transgene mediated surface expression of certain proteins) were tested and demonstrated a similar outcome in selective NK proliferation and subtype skewing by an immediate depletion of a donor sample without pre-depletion culturing followed by GSK3i culturing through multiple days.

Figure 8:
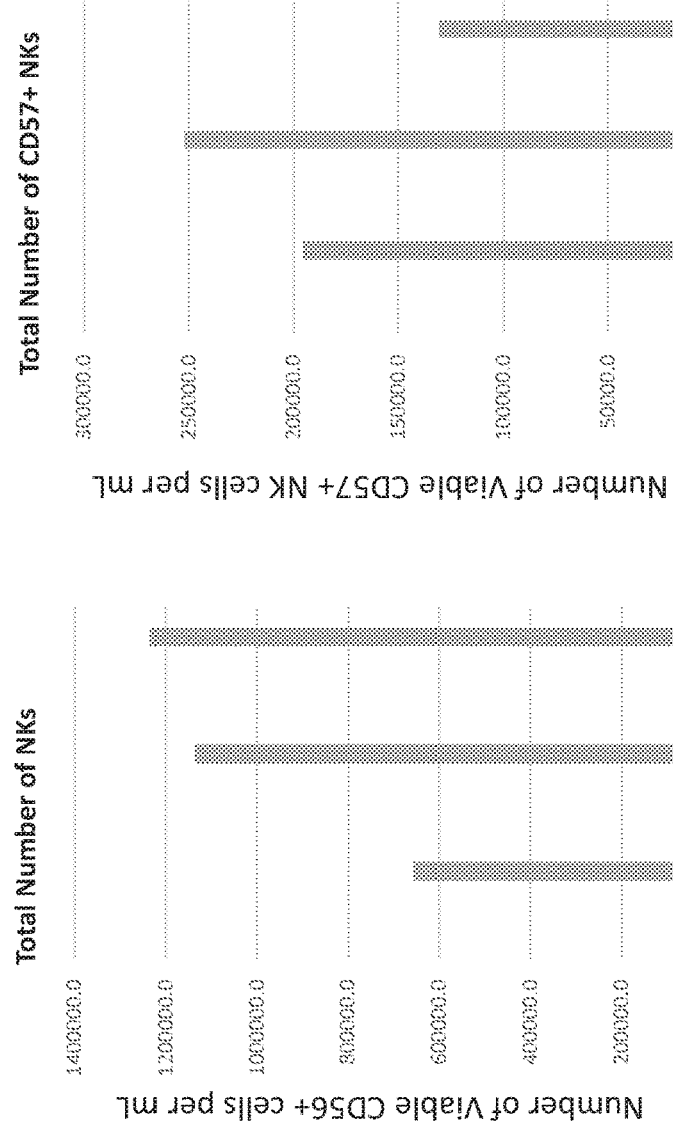
FIG. 8 is a graphic representation showing that GSK3 inhibition and combination GSK3i/MEKi/rapamycin enhance NK proliferation and augment NK subtype skewing in the presence of K562 feeder cells. A. Total number of NK cells. B. Total number of CD57+ NK cells. C. Total number of NKG2C+ NK cells.

CD3/19 depleted PBMCs were cultured for 7 days with modified K562 feeder cells in the presence of DMSO (Vehicle), 0.1 uM GSK3i CHIR99021 alone (C), or a combination of 0.1 uM GSK3i CHIR99021, 40 nM MEKi PD0325901, and 1 nM Rapamycin (CPR). FIG. 8A showed that addition of small molecules (C or CPR) increased proliferation of the activated NK cells overall compared to culturing alone with K562 line modified to express IL21 and 41BBL. In comparison, the increase in the number of CD57+ NK cells was the highest by GSK3i, whereas CPR resulted in lower number of CD57+ NK cells than the vehicle control (FIG. 8B). However, the number of NKG2C+ NK cells was increased with the treatment using CPR (FIG. 8C), when the NK cells were cultured with modified K562 feeder cells.

The data demonstrate that the presence of feeder cells, the unique combination of small molecule(s), when applied according to the presently disclosed process, can augment various features of the expanding NK population, including skewing towards a mature state as indicated by increase in CD57+ population or towards an adaptive state as indicated by increase in NKG2C+ population.

Example 9

Maintenance of Modulated NK Cell Phenotype In Vivo

Figure 9:
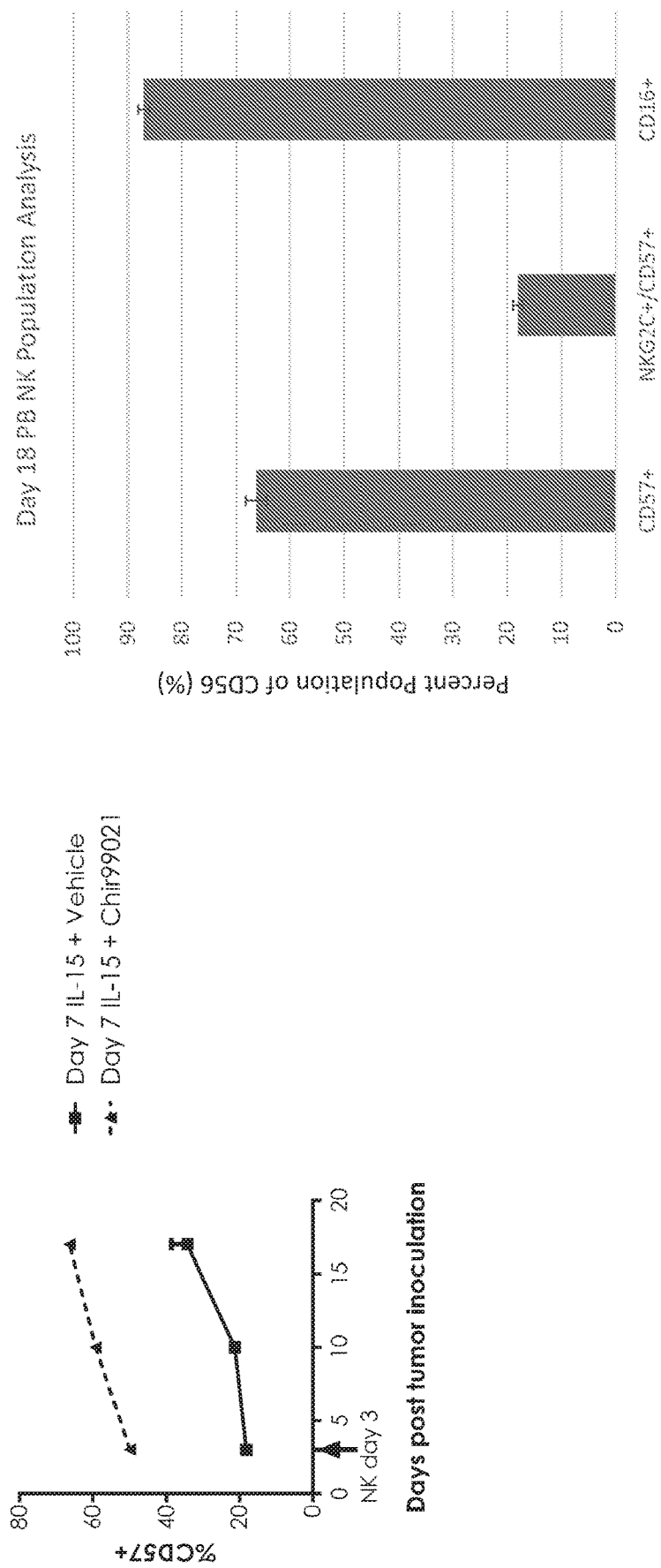
FIG. 9 is a graphic representation showing that NK cells cultured in vitro with GSK3i for 7 days maintain their phenotypic changes in vivo for at least one week after being transferred and without the presence of the small molecule. A. Percentage population of CD57+ cells. B. Percentage population of NK cell subsets.

NK cells cultured overnight with IL15, 7 day culture with IL15 and vehicle, and 7 day culture with IL15 and GSK3i were transferred respectively into NSG mice. 7 days later the NK cells from the peripheral blood of the mice were analyzed for phenotype (n=3 per group). The mice received only IL-15 with no GSK3i. It was shown that NK cells cultured in vitro with GSK3i for 7 days maintain their phenotypic changes in vivo for at least one week after being transferred and without the presence of the small molecule. CD57 remains high representing the maturity of the NK cells which was not the case when the cells were cultured without GSK3i (FIGS. 9A and 9B). Further, CD16, a marker for antibody dependent killing ability, and NKG2C+/CD57+ were maintained in vivo (FIG. 9B).

Figure 10:
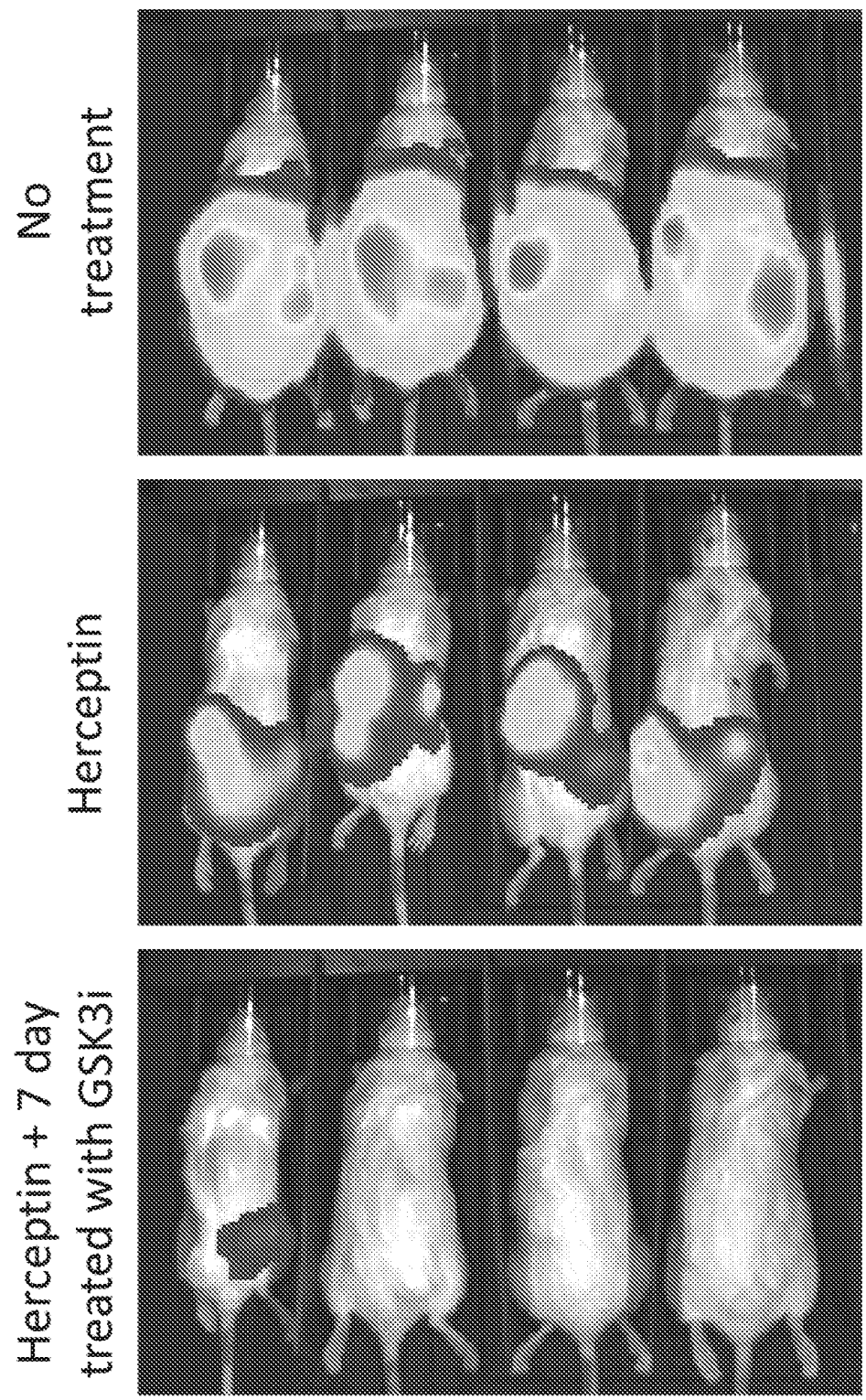
FIG. 10 is a graphic representation showing that in vivo tumor clearance ability of GSK3 inhibitor cultured NK cells.

Moreover, the in vivo tumor clearance ability of GSK3i cultured NK cells using the process provided herein was also tested. NSG mice were irradiated with 300 rads one day prior to intraperitoneal transplant of luciferase-expressing SKOV-3 cells. 5 days after the ovarian carcinoma cell transplant, the mice were either left untreated, treated with Herceptin only, or treated with Herceptin, IL-15, and NK cells cultured for 7 days with IL-15 and CHIR99021. Luciferase-expressing SKOV-3 cells were imaged on Day 21 post-transplant (or 16 days after the treatment) using the IVIS imaging system. FIG. 10 demonstrates the addition of GSK3i treated NK cells enhances the tumor-suppressive effects of Herceptin antibody treatment, suggesting that the GSK3i treated NK cells are capable of mediating antibody-dependent cellular cytotoxicity in vivo. These data suggest that the effect of the multi-day culture with IL-15 and GSK3i is long lasting, and remains imprinted on the NK cells for at least one week following withdrawal of the small molecule, CHIR99021.

Figure 12A:
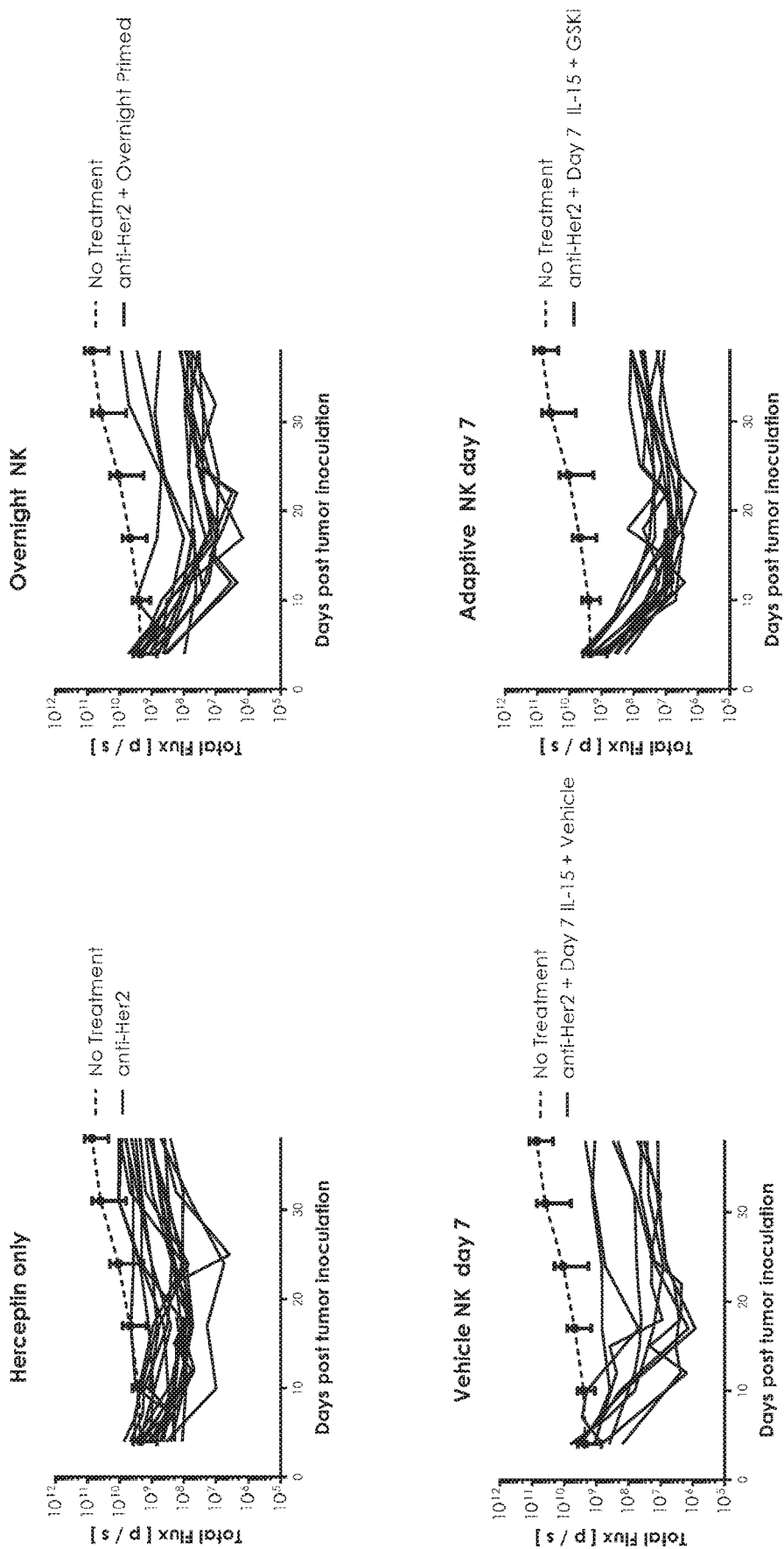
FIG. 12 shows that multi-day GSK3 inhibitor treated NK cells are highly effective in vivo against SKOV-3 cells. A. NK cell ADCC killing assays using Herceptin only, overnight primed NK cells with Herceptin, 7 day vehicle treated NK cells with Herceptin, or 7 day GSK3 inhibitor treated NK cells with Herceptin. B. Comparison of the ADCC killing effect using cells under different treatment.

The in vivo tumor clearance ability of GSK3i cultured NK cells using the process provided herein was then compared to overnight primed CD3/CD19 depleted PBMC, and CD3/CD19 depleted PBMC cultured for 7 days with IL-15 and DMSO. SKOV-3 cells expressing luciferase were injected intraperitoneally into NSG mice. Five days later, mice were treated with 100 ug Herceptin antibody and $2.5 \times 10^6$ cells from either overnight primed CD3/CD19 depleted cells, CD3/CD19 depleted PBMC cultured for 7 days with IL-15 and DMSO (vehicle), or CD3/CD19 depleted PBMC cultured for 7 days with IL-15 and GSK3i (GSK3i modulated NK cells). Luciferase-expressing SKOV-3 cells were quantified by measuring luciferase activity using the IVIS imaging system. FIG. 12A showed that the multi-day cultured NK cells with IL-15 and GSK3i are highly and consistently effective in vivo against SKOV-3 cells. FIG. 12B showed the quantitative comparison of the in vivo SKOV-3 ADCC killing effect by differently treated NK cells, which further confirmed the observation under FIG. 12A.

Figure 13:
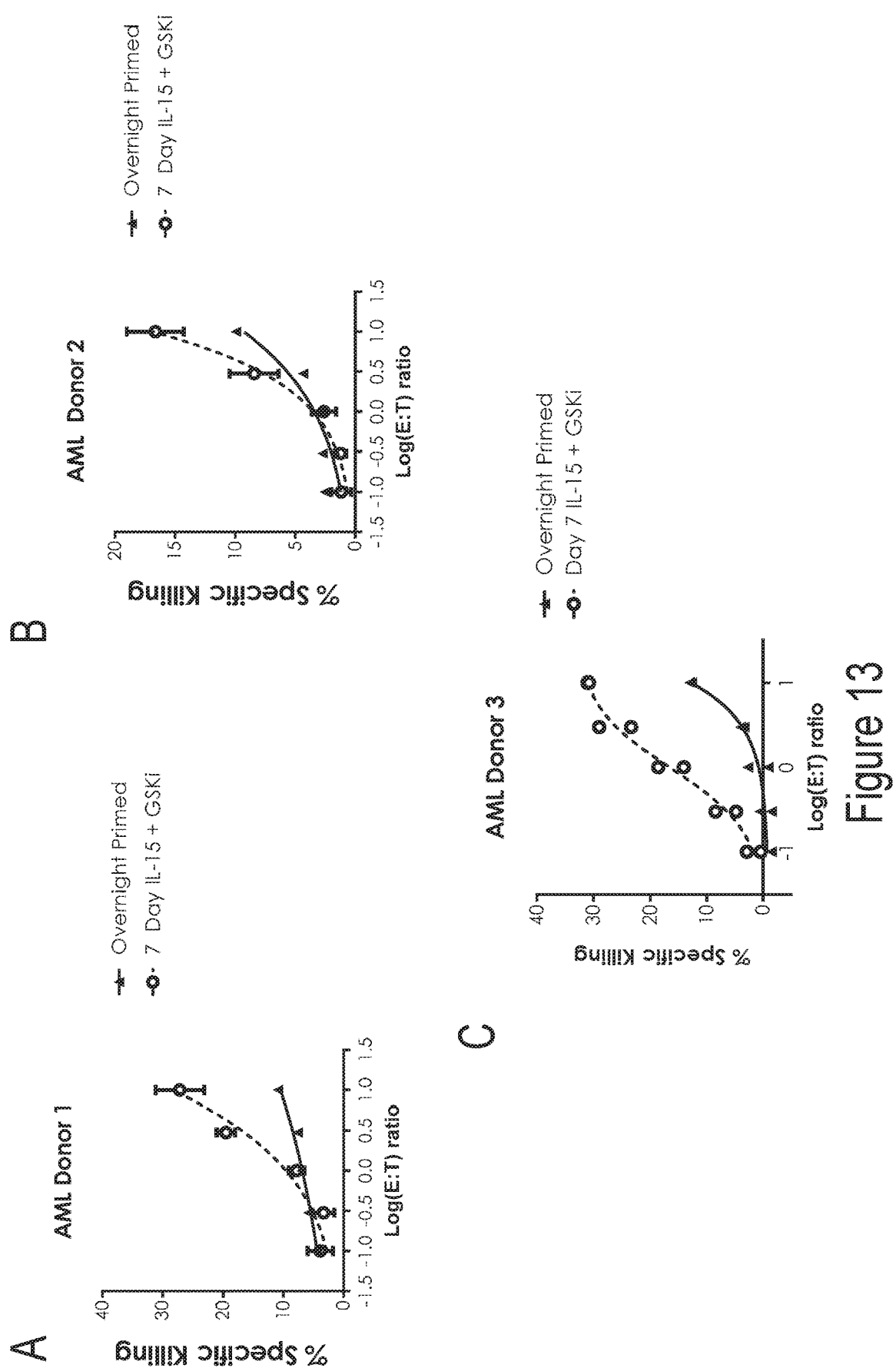
FIG. 13 shows cytotoxicity of multi-day GSK3 inhibitor treated NK cells versus overnight primed NK cells against primary AML blasts: A. AML donor 1; B. AML donor 2; C. AML donor 3.

Cytotoxicity of CD3/CD19 depleted PBMC cultured multiple days with IL-15 and GSK3i (GSK3i modulated NK cells) versus overnight primed NK cells against primary AML blasts were also compared. Percent specific killing of primary AML blasts from multiple patients was measured by flow cytometry-based cytotoxicity assay. FIG. 13 showed that the multi-day cultured NK cells with IL-15 and GSK3i are highly and consistently effective against AML blasts.

Figure 14:
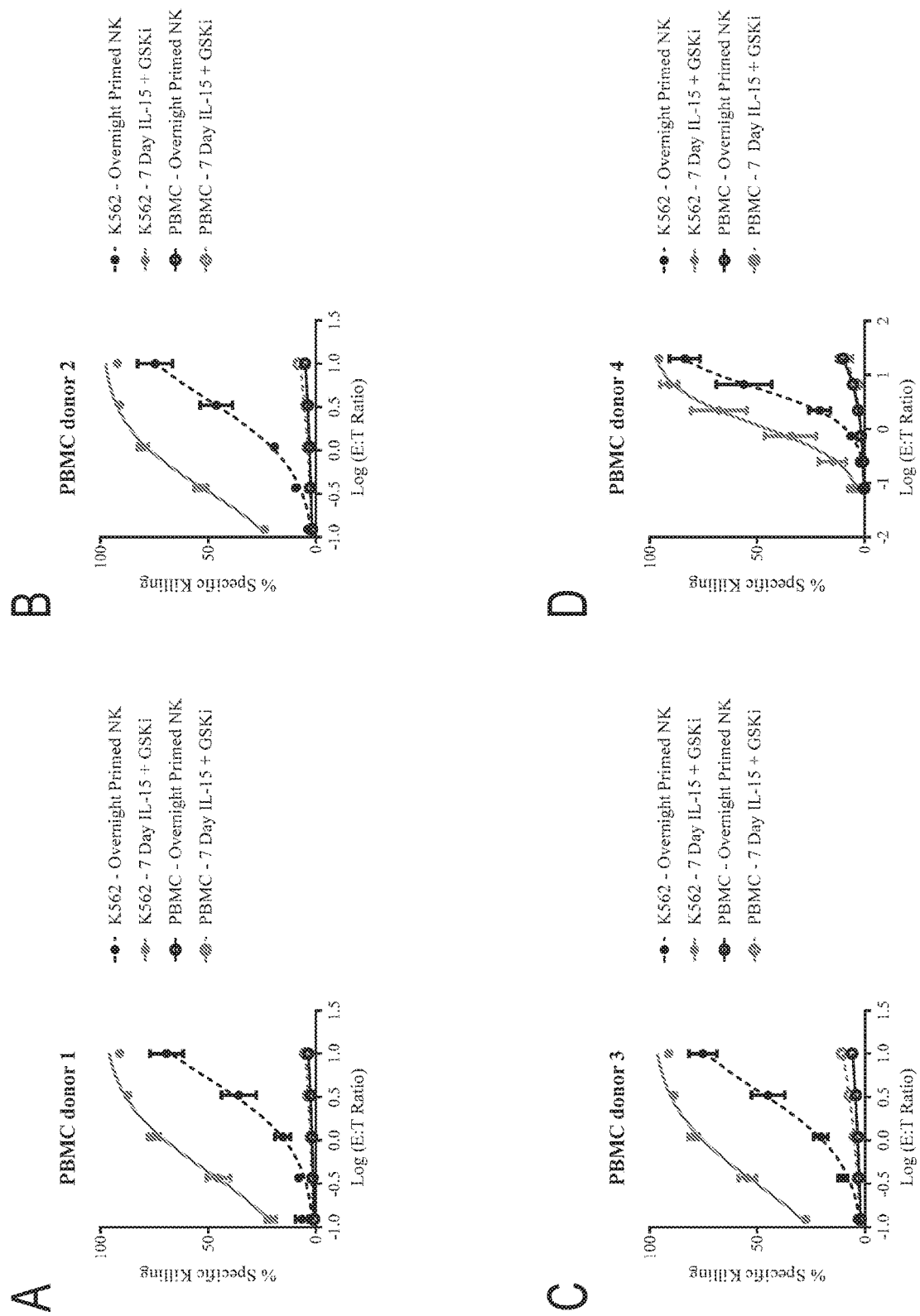
FIG. 14 shows cytotoxicity of GSK3i modulated NK cells against malignant cells but not allogeneic PBMC in a dual-target cytotoxicity assay in which the K562 tumor cells are mixed with PBMCs: A. PBMC donor 1; B. PBMC donor 2; C. PBMC donor 3; D. PBMC donor 4.

Cytotoxicity of GSK3i modulated NK cells against allogeneic PBMC was evaluated in combination with K562 tumor cells in a dual-target cytotoxicity assay. Percent specific killing in PBMC+K562+ overnight primed NK cells or PBMC+K562+ GSK3i modulated NK cells was measured. Data representing the mean±SEM from 4 (FIG. 14A-C) or 3 (FIG. 14D) NK cell donors per healthy PBMC target donor, demonstrating the ability of the GSK3i modulated NK cells to discriminate against malignant cells and selectively target those cells among normal cells.

Example 10

STING Agonist Enhances GSK3i Modulated NK Cell Cytokine Production and Cytotoxicity STING (Stimulator of Interferon Genes) complex plays an important role in detecting the presence of tumor cells and promoting an aggressive anti-tumor response by the body's innate immune system. STING complex works as both a direct cytosolic DNA sensor (CDS) and an adaptor protein in Type I interferon signaling through different molecular mechanisms. STING is expressed in hematopoietic cells in peripheral lymphoid tissues, including T lymphocytes, NK cells, myeloid cells and monocytes. Detection of cytosolic DNA initiates a series of interactions that lead to STING pathway activation. Activating the pathway triggers the production of interferon β and interferon α. STING agonists activate the STING pathway. STING agonists include STING ligands that bind to and activate STING. Known STING agonists include cyclic dinucleotides (CDN) and xanthenone, and analogs and derivatives thereof. CDNs may be synthetic or originated from prokaryotic or mammalian cellsExemplary STING agonists include, but are not limited to, cGAMP, c-di-GMP, c-di-AMP, c-di-IMP, c-di-UMP, cAMP-GMP, R,R dithio-modified CDA compounds (ML RR-S2 CDA and RR-S2 CDA), ML RR-S2 cGAMP, DMXAA (5, 6-dimethylxanthenone-4-acetic acid). Additional CDN analogs, derivatives, and bacterial CDN products will continue to be identified as STING ligands.

Figure 15:
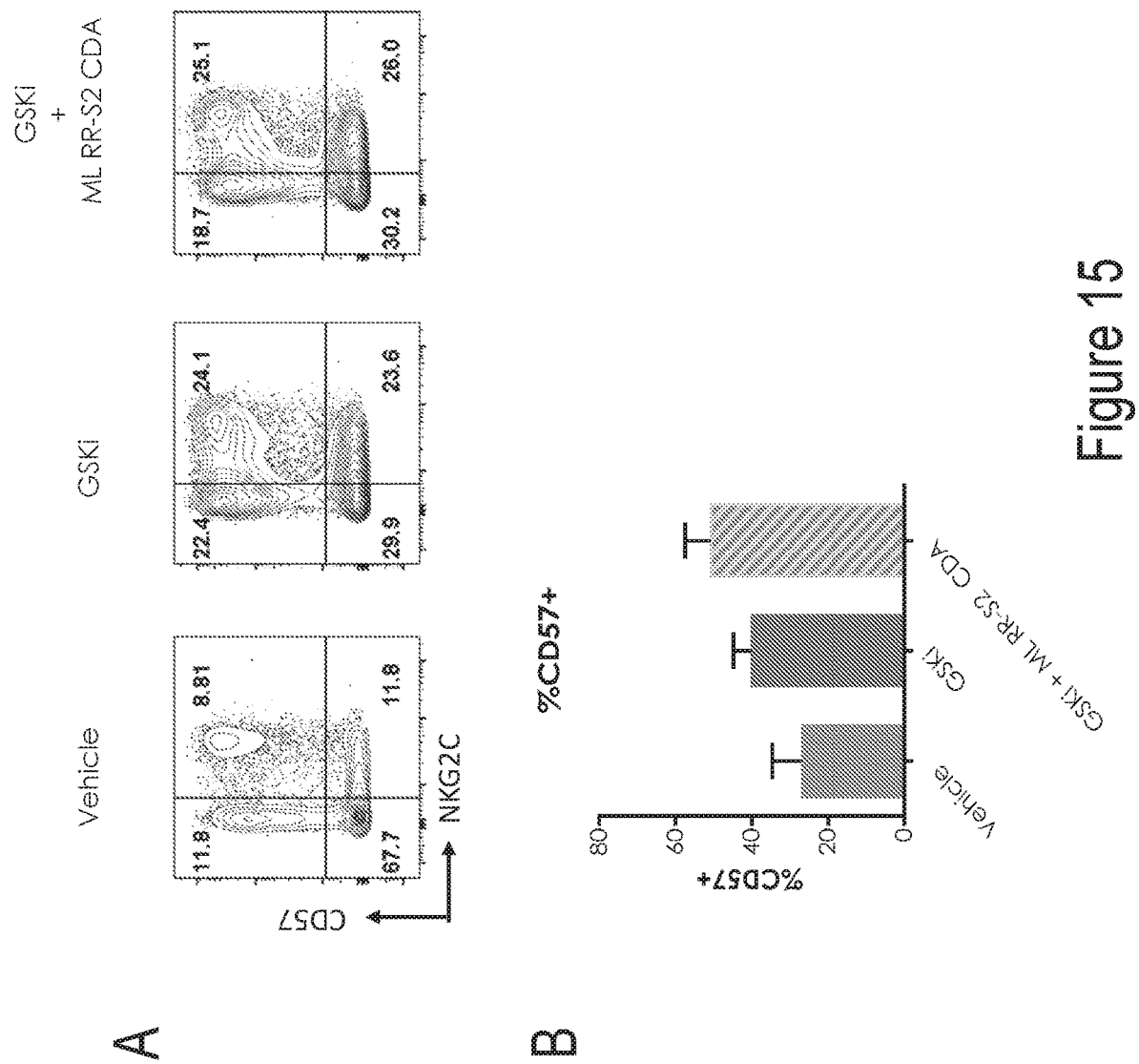
FIG. 15 shows STING agonist ML RR-S2 CDA has limited effect on (A) total CD57+ NK number, and (B) CD57+NKG2C+ NK phenotype.
Figure 16:
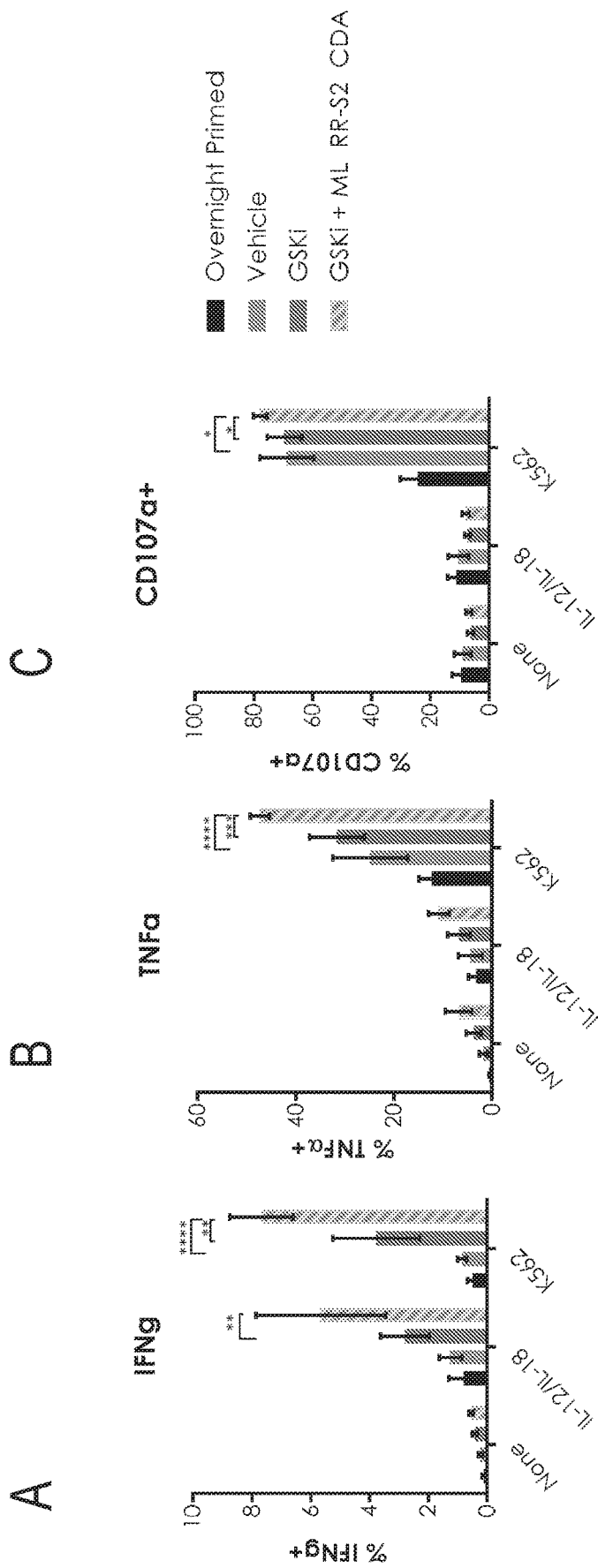
FIG. 16 shows addition of STING agonist in combination with GSK3i enhances NK cell production of A. IFNγ; and B. TNFα for a 4-hour stimulation using IL-12+IL-18 or K562 cells. STING agonist in combination with GSK3i also increases the frequency of CD107a+ NK cells after stimulation (C).

CD3/CD19 depleted PBMC were cultured for 7 days in the presence of 10 ng/ml IL15 and (1) DMSO (vehicle); (2) 5 μM GSK3i (CHIR99021); (3) 1 μM STING agonist (ML RR-S2 CDA); or (4) 5 μM GSK3i+1 μM STING agonist. On day 7, NK cell function and phenotype was assessed by intracellular cytokine staining, cytotoxicity assays, and flow cytometry. STING agonist ML RR-S2 CDA was shown to have limited effect on adaptive NK phenotype and total NK number. FIG. 15 showed that addition of STING agonist to GSK3i+IL-15 NK cell cultures results in continued maintenance of CD57+ fraction with a slight increase over IL-15+ GSK3i culturing. However, as shown in FIG. 16, addition of STING agonist in combination with GSK3i enhances NK cell production of IFNγ (FIG. 16A) and TNFα (FIG. 16B) for a 4-hour stimulation with either IL-12+ IL-18 or with an equal number of K562 cells. The frequency of CD107a+ NK cells after incubation with K562 cells was increased for cells cultured for 7 days with IL-15+ GSK3i+ STING agonist compared to cells cultured with IL-15+ GSK3i only (FIG. 16C). Increased cell surface CD107a expression is associated with enhanced degranulation and cytotoxic potential of NK cells in the presence of STING agonist in combination with GSK3i.

Figure 17:
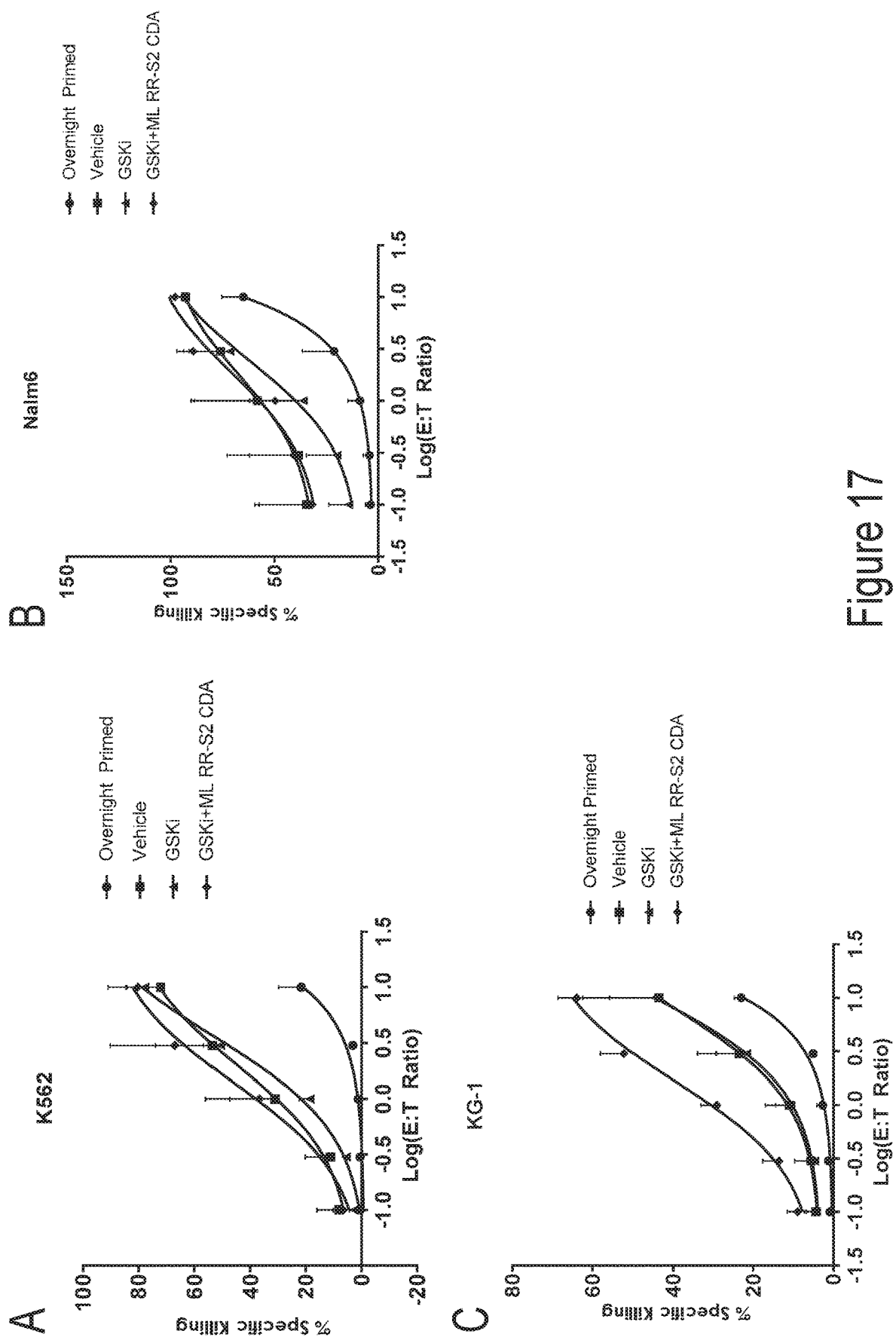
FIG. 17 shows that addition of STING agonist enhanced cytotoxicity of GSK3 inhibitor treated NK in direct killing assay using A. K562, B. Nalm6, and C. KG-1 as target cell.

The ability of STING agonist to enhance cytotoxicity of GSK3i multiday modulated NK cells was assessed using in vitro killing assays. CD3/C19 depleted PBMC population was treated overnight with 10 ng/mL IL-15 only (primed), a 7 day culture with 10 ng/mL IL-15 only, a 7 day culture combination of 10 ng/mL IL-15 and 5 μM CHIR99021, or a 7 day culture combination of 10 ng/mL IL-15, 5 μM CHIR99021 and 1 μM STING agonist. The target cells for the killing assays included K562 cells, Nalm6 cells, and KG-1 cells. The E:T (Effector:Target) ratio applied to each assay ranged from 0.1, 0.3, 1, 3, to 10. After the target cells were incubated with the differently treated NK cells for 4 hours, the respective percentage of specific killing (target cell lysis) was calculated and demonstrated in FIG. 17. In all assays, addition of STING agonist enhanced cytotoxicity of GSK3i modulated NK cells, although to different extent.

Figure 18A:
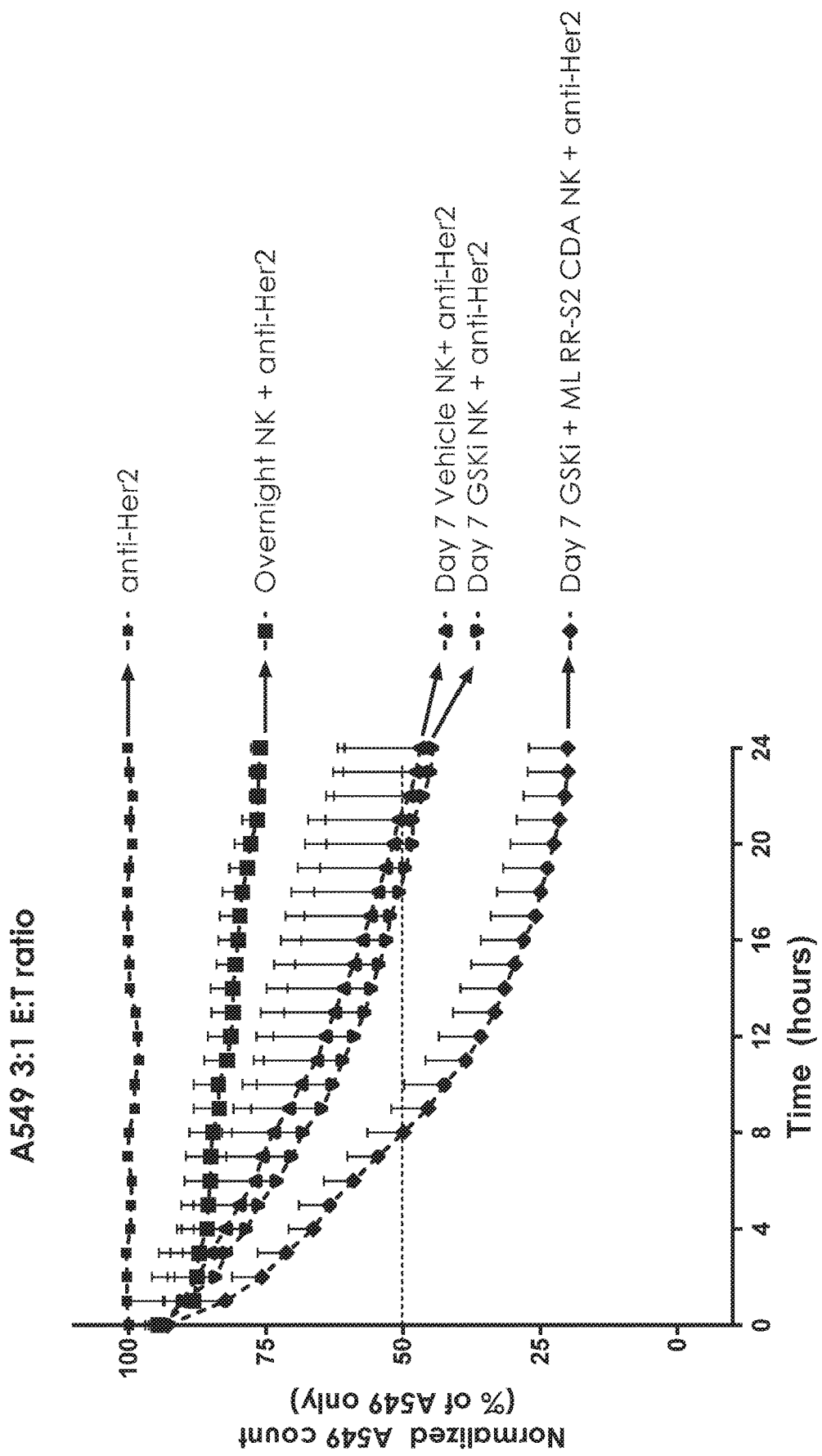
FIG. 18 shows that STING agonist synergizes with GSK3 inhibitor to enhance killing of target cells. Combination of GSK3 inhibitor and STING agonist enhances cytotoxicity of NK cells against A. A549 and B. SKOV-3 target cells in an ADCC assay with anti-Her2 antibody.
Figure 18B:
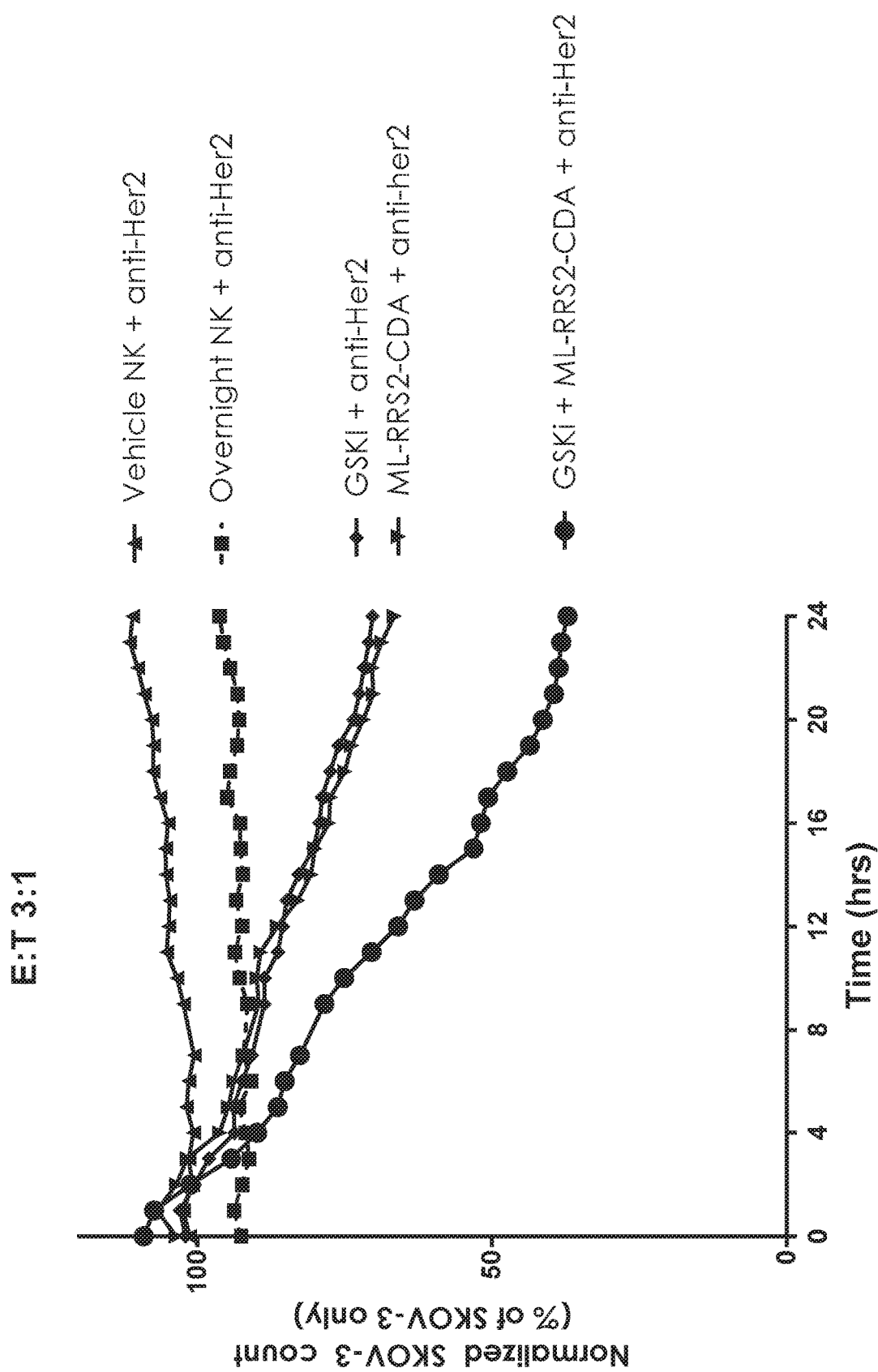

Antibody directed cellular cytotoxicity (ADCC) was also shown to be enhanced with NK cells cultured with STING agonist and GSK3i for 7 days when Herceptin was used to mediate the killing of SKOV3 or A549, in comparison to ADCC killing using NK derived from 7 day culture with GSK3i. NK cells were added to targets at a 3:1 ratio. FIG. 18 showed that a combination of GSK3i and STING agonist in the multiday culture enhances cytotoxicity of NK cells against A549 (FIG. 18A) and SKOV-3 (FIG. 18B) target cells in an ADCC assay with anti-Her2 antibody. FIG. 18B also shows that the combination of STING agonist and GSK3i is more effective in enhancing cytotoxicity of NK cells than either modulator used alone.

Figure 19:
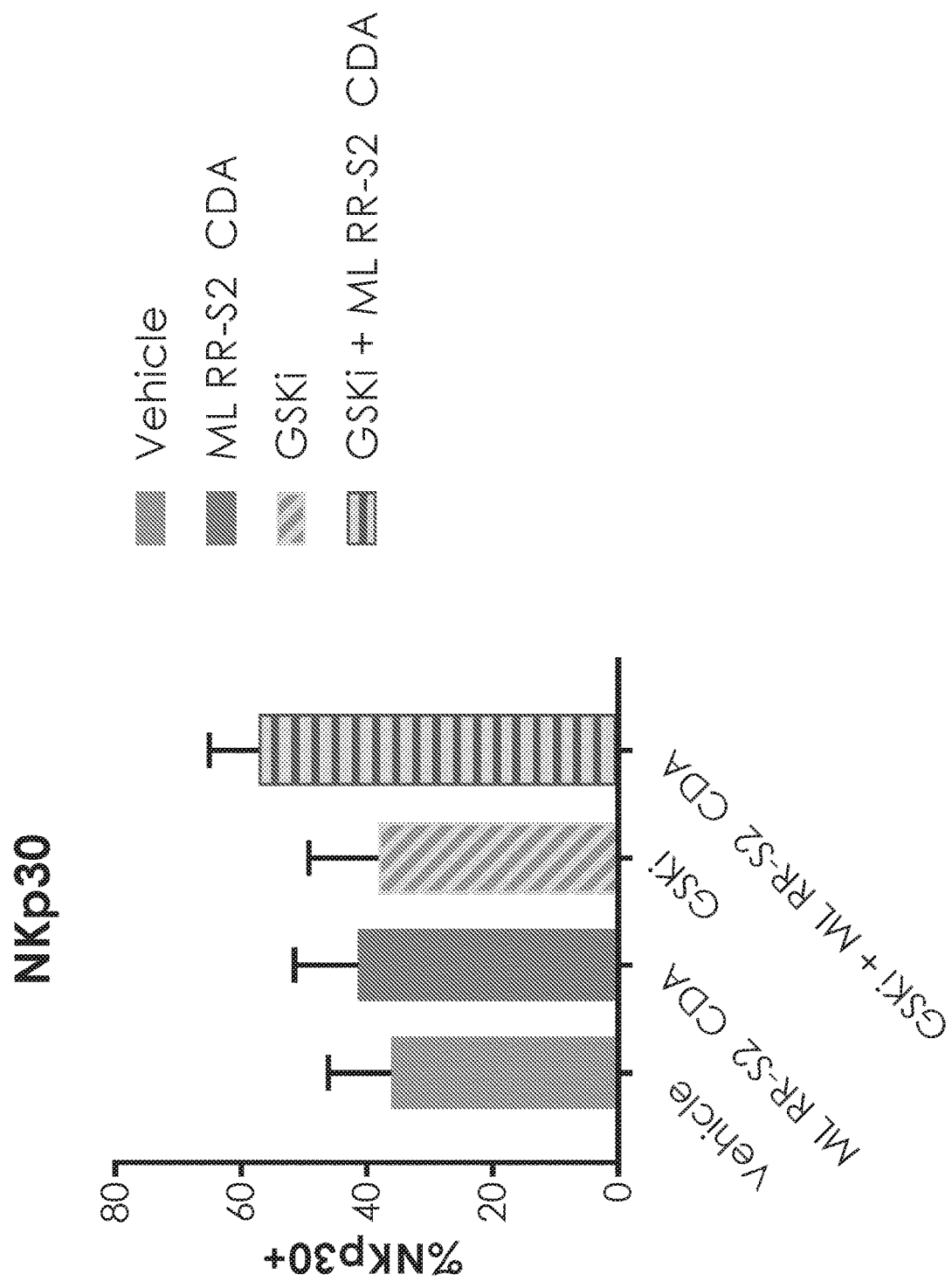
FIG. 19 shows that the combination of a GSK3 inhibitor and a STING agonist enhances NKp30 expression on NK cells.

Natural Killer (NK) cells recognize and destroy tumors and virus-infected cells in an antibody-independent manner. The regulation of NK cells is mediated by activating and inhibiting receptors on the NK cell surface. One important family of activating receptors is the natural cytotoxicity receptors (NCRs) which include NKp30, NKp44 and NKp46. The NCRs initiate tumor targeting by recognition of their specific ligands on cancer cells. As shown in FIG. 19, it is demonstrated that the combination of GSK3i and STING agonist enhances, synergistically, the NKp30 expression on modulated NK cells in comparison to NK cells modulated by the STING agonist or GSK3i alone, which may contribute, among other mechanisms, to the enhanced NK cell function.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of modulating a population of immune cells, comprising:
    contacting the immune cells with a sufficient amount of a composition comprising at least one agent for a time sufficient to obtain a population of modulated immune cells having improved therapeutic potential in comparison to unmodulated immune cells, wherein (a) the population of immune cells comprises T cells or NK cells; and (b) the at least one agent is selected from the group consisting of: Dorsomorphin; Heptelidic acid, 1-Pyrrolidinecarbodithioic acid, ammonium salt; 2-deoxyglucose (2-DG); GSK3 Inhibitors; Rho kinase inhibitors; MEK inhibitors, PDK1 agonists; TGFβ inhibitors; 6-Mercaptopurine; AC-93253 iodide; Tiratricol; PI-103; Fulvestrant; Thapsigargin; SU 4312; Telmisartan; Cyclosporin A; 1,3,5-tris(4-hydroxyphenol)-4-propyl-1H-pyrazole; BAY 61-3606; Protoporphyrin IX disodium; mTOR inhibitors; HS173; LY294002, Pictilisib; 5-Azacytidine; Fludarabine; Roscovitine, (S)-Isomer; PAC-1; 8-Quinolinol, 5,7-dichloro-; Nitrofurantoin; 8-Quinolinol, 5-chloro-7-iodo-; 2-Naphthacenecarboxamide, 7-chloro-4-(dimethylamino)-1,4,4a,5,5a,6,11,12a-octahy, Nifuroxazide; Tosufloxacin hydrochloride; Sertralin; Diethylenetriaminepentaacetic acid, penta sodium; Edrophonium chloride; BIX01294; Terfenadine; dmPGE2 (16,16-dimethyl Prostaglandin E2); and analogues thereof;
    and further wherein;
    (i) the immune cells are genetically modified to comprise an insertion, a deletion, or a nucleic acid replacement; or
    (ii) the method further comprises administering the modulated immune cells to a subject, wherein the modulated immune cells are autologous or allogeneic; and wherein the subject has an autoimmune disorder, a hematological malignancy, a solid tumor, cancer, or an infection associated with HIV, RSV, EBV, CMV, adenovirus, or BK polyomavirus.

2. The method of claim 1, wherein
the modulated immune cells comprise cells that have
    i. improved proliferation, cytotoxicity, cytokine response, cytokine release, cell recall, and/or persistence;
    ii. improved cell expansion, maintenance, differentiation, dedifferentiation, and/or survival rate; and/or
    iii. increased number or ratio of one or more desired subpopulations of immune cells, in comparison to immune cells not contacted with said at least one agent.

3. The method of claim 1, wherein the immune cells are differentiated in vitro from stem cells comprising induced pluripotent stem cells (iPSCs) or embryonic stem cells (ESCs).

4. The method of claim 1, further comprising administering the modulated immune cells to a subject, wherein the modulated immune cells are autologous or allogeneic; and wherein the subject has an autoimmune disorder, a hematological malignancy, a solid tumor, cancer, or an infection associated with HIV, RSV, EBV, CMV, adenovirus, or BK polyomavirus.

5. The method of claim 4, further comprising administering to the subject an antibody, a chemotherapeutic, or a radioactive treatment, wherein the antibody, chemotherapeutic, or radioactive treatment is prior to, during or after administering the modulated immune cells.

6. The method of claim 1, wherein the immune cells comprise T cells or NKT cells.

7. The method of claim 1, wherein the immune cells comprise NK cells, CD57-NK cells, or CD57-NKG2C+NK cells.

8. The method of claim 1, wherein the immune cells are isolated from or comprised in peripheral blood, bone marrow lymph node tissue, cord blood, thymus tissue, tissue from a site of infection, ascites, pleural effusion, spleen tissue, or tumors.

9. The method of claim 1, wherein the immune cells are isolated from: (1) a healthy subject; (2) a subject having an autoimmune disease, a hematopoietic malignancy, a virus infection or a solid tumor; (3) a subject previously administered with genetically modified immune cells; or (4) a subject that is CMV seropositive.

10. The method of claim 1, wherein the immune cells are genetically modified to comprise an insertion, a deletion, or a nucleic acid replacement.

11. The method of claim 1, wherein the immune cells (a) are differentiated in vitro from stem cells, hematopoietic stem or progenitor cells, or progenitor cells; or (b) are trans-differentiated in vitro from non-pluripotent cells of hematopoietic or non-hematopoietic lineage.

12. The method of claim 1, wherein the composition comprising said at least one agent further comprises one or more additives.

13. The method of claim 1, further comprising activating the immune cells prior to the step of contacting with a sufficient amount of the composition for modulation.

14. The method of claim 1, further comprising depleting CD3 and CD19 cells from the immune cells prior to contacting the immune cells with the composition comprising said at least one agent.

15. The method of claim 1, wherein the composition comprises:
one or more of a GSK3 inhibitor, a TGFβ receptor inhibitor, a ROCK inhibitor, a MEK inhibitor, a PDK1 agonist, and rapamycin.

16. The method of claim 2, wherein the modulated immune cells or the one or more desired immune cell subpopulation having increased number or ratio upon contacting with said one or more agents, comprise:
i. naïve T cells, stem cell memory T cells, central memory T cells, type I NKT cells, CD57+NK cells, or adaptive NK cells;
ii. adaptive NK cells comprising CD57+ and at least one of NKG2C+, low PLZF, low SYK, low FcεRγ, low EAT-2, low TIGIT, low PD1, low CD7, low CD161, high LILRB1, high CD45RO, and low CD45RA; or
iii. CD57+NK cells expressing hnCD16.

17. The method of claim 2, further comprising isolating the one or more desired subpopulations from the modulated immune cells.

18. The method of claim 1, wherein the time sufficient is no less than 16 hours.

19. The method of claim 1, wherein the immune cells for modulation are in a feeder-free environment.

20. The method of claim 7, wherein the NK cells:
i. have increased expression in one or more of CD107a, NKG2C, NKG2D, CD16, KIR, CD2, NKp30, NKp44 and NKp46, in comparison to unmodulated NK cells, wherein the expression thereof is increased by at least 10%, 20%, 30%, 40%, 50%, 60%, 70%, 80%, 90%, 100% or above;
ii. have increased expansion by at least 2 fold; and/or
iii. have improved cytokine response comprising increased production of one or more cytokines comprising IFNγ and/or TNFα.

21. The method of claim 11, wherein the immune cells are differentiated from stem cells, and wherein the stem cells comprise induced pluripotent stem cells (iPSCs) or embryonic stem cells (ESCs).

22. The method of claim 11, wherein the immune cells are differentiated from progenitor cells, and wherein the progenitor cells comprise CD34+ hemogenic endothelium cells, multipotent progenitor cells, T cell progenitor cells, NK progenitor cells, or NKT progenitor cells.

23. The method of claim 11, wherein the stem cell, hematopoietic stem or progenitor cell, or progenitor cell is genetically modified to comprise an insertion, a deletion, or a nucleic acid replacement.

24. The method of claim 10, wherein the immune cells are genetically modified to comprise at least one of safety switch proteins, targeting modalities, receptors, signaling molecules, transcription factors, pharmaceutically active proteins and peptides; or proteins promoting engraftment, trafficking, homing, viability, self-renewal, persistence, immune response regulation and modulation, or survival of the immune cells.

25. The method of claim 10, wherein the immune cells are genetically modified to comprise one or more of:
(a) deletion or reduced expression of B2M, TAP1, TAP2, Tapasin, NLRC5, PD1, LAG3, TIM3, RFXANK, CIITA, RFX5, or RFXAP, and any gene in the chromosome 6p21 region; or
(b) introduced or increased expression of HLA-E, HLA-G, CD16, hnCD16, 41BBL, CD3, CD4, CD8, CD47, CD113, CD131, CD137, CD80, PDL1, A2AR, Fc receptor, or surface triggering receptors for coupling with bi- or multi-specific or universal engagers.

26. The method of claim 12, wherein the one or more additives comprise:
(a) at least one of peptides, antibodies, antibody fragments, cytokines, mitogens, growth factors, small RNAs, dsRNA, mononuclear blood cells, feeder cells, feeder cell components or replacement factors, vectors comprising one or more polynucleic acids of interest, chemotherapeutic agents or radioactive moieties, and immunomodulatory drugs (IMiDs);
(b) at least one of stimulating cytokines comprising IL2, IL15, IL12, IL18 and IL21; or
(c) one or more of a MEK inhibitor, rapamycin, and a STING agonist.

27. The method of claim 1, wherein the composition comprises a GSK3 inhibitor.

28. The method of claim 1, wherein the composition comprises CHIR99021.

29. The method of claim 1, wherein the composition comprises a GSK3 inhibitor and IL15.

30. The method of claim 1, wherein the composition comprises a GSK3 inhibitor, IL15, and a STING agonist.

31. The method of claim 1, wherein the composition comprises at least one organic solvent selected from the group consisting of dimethyl sulfoxide (DMSO), N,N-dimethylformamide (DMF), dimethoxyethane (DME), dimethylacetamide, ethanol and combinations thereof.

* * * * *

UNITED STATES PATENT AND TRADEMARK OFFICE
CERTIFICATE OF CORRECTION

PATENT NO. : 11,096,964 B2
APPLICATION NO. : 16/071457
DATED : August 24, 2021
INVENTOR(S) : Jonathan Rosen et al.

Page 1 of 1

It is certified that error appears in the above-identified patent and that said Letters Patent is hereby corrected as shown below:

In the Claims

Column 66, Lines 17-18, in the sixteenth and seventeenth lines of Claim 1, delete
"1,3,5-tris(4-hydroxyphe-nol)-4-propyl-1H-pyrazole;" and insert
--1,3,5-tris(4-hydroxyphenyl)-4-propyl-1H-pyrazole;--

Column 66, Line 25, in the twenty-fourth line of Claim 1, delete "Sertralin" and insert --Sertraline--

Signed and Sealed this
Fourth Day of February, 2025

Coke Morgan Stewart
*Acting Director of the United States Patent and Trademark Office*